US009969801B2

(12) United States Patent
Tovey et al.

(10) Patent No.: US 9,969,801 B2
(45) Date of Patent: May 15, 2018

(54) CELL, METHOD AND KIT FOR CONDUCTING AN ASSAY FOR NEUTRALIZING ANTIBODIES

(75) Inventors: Michael Tovey, Paris (FR); Christophe Lallemand, Paris (FR)

(73) Assignees: LE CENTRE NATIONALE DE LA RECHERCHE SCIENTIFIQUE, Paris (FR); BIOMONITOR LIMITED, Galway (IE)

( * ) Notice: Subject to any disclaimer, the term of this patent is extended or adjusted under 35 U.S.C. 154(b) by 1351 days.

(21) Appl. No.: 12/921,110

(22) PCT Filed: Mar. 4, 2009

(86) PCT No.: PCT/US2009/036044
§ 371 (c)(1),
(2), (4) Date: Apr. 1, 2011

(87) PCT Pub. No.: WO2009/111572
PCT Pub. Date: Sep. 11, 2009

(65) Prior Publication Data
US 2011/0189658 A1 Aug. 4, 2011

Related U.S. Application Data

(60) Provisional application No. 61/033,621, filed on Mar. 4, 2008.

(51) Int. Cl.
| | |
|---|---|
| *C12N 1/00* | (2006.01) |
| *G01N 33/50* | (2006.01) |
| *G01N 33/68* | (2006.01) |
| *C12Q 1/68* | (2018.01) |
| *C07K 16/24* | (2006.01) |

(52) U.S. Cl.
CPC ....... *C07K 16/249* (2013.01); *G01N 33/5041* (2013.01); *G01N 33/6872* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,401,629 A | 3/1995 | Harpold et al. | |
| 5,436,128 A | 7/1995 | Harpold et al. | |
| 5,707,803 A | 1/1998 | Lamb et al. | |
| 5,712,094 A * | 1/1998 | Seidel ................. | C12Q 1/6897 435/252.3 |
| 5,891,718 A | 4/1999 | Hobart et al. | |
| 6,316,692 B1 | 1/2001 | Readhead et al. | |
| 7,045,281 B2 | 5/2006 | Livelli et al. | |
| 7,470,536 B2 | 12/2008 | Tovey et al. | |
| 2002/0086426 A1* | 7/2002 | Bujard et al. ................. | 435/440 |
| 2003/0219723 A1 | 11/2003 | Lu et al. | |
| 2004/0235157 A1 | 11/2004 | Tovey et al. | |
| 2005/0042643 A1 | 2/2005 | Cotter et al. | |
| 2007/0099245 A1 | 5/2007 | Gorovits et al. | |
| 2008/0081327 A1 | 4/2008 | Livelli et al. | |
| 2008/0138818 A1 | 6/2008 | Tovey et al. | |
| 2008/0248516 A1 | 10/2008 | Livelli et al. | |
| 2009/0111178 A1 | 4/2009 | Tovey et al. | |
| 2009/0136947 A1 | 5/2009 | Tovey et al. | |

FOREIGN PATENT DOCUMENTS

| | | |
|---|---|---|
| WO | 2004027374 A2 | 4/2004 |
| WO | WO/2004039990 A2 | 5/2004 |
| WO | 2008055153 A2 | 5/2008 |
| WO | WO/2008055153 A2 | 5/2008 |
| WO | WO/2009058884 A1 | 5/2009 |

OTHER PUBLICATIONS

Rang et al. The tetracycline-responsive promoter contains functional interferon-inducible response elements. Nucleic Acids Research. 2000. vol. 28, No. 5, pp. 1120-1125.*
Franzrahe et al. Establishment of Inducible Expression Systems to Study the Role of STAT-Transcription Factors in AML. 2003. Haematology and Blood Transfusion Hamatologie and Bluttransfusion. vol. 41, pp. 84-89.*
Office Action dated Apr. 7, 2006 of U.S. Appl. No. 10/677,777, 26 pages.
Office Action dated Sep. 7, 2007 of U.S. Appl. No. 10/677,777, 29 pages.
Office Action dated Mar. 19, 2008 of U.S. Appl. No. 10/677,777, 21 pages.
Office Action dated Oct. 16, 2009 of U.S. Appl. No. 11/765,262, 10 pages.
Office Action dated May 21, 2010 of U.S. Appl. No. 11/765,262, 10 pages.
Office Action dated Mar. 17, 2011 of U.S. Appl. No. 11/765,262 20 pages.
Office Action dated Sep. 2, 2010 of U.S. Appl. No. 11/928,965, 13 pages.
Office Action dated Apr. 14, 2010 of U.S. Appl. No. 12/336,121.
Final Office Action dated Nov. 24, 2010 of U.S. Appl. No. 12/336,121.
Ausubel et al, Current protocols in molecular biology, 4:A.3F.5-10.
ATCC catalog 1998, 2 pages.
Aschele et al., Cancer Research, 52:1855-1864 (1992).

(Continued)

*Primary Examiner* — Channing S Mahatan
(74) *Attorney, Agent, or Firm* — Browdy and Neimark, PLLC

(57) ABSTRACT

The present invention provides a cell for use in a one-step cell-based assay for an extracellular ligand (e.g., IFNα) that initiates a ligand-specific signal at the nucleus of the cell and for neutralizing antibodies against the extracellular ligand. The cell-based one-step assay allows both the extracellular ligand concentration and the neutralizing antibody titer to be quantified in a single sample (e.g., serum) without the need for sample dilution and addition of exogenous extracellular ligand.

27 Claims, 19 Drawing Sheets

(56) References Cited

OTHER PUBLICATIONS

Darnay et al., Activation of NF-kB by RANK requires tumor necrosis factor receptor-associated factor (TRAF) 6 and NF-kB-inudcing kinase, The Journal of Biological Chemistry, 274(12):7724-7731 (1999).
Deisenhammer F, Schellekens H, Bertolotto A., Measurement of neutralizing antibodies to interferon beta in patients with multiple sclerosis, J. Neurol. (2004) 251(Suppl. 2):11:31-11:39.
Ganster et al., Complex regulation of human inducible nitric oxide snythase gene transcription by Stat 1 and NF-kB, PNAS, 98(15):8638-8643 (2001).
Farrell et al., Development and validation of luciferase reporter gene assay to measure anti-interferon beta neutralizing antibodies, Neurology, 68(12):(Suppl. 1):A117-A118 (2007).
Lleonart et al., "A novel, quantitative bioassay for type I interferon using a recombinant indicator cell line" Biotechnology 8:1263-1267(1990).
Manna et al., IFN-alpha suppresses activation of nuclear transcription factors NF-kappa B and activator protein 1 and potentiates TNF-induced apoptosis, Journal of Immunology, 165(9)4927-4934 (2000).
Shen et al., The Journal of Biological Chemistry, 261(17):7762-7770 (1986).
Tovey et al., Characterization of neutralizing antibodies to interferons using a novel cell-based assay, Journal of Interferon and Cytokine Research, 27(8):735 (2007).
Bertolotto et al., Interferon beta neutralizing antibodies in multiple sclerosis: neutralizing activity and cross-reactivity with three different preparations, Immunopharmacology, 48:95-100 (2000).
Nagy et al., Preparing feeder cell layers from STO or mouse embryo fibroblast (MEF) cells: Treatment with γ-irradiation, Cold Spring Harb. Protoc.; 2006; doi:10.1101/pdb.prot4400, 2 pages.
Nagy et al., Preparing feeder cell layers from STO or mouse embryo fibroblast (MEF) cells: Treatment with mitomycin C, Cold Spring Harb. Protoc.; 2006; doi:10.1101/pdb.prot4399, 2 pages.
Huntsman et al., Blood Groups and Enzymes of Human Red Cells after Five Years' Storage in Liquid Nitrogen. British Medical Journal, vol. 4, 25 pp. 458-460 (1967).
Kushnaryov et al., "Ultrastructural Localization of Interferon Receptors on the Surfaces of Cultured Cells and Erythrocytes" Infection and Immunity, vol. 36, No. 2, p. 811-821 (1982).
Hodgins et al. Preservation of Trout and Salmon Erythrocytes for Blood Typing by Freezing with Dimethyl Sulphoxide. Nature, vol. 201, 28, pp. 1336-1337 (1964).
Yang et al., PNAS, 87:9568-9572 (1990).
Berry et al., Biochemical Pharmacology, 62:582-591 (2001).
Wei et al., Sheng Wu Hua Xue Yu Sheng Wu Wu Li Lue Bao, Shanghai, 33(1 ):123-127, abstract (2001).
Eichbaum et al., J. Exp. Med., 179:1985-1996 (1994).
Kim et al., Immunopharmacology and Immunotoxicology, 23(1):55-66 (2001).
Grossberg, et al., "The Expression of Potency of Neutralizing Antibodies for Interferons and Other Cytokines, Biotherapy" 10:93-98 (1997).
Grossberg et al., "The neutralization of interferons by antibody. I. Quantitative and theoretical analyses of the neutralization reaction in different bioassay systems" J Interferon Cytokine Res 21:729-42 (2001a).
Grossberg, et al. "The neutralization of interferons by antibody. II. Neutralizing antibody unitage and its relationship to bioassay sensitivity: the tenfold reduction unit" J Interferon Cytokine Res 21:743-55. (2001b).
Grossberg et al. "The Neutralization of Interferons by Antibody III. The Constant Antibody Bioassay, A Highly Sensitive Quantitative Detector of Low Antibody Levels" J Interferon Cytokine Res 29:93-104 (2009).
Lallemand et al., Constitutive expression of specific interferon isotypes in peripheral blood leukocytes from normal individuals and in promonocytic U937 cells, Journal of Leukocyte Biology, 60:137-146 (1996).

Canosi et al., A highly precise reporter gene bioassay for type I interferon, Journal of Immunological Methods, 199:69-76 (1996).
Files et al., A novel sensitive and selective bioassay for human type I interferons, Journal of Interferon and Cytokine Research, 18:1019-1024 (1998).
Lewis, A sensitive biological assay for interferons, Journal of Immunological Methods, 185:9-17 (1995).
Button et al., Aequorin-expressing mammalian cell lines used to report Ca2+ mobilization, Cell Calcium (Oct. 1993) 14(9):663-671.
Ahern H., Biochemical, reagents kits offer scientists good return on investment, The Scientist, 9(15):20-27 (1995).
Office Action dated Jun. 7, 2011 of U.S. Appl. No. 11/928,965, 17 pages.
Malucchi et al., Neurology, 62(11):2031-2037 (2004).
Office Action dated Aug. 21, 2009 of U.S. Appl. No. 12/260,871, 12 pages.
Office Action dated Apr. 12, 2010 of U.S. Appl. No. 12/260,871. 11 pages.
Supplementary European Search Report issued in corresponding European Patent Application No. EP09718276, dated Jul. 4, 2011, 11 pages.
Devgan et al., CignalTM reporter assay kit: A high performance tool for assessing the functions of genes, Biologics and Small Molecule Compounds, Internet Citation, pp. 1-6 (2008).
Hawkins et al., Dual-Glo TM luciferase assay system: A homogeneous dual-reporter system, Internet Citation, 4:14-15 (2002).
Lallemand et al., One-step assay for quantification of neutralizing antibodies to biopharmaceuticals, Journal of Immunological Methods, 356(1-2):18-28 (2010).
ATCC Catalogue of Cell Lines & Hybridomas 6th Edition. 1988. American Type Culture Collection, 10 pages.
Zatloukal et al., Elicitation of a systemic and protective anti-melanoma immune response by an IL-2-based vaccine, The Journal of Immunology, 3046-3419 (1995).
Hiscott et al., Triggering the Interferon Response: The Role of IRF-3 Transcription Factor, Journal of Interferon and Cytokine Research, 19:1-13 (1999).
Kessler et al, Two interferon-induced nuclear factors bind a single promoter element in interferon-stimulated genes, Proc. Natl. Acad. Sci. USA, 85:8521-8525 (1988).
Liu et al., ISG15 expression in response to double-stranded RNA or LPS in cultured Fetal Bovine Lung (FBL) cells, Vet Res Commun., 33:723-733 (2009).
Yang et al., Interferon Regulatory Factor-7 Synergizes with Other Transcription Factors through Multiple Interactions with p300/CBP Coactivators, The Journal of Biological Chemistry, 278:15495-15504 (2003).
Zhang et al., STAT3 activation in response to growth factors or cytokines participates in retina precursor proliferation, Exp Eye Res., 81(1):103-15 (2005) Abstract.
Levy et al., What does Stat3 do?, The Journal of Clinical Investigation, 109(9):1143-1148 (2002).
Feister et al., Identification of an IL-6 response element in the human LCAT promoter, Journal of Lipid Research, 43:960-970 (2002).
Matsumoto et al., CIS, a Cytokine Inducible SH2 Protein, Is a Target of the JAK-STAT5 Pathway and Modulates STAT5 Activation, Blood, 89(9):3148-3154 (1997).
Wurster et al., The biology of Stat4 and Stat6, Oncogene, 19:2577-2584 (2000).
De Groot et al., Activation of 12-O-Tetradecanoylphorbol-13-acetate Response Element- and Dyad Symmetry Element-dependent Transcription by Interleukin-5 Is Mediated by Jun N-terminal Kinase/Stress-activated Protein Kinase Kinases, The Journal of Biological Chemistry, 272(4):2319-2325 (1997).
Perera, The TATA Motif Specifies the Differential Activation of Minimal Promoters by Varicella Zoster Virus Immediate-early Regulatory Protein 1E62, The Journal of Biological Chemistry, 275(1):487-496 (2000).
Look et al., Stat1 Depends on Transcriptional Synergy with Sp1, The Journal of Biological Chemistry, 270 (51):30264-30267 (1995).

(56) References Cited

OTHER PUBLICATIONS

Meynier et al., Design of a chimeric promoter induced by pro-inflammatory mediators in articular chondrocytes, FEBS Letters, 518:67-71 (2002).

Pine, Convergence of TNFα and IFNγ signalling pathways through synergistic induction of IRF-1/ISGF-2 is mediated by a composite GAS/κB promoter element, Nucleic Acids Research, 25(21):4346-4354 (1997).

Ray et al., Activation of the human "Θ2-interferon/hepatocyte-stimulating factor/interleukin 6" promoter by cytokines, viruses, and second messenger agonists, Proc. Natl. Acad. Sci. USA, 85:6701-6705 (1988).

\* cited by examiner

CELL, METHOD AND KIT FOR CONDUCTING AN ASSAY FOR NEUTRALIZING ANTIBODIES

CROSS-REFERENCE TO RELATED APPLICATIONS

This application claims the benefit of priority from U.S. provisional application No. 61/033,621, filed Mar. 4, 2008, the entire content of which is herein incorporated by reference.

BACKGROUND OF THE INVENTION

Field of the Invention

The present invention relates to a reporter gene assay, and to the cells and kit for conducting such an assay.

Description of the Related Art

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as cytokines, growth factors, certain hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals indirectly alter gene expression by activating the expression of genes, such as immediate-early genes that encode regulatory proteins, which in turn activate expression of other genes that encode transcriptional regulatory proteins. Other extracellular signal molecules cause activation of latent cytoplasmic signal transducers and activators of transcription (STAT) protein that enhance the transcription of specific sets of genes.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell Surface Receptors

Cell surface-localized receptors are membrane spanning proteins that bind extracellular signalling molecules or detect changes in the extracellular environment and transmit the signal via signal transduction pathways to effect a cellular response. Cell surface receptors bind circulating signal molecules, such as cytokines, growth factors and hormones, etc., as the initiating step in the activation of numerous intracellular pathways. Receptors are classified on a structural basis or on the basis of the particular type of pathway that is induced. Among these classes of receptors are classes of cytokine receptors which include those that bind growth factors and have intrinsic tyrosine kinase activity, such as the heparin binding growth factor (HBGF) receptors, the immunoglobulin receptor superfamily, the hematopoietin/cytokine receptor superfamily, the nerve-growth factor receptor superfamily, other receptor tyrosine or serine kinases, and those that couple to effector proteins through guanine nucleotide binding regulatory proteins, which are referred to as G protein coupled receptors and G proteins, respectively.

Cytokines are intercellular messengers which coordinate communication between cells within a particular tissue, for example, antibody and T cell immune system interactions, and serve to modulate or modify the biological response. They are pleiotropic and have a broad spectrum of biological effects on more than one type of cell or tissue. The receptors for cytokines are broadly grouped into two classes, where the Class I cytokine receptors include receptors that bind various interleukins (IL-2, IL-3, IL-4, IL-6, IL-7, IL-9, IL-11, IL-12, IL-15), erythropoietin (EPO), growth hormone (GH), granulocyte colony stimulating factor (G-CSF), granulocyte macrophage colony stimulating factor (GM-CSF), leukemia inhibitory factor (LIF), and ciliary neurotrophic factor (CNTF), TNFα, TGFβ, Fas-ligand, and the Class II cytokine receptors include receptors that bind interferon (IFN) α/β, IFNγ, and IL-10.

Interferon Receptors

Human interferons (IFNs) are a family of homologous helical cytokines composed of three distinct classes: type I, type II, and type III based on nucleotide and amino acid sequence homology. Human Type I IFNs consist of IFN-α, IFN-β, IFN-ε, IFN-κ, and IFN-ω. Human IFN-α includes a group of closely related proteins encoded by at least 12 functional IFN-α genes. IFN-β, IFN-ε, IFN-κ, and IFN-ω, are encoded by single more distantly related genes. Type II IFN, or IFNγ, is encoded by an unrelated gene and binds to a distinct cell surface receptor (De Maeyer et al., 1988; Pestka et al., 1987 and Diaz et al., 1993). Recently, a novel group of interferons designated IFN-λ or type III IFNs has been described. The group has three members IFN-λ1, IFN-λ2, and IFN-λ3 also termed interleukin-29 (IL-29) (λ1), and IL-28A/B (λ2/3). (Sheppard et al., 2003; and Ank et al., 2006).

Type I IFNs bind to a common receptor, as shown by their ability to cross-compete for receptor binding (Pestka et al., 1987; Branca et al., 1981; and Merlin et al., 1985). The Type 1 interferon receptor has the largest number of natural ligands, some 14 in all, of all known cytokine receptors. Binding of interferons to their cell surface receptor represents the initial and probably most specific step in the IFN signaling pathway.

The Type I IFN receptor is composed of two transmembrane glycoproteins, IFNAR1 and IFNAR2 (Uze et al., 1990; Novick et al., 1994; Lutfalla et al., 1995; Domanski et al., 1995), which are rapidly tyrosine-phosphorylated following IFN binding (Platanias et al., 1994; Constantinescu et al., 1994; and Abramovich et al., 1994). Both subunits belong to the class II cytokine receptor superfamily (Bazan et al., 1990 and Thoreau et al., 1990) and are required for high affinity ligand binding and the establishment of biological activity (Langer et al., 1996 and Domanski et al., 1996). Class II cytokine receptors are distinguished from Class I receptors on the basis of the pattern of the conserved pairs of cysteine residues that are thought to form disulfide bonds.

The Type II IFN (IFN γ) receptor is composed of two transmembrane glycoproteins, IFNGR1 and IFNGR2 that are preassembled at the cell surface. Binding of IFN γ to its receptor activates the tyrosine kinases Jak1 and Jak2 resulting in tyrosine-phosphorylation and formation of a Stat1 homodimer. The activated Stat1 homodimer is then translocated to the nucleus where it binds to the GAS (Gamma Activated Sequence) resulting in transcriptional activation of IFN γ activated genes.

Type III interferons bind to a unique receptor comprising the IL-28Rα, which is specific for chain the IFN-γs, and the IL-10Rβ chain which is also part of the receptors for IL-10, IL-22, and IL-26 (Ank et al, 2006).

In contrast to other cytokine receptors, particularly the IFN-γ receptor, neither IFNAR1 nor IFNAR2 alone bind to IFNα or IFNβ with an affinity comparable to the heterodimer. Despite the fact that IFNAR2 plays a prominent role in ligand binding, IFNAR1 contributes to IFN binding by increasing the affinity of the receptor complex (4-10 fold) relative to that of IFNAR2 alone. IFNAR1 also modulates the specificity of ligand binding relative to that observed with IFNAR2 alone (Cohen et al., 1995; Russell-Harde et al., 1995; Cutrone et al., 1997; and Cook et al., 1996). IFNAR1 has a larger extracellular domain than most other class II cytokine receptors, composed of 4 immunoglobulin-like subdomains separated by di- or tri-proline motifs which can be divided into two tandem repeats (Novick et al., 1994; Lutfalla et al., 1992; and Uzé et al., 1995).

Human, murine and bovine IFNAR1 have been cloned and expressed in human and murine cells. Studies performed with transfected cells show that IFNAR1 plays a central role in ligand binding, cellular responses to IFNs and in the induction of the biological activities of the Type I interferons (Novick et al., 1994; Abramovich et al., 1994; Uzé et al., 1992; Mouchel-Vielh et al., 1992; Lim et al., 1993; Cleary et al., 1994; Constantinescu et al., 1995; Hwang et al., 1995; Vandenbroek et al., 1995; and Colamonici et al., 1994). The IFN receptor also determines the high degree of species specificity characteristic of the IFNs. Thus, transfection of mouse cells with IFNAR1 and IFNAR2 renders mouse cells sensitive to human type I IFNs since both human and mouse cells share a common signaling pathway and common IFN responsive elements in the promoter regions of IFN regulated genes. Furthermore, the intracellular domain of IFNAR1 has been shown to play a key role in the transduction of the signal initiated at the cell surface to the nucleus following binding of Type I interferons (Basu et al., 1998). Targeted disruption of the IFNAR1 gene results in the loss of the antiviral response to Type I IFNs demonstrating that this receptor polypeptide is an essential component of the receptor complex and that both IFNAR1 and IFNAR2 subunits are required for IFNα and IFNβ signaling (Vandenbroek et al., 1995; Muller et al., 1994; Fiette et al., 1995; Steinhoff et al., 1995; and van den Broek et al., 1995).

Binding of type I interferon to the receptor complex activates two Janus kinases, Tyk2 and JAK1, which mediate the tyrosine phosphorylation and activation of two latent cytoplasmic transcription factors STAT1 and STAT2 which form a complex (ISGF3) with a p48 DNA binding protein, interferon responsive protein 9 (IRF 9), which is translocated to the nucleus to promote specific gene transcription (Fu et al., 1992; Schindler et al., 1992; Darnell et al., 1994; Ihle et al, 1995; and Taniguchi, 1995). Both Tyk2 and STAT2 are constitutively associated with the membrane proximal region of the IFNAR1 chain, while JAK1 and STAT1 are physically associated with IFNAR2 and all four factors are rapidly activated during IFNα stimulation (Lutfalla et al., 1995; Bazan, 1990; Basu et al., 1998; Barbieri et al., 1994; Velazquez et al., 1995; Uddin et al., 1995; Yan et al., 1996 (a) and 1996(b).

Binding of type III IFNs to their cell-surface receptor also activates the ISGF3 complex suggesting that type III IFNs also activate a number of genes in common with type I IFNs (Ank et al., 2006).

Pattern Recognition Receptors

Key populations of cells including dendritic cells (DCs) distributed throughout the peripheral tissues act as sentinels capable of recognizing infectious agents through pattern-recognition receptors (PRR). These include the Toll-like receptor (TLR) family of cell surface and endosomal membrane receptors (Uematsu and Akira, 2007) and the retinoic acid-inducible gene I (RIG-I)-like cytosoloic receptor proteins RIG-I, MDA5, and LGP2 (Yoneyama and Fujita, 2007). Thirteen members of the TLR family have been identified in mammals (Uematsu and Akira, 2007). Each TLR mediates a distinctive response in association with different combinations of four Toll/IL-1 receptor (TIR) domain-containing adaptor proteins (MyD88, TRIF, TIRAP/MAL, and TRAM). All the TLRs except TLR3 interact with MyD88. TLR3, which recognizes single-stranded or double-stranded viral RNA, is localized in the endosomes of myeloid DCs and requires acidification of vesicles for activation. TLR3 signals via TRIF and activates TBK1/IKKe which phosphorylates the interferon regulatory factor 3 (IRF3) and NFkB, resulting in production of IFNβ (Hemmi et al, 2004, Perry et al., 2004). The RIG-1-like receptor proteins are DExD/H box RNA helicases two of which, RIG-I and MDA5, carry caspase activation and recruitment domain (CARD)-like motifs at the N-terminus (Yoneyama and Fujita, 2007). The CARD domain interacts with IPS-1 resulting in activation of IRF3 and NFkB and production of IFNβ. Thus, activation of PRRs leads to the production of pro-inflammatory cytokines including type I IFNs and activation of the innate immune response.

Dendritic cells signal principally through TLRs while RIG-1-like receptors predominate in other cell types. Two major DC sub-sets can be distinguished in man, CD11c(+) monocyte derived myeloid DCs, present in most tissues, and CD11c(−) plasmacytoid DCs (pDCs), present principally in lymph nodes. Plasmacytoid DCs are the principal producers of type I IFNs in response to viruses (Steinmann and Hemmi, 2006). Plasmacytoid DCs express high levels of TLR7/8 and TLR9 that recognize single-stranded RNA (ssRNA) and CpG DNA respectively (Diebold et al., 2004, Heli et al., 2004). Hemmi et al., 2000). Activation of both TLR7/8 and TLR9 leads to the formation of a complex with MyD88 and phosphorylation of IRF7 and production of high levels of type I IFNs (Uematsu and Akira, 2007).

TNF Receptors

Tumor necrosis factor alpha (TNF-α) is a multifunctional cytokine that exerts pleiotropic effects on different cell types. TNF-α is synthesized as pro-TNF, a 26 kDa membrane bound protein, which is released upon cleavage of its pro domain by TNF-converting enzyme (TACE) to yield a 17 kDa protein consisting of 157 amino acids that exists as a homotrimer in solution. TNF-α bind to two distinct receptors TNFR-1 (p55) and TNFR2 (p75). TNFR1 contains a death domain (absent from TNFR2) which is involved in the induction of apoptosis. Binding of the TNF-α homotrimer to TNFR-1 results in trimerization of TNFR-1 and the silencer of death domain (SODD) is released. The TNFR-associated death domain (TRADD) binds to the death domain of TNFR-1 and recruits the adaptor proteins, receptor interacting protein (RIP), TNFR-associated factor 2 (TRAF-2), and the Fas-associated death domain (FADD). TNFR-1 signals apoptosis, by FADD binding pro-caspase-8 the activation of which leads to induction of a protease cascade resulting in apoptosis. TNFR-1 signals survival by recruitment of TRAF-2 which inhibits apoptosis via the cytoplasmic inhibitor of apoptosis protein (cIAP). One of the principal signaling pathways triggered by recruitment of TRAF-2 and RIP to the TNFR-1 receptor complex is the NF-κB pathway which transduces a signal to the nucleus culminating in transcriptional activation of a number of TNF target genes (Schwamborn et al., 2003). NF-κB is a ubiquitous transcription factor induced by a number of cytokines (including IFNγ, IL2, IL5 and IFNα2). NF-κB is involved in the regulation of numerous genes involved in processes including, the inflammatory response, apoptosis, cancer, neuronal survival, and innate immunity. Activation of NF-κB is controlled principally at the posttranscriptional level by degradation of the inhibitory subunit IκB of the p55/p65/IκB complex present in the cytoplasm. Activating stimuli such as TNFα activate a kinase complex composed of two IκB-specific kinases (IKKα and IKKβ) and a modulatory subunit (NEMO or IKKγ). This leads to phosphorylation of the inhibitory subunit, which is then ubiquitinylated and degraded via the proteasome. This triggers translocation of NF-κB into the nucleus, where it initiates transcription by binding to regulatory sequences (NF-κB recognition/binding sequences) present in the promoter region of NF-κB target genes.

G-Coupled Receptors

The G protein transmembrane signaling pathways consist of three proteins: receptors, G proteins and effectors. G proteins, which are the intermediaries in transmembrane signaling pathways, are heterodimers and consist of α, β and γ subunits. Among the members of a family of G proteins the α subunits differ. Functions of G proteins are regulated by the cyclic association of GTP with the α subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

Growth Factors and Growth Factor Receptors

Polypeptide growth factors are modulators of cell proliferation and differentiation whose biological functions are mediated by the interaction of the growth factor with cell surface receptors and subsequent alterations in gene expression. Growth factors bind to specific receptors and appear to induce tyrosine phosphorylation and c-fos mRNA synthesis. In addition, at least some growth factors, such as platelet-derived growth factor (Yeh et al., 1987) and heparin-binding growth factor-2 or basic fibroblast growth factor (Bouche et al., 1987), are translocated to the nucleus.

Activation of growth factor receptors by interaction with specific growth factors or with agents such as phorbol mistric acetate (PMA) activates protein kinase C, which is a family of phospholipid- and calcium-activated protein kinases. This activation results in the transcription of an array of proto-oncogene transcription factor encoding genes, including c-fos, c-myc and c-jun, proteases, protease inhibitors, including collagenase type I and plasminogen activator inhibitor, and adhesion molecules, including intercellular adhesion molecule I. Protein kinase C activation antagonizes growth factor activity by the rapid phosphorylation of growth factor receptors, which thereby decreases tyrosine kinase activity. Growth factors and other mitogens that induce cell proliferation and cell growth are believed to play a role in tumor growth, which often carry identifiable cell surface receptors specific for growth factors and other extracellular signals.

The interaction of nerve growth factor (NGF) with its receptor is typical of the array of responses such an extracellular signal induces. NGF is a polypeptide growth hormone that is necessary for differentiation and growth of the neural crest-derived sensory neuron. NGF binds to its specific cell surface receptor and is retrogradely transported to the cell body (Changelian et al., 1989). This initiates a cascade of intracellular events, culminating in a differentiated phenotype. PC12 cells, which are a rat pheochromocytoma cell line, are used as a model for the study of NGF-mediated differentiation. When treated with NGF, PC12 cells change from replicating adrenal-chromaffin-like cells to nonreplicating, electrically excitable sympathetic-neuron-like cells.

Concomitant with the phenotypic changes, there is induction and expression of specific genes. Binding of NGF to PC12 cells induces the immediate and rapid expression of certain genes, including the c-fos, NGF1-A and NGF1-B genes, which are referred to as early genes. Such early genes are believed to encode transcriptional regulators. The NGF-1A gene product contains tandemly repeated "zinc finger" domains that are characteristic of DNA-binding proteins, and the NGF1-B protein is homologous to members of the glucocorticoid receptor family and, thus, may function as a ligand-dependent modulator of transcription. The c-fos gene product, FOS appears to function as a transcriptional regulatory molecule.

The c-fos Gene and Related Genes

As discussed above, induction of expression of the c-fos gene is an event that is common to a number of response pathways that are initiated by the activity of a variety of cell surface proteins.

The c-fos gene product, FOS, associates with the transcription activator JUN, which is the product of the c-jun gene, to form a complex that forms a transcription activation complex, AP-1. Transcription of both c-fos and c-jun is induced rapidly and transiently following stimulation. The induced mRNAs accumulate for 1-2 hours in the cytoplasm where the FOS and JUN proteins, which are short-lived, are translated and then translocated to the nucleus to form a heterodimeric protein complex that binds to the DNA regulatory element, the AP-1 binding site.

The c-fos and c-jun genes are members of gene families that encode proteins that participate in the formation of heterodimeric complexes that interact with AP-1 binding sites. Transcription factor AP-1 is composed of several protein complexes whose concentrations change upon cell stimulation. These complexes specifically interact with a seven-base core nucleotide sequence motif, that is known to be a relatively common constituent of both positive and negative transcriptional regulatory elements and that is required for both basal and induced levels of gene expression.

The gene products, FOS and JUN cooperate in the regulation of target genes that underlie many cellular and adaptive responses to the environment. They are involved in a number of neurophysiological processes.

Thus, c-fos induction involves distinct second messenger pathways that act via separate regulatory elements and that differentially modify, the resulting gene product, FOS, which in turn interacts in different ways with differentially modified JUN protein. Therefore, a multitude of extracellular events induce expression of a small number of inducible proteins that form an array of protein complexes that can differentially bind to DNA regulatory elements that contain AP-1 binding sites. Therefore, numerous cell surface proteins can act via overlapping transduction pathways and transduce extracellular signals that ultimately induce a variety of responses.

There are many assays that may rely on in vivo activity in a living cell line. One example is a cell line having an Interferon Stimulatory Response Element (ISRE) connected to a luciferase gene, or another reporter gene, so that when the cell line is subjected to the presence of interferon as an extracellular signal, the signal transduction activity of endogenous interferon cell surface receptors produces a signal that activates the ISRE, which then causes transcription of the luciferase gene. Thus, the activity of luciferase in creating light can be measured and is related to the amount of interferon which is present in the sample, and which is proportional to the amount of interferon over a particular range (Lallemand et al., 1996).

Lleonart et al. (1990) described a reporter gene assay for Type I interferon based on monkey Vero cells transfected with Type I interferon inducible mouse Mx promoter linked to the human growth hormone (hGH) gene as the reporter gene. This Type I interferon assay was developed further by transfecting monkey Vero cells with a plasmid carrying the luciferase reporter gene under the control of the Type I interferon inducible mouse Mx1 promoter (Canosi et al., 1996).

A further type of interferon reporter gene assay was developed by Hammerling et al. (1998) who used a human glioblastoma cell line transfected with a reporter gene construct of glial fibrillary acidic protein (GFAP) promoter and an E. coli β-galactosidase (lacZ) reporter gene. In this particular assay, it is the reduction/inhibition of β-galactosidase expression by either human Type I or Type II interferon in a selective and dose dependent manner that is measured.

Therapeutic proteins and in particular recombinant biopharmaceuticals represent an important and growing class of therapeutic agents. The safety and efficacy of therapeutic proteins can be severely impaired, however, by their immunogenicity. In addition to affecting pharmacokinetics, pharmacodynamics, bioavailability, and efficacy, anti-drug antibodies can also cause immune complex disease, allergic reactions and in some cases severe autoimmune reactions (Casadevall et al., 2002; and Neumann et al., 2000). It is widely accepted that injection of foreign proteins into humans can elicit an immune reaction leading to the production of binding and in some cases neutralizing antibodies (NAbs). Neutralizing antibodies block the biological activity of a biopharmaceutical either by binding directly to an epitope within or close to the active site of the protein or to an epitope that prevents binding of the drug to a cell surface receptor. It is becoming increasingly apparent, however, that repeated injection of recombinant homologues of authentic human proteins, such as interferon beta (IFNβ) or erythropoietin especially when aggregated or partially denatured, can result in a break in tolerance to self-antigens leading to the production of NAbs (Schellekens, 2008). This is of particular concern in the treatment chronic diseases such as certain forms of cancer and autoimmune disease. This can result in the failure of the patient to respond to therapy and may even prove to be life threatening in the case of NAbs that cross react with an essential non redundant endogenous protein such as erythropoietin (Casadevall et al., 2002) or megakaryocyte growth and development factor, MGDF (Neumann et al., 2000). Assessment of immunogenicity is therefore an important component of the evaluation of drug safety in both pre-clinical and clinical studies and is a prerequisite for the development of less immunogenic and safer biopharmaceuticals. Monitoring patients for the presence of NAbs to biopharmaceuticals and the correlation of immunogenicity with clinical data is key for determining the safety of treatment and for the interpretation of clinical data.

The results of a number of large randomized clinical studies have shown that interferon beta (IFNβ) reduces the frequency and severity of clinical relapses, slows disease progression, and improves the quality of life in patients with relapsing-remitting multiple sclerosis (RRMS) (Clerico et al., 2007; and McCormick et al., 2004). Repeated treatment with recombinant IFNβ, however, can cause a break in immune tolerance to self-antigens in some patients, resulting in the production of neutralizing antibodies (NAb) to the recombinant protein homologue (Hartung et al., 2007; Noronha, 2007; and Namaka et al., 2006). Appearance of NAbs is associated with both reduced pharmacodynamics (induction of IFNβ responsive gene products; Deisenhammer et al., 2004), and a reduced clinical response determined by either magnetic resonance imaging (MRI) or disease progression (Hartung et al., 2007; Noronha, 2007; and Namaka et al., 2006). The frequency and titers of anti-IFNβ antibodies vary as a function of the type of IFNβ preparation used to treat the patient, as well as the frequency and route of administration. Although direct comparisons among many of the studies is difficult due to the use of different neutralization assays and standards, comparative studies have shown that IFNβ-1b is more immunogenic than IFNβ-1a (Bertolotto et al., 2002) possibly due to the lower specific activity of IFNβ-1b and hence the higher protein mass injected (Antonetti et al., 2002). Amino acid differences, lack of glycosylation of recombinant IFNβ-1b compared with the native protein or currently licensed forms of IFNβ-1a, or formulation characteristics may also contribute to the immunogenicity of IFNβ-1b (Giovannoni, 2004).

Two principal approaches are used to quantify anti-drug NAbs: the constant antigen method in which a constant amount of drug (e.g., IFN) is mixed with serial dilutions of serum, and the constant antibody method in which a fixed dilution of serum is mixed with varying concentration of drug. In both cases the titration end-point is usually taken as the median of the maximum and minimum values of the dose-response curve which is defined as one laboratory unit (LU). NAb titer is usually determined using the Kawade method of calculation that determines the serum dilution that reduces drug activity from 10 to 1 LU/ml (Grossberg et al., 2001a and 2001b). Residual drug activity is usually determined using a cell-based assay. Such assays are notoriously difficult to standardize and are at best semi-quantitative due to the absence of appropriate standards for anti-drug NAbs.

Current methods for detecting the presence of neutralizing antibodies to IFNα or IFNβ are based on the inhibition of IFN activity determined using either antiviral bioassays (Grossberg et al., 2001a and 2001b) or induction of an IFN induced protein (Deisenhammer et al., 2004). Bioassays based on the ability of IFNs to inhibit virus replication 1) are imprecise and require skilled operators in order to obtain reproducible results, 2) only two fold or greater differences can be detected, 3) give variable results, and 4) take several days to complete. Measurement of the induction of an IFN-induced antiviral protein such as MxA requires use of cell lines or peripheral blood, and subsequent evaluation of protein levels by ELISA or measurement of MxA mRNA levels (Deisenhammer et al., 2004).

A highly sensitive and reproducible method for quantifying type I IFN activity has recently been developed, based on human pro-monocytic U937 cells, transfected with the firefly luciferase reporter-gene controlled by an IFN responsive chimeric promoter (Lallemand et al., 2008), which allows IFN activity to be determined selectively with a high degree of precision, and within a few hours. Treatment of these cells (PIL5) with the anti-mitotic drug vinblastin allows cells to be stored frozen for prolonged periods without loss of IFN sensitivity or the need for cell cultivation and avoids assay variation associated with cell proliferation (Lallemand et al., 2008). Although this assay overcomes many of the limitations of conventional cell-based neutralization assays or other reporter-gene assays (Lam et al., 2008) for the determination of IFN activity or for the quantification of anti-IFN Nabs, it remains relatively labor intensive. Thus, quantification of anti-IFN NAbs requires serial dilutions of the serum sample to be tested, a simultaneous IFN dose-response curve, and positive and negative controls to be included in each assay as well as the availability of reference reagents.

Bioassays for TNF-α are based on the ability of TNFα to induce apoptosis in susceptible cells such as mouse L929 cells, usually in the presence of actinomycin D. Such assays are imprecise and difficult to use for the determine of NAbs to TNFα antagonists such as Infliximab, Adalimumab or etanercept (Meager A, 2006).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a cell for use in assaying for antibodies against an extracellular ligand that initiates a ligand-specific signal at the nucleus of the cell. The cell according to the present invention contains (1) a first DNA construct having a sequence that includes a first set of one or more transcription control elements, which is inducible by the ligand, and also encodes a first measurable tag (first reporter gene product), whose expression is driven by the first set of one or more transcription control elements when induced by the presence of the ligand and (2) a second DNA construct having a sequence that includes a second set of one or more transcription control elements different from the first, a DNA segment encoding a second measurable tag (second reporter gene product) whose expression is driven by the second set of one or more transcription control elements, and on a separate cistron a segment encoding a ligand, whose expression is also driven by the second set of one or more transcription control elements.

The present invention also provides a kit containing a plurality of the cell according to the present invention, which kit is used for determining in a sample the level of an extracellular ligand that initiates a ligand-specific signal at the nucleus of the cell or of a neutralizing antibody against either the extracellular ligand or an antagonist of the extracellular ligand. Additionally, the present invention further provides a method for determining such a level in a sample.

BRIEF DESCRIPTION OF THE DRAWINGS

In FIGS. 15A and 15B, RL represents Renilla luciferase and luc represents Firefly luciferase.

DETAILED DESCRIPTION OF THE INVENTION

Conventional cell based assays for the quantification of neutralizing antibodies (NAbs) are imprecise, give variable results, and often require two or more days to complete. Furthermore, conventional cell-based assays require specialized personnel and biological containment facilities, are labor intensive, and difficult to automate. The use of division-arrested frozen cells transfected with a reporter gene controlled by a ligand-responsive chimeric promoter (WO 2004/039990 and US 2004/023517, incorporated herein by reference) in an assay for neutralizing antibodies would allow anti-ligand NAbs to be quantified with precision within hours. Although such an assay would overcome many of the limitations of conventional cell-based neutralization assays, it would still remain relatively labor intensive and require serial dilutions of both the test sample and ligand, positive and negative controls, and reference reagents, to be included in the assay. Furthermore, assay precision is adversely affected by loss of assay cells (or carry-over of ligand or NAb following serial dilution). Such assays also remain relatively difficult to automate.

Figure 2:
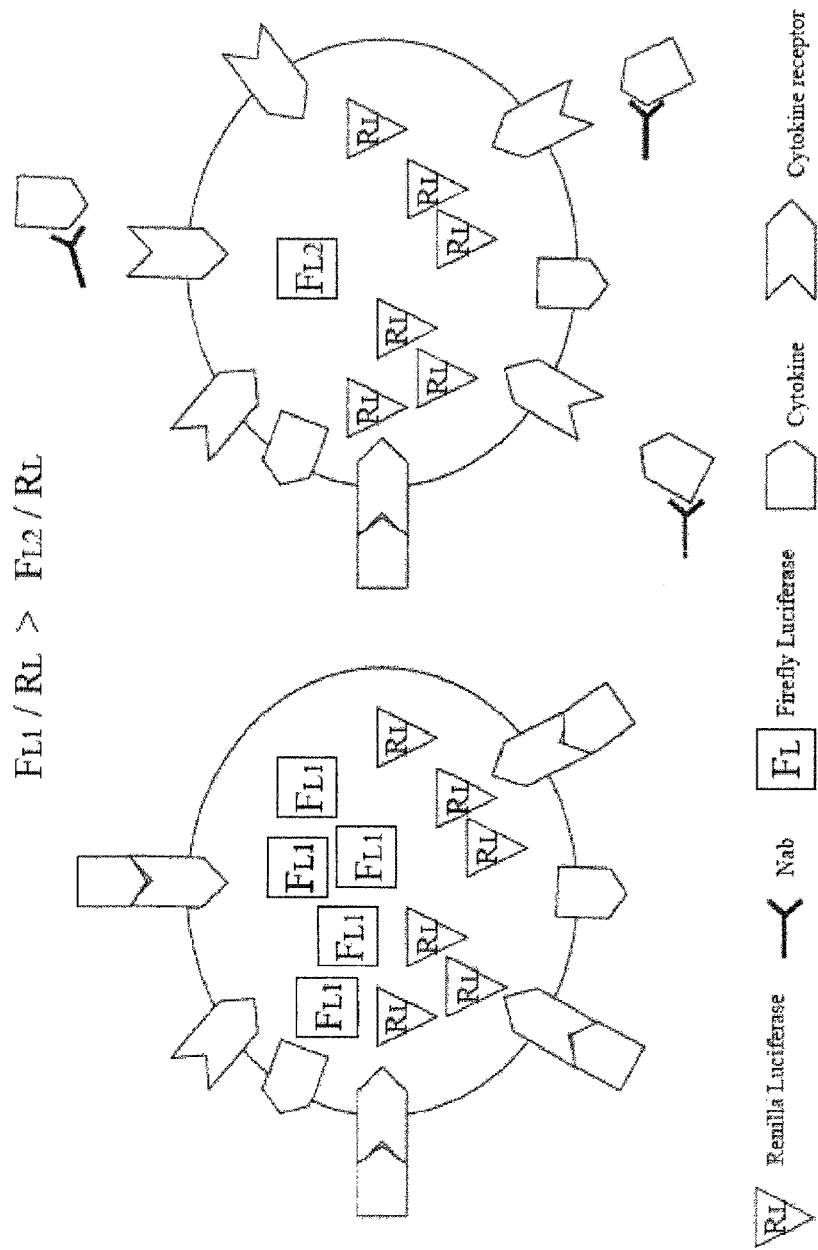
FIG. 2 is a schematic illustration of an embodiment in which the ligand (cytokine) and the *Renilla* luciferase (RL) reporter gene are expressed from the same promoter. The *Renilla* luciferase remains in the cell while the expressed cytokine is secreted, interacting with a receptor for the cytokine ligand which initiates signal transduction to drive expression of firefly luciferase (FL) from a cytokine ligand-responsive promoter. The presence of neutralizing antibodies (NAb) for the cytokine prevents the cytokine from interacting with its cell surface receptor and results in a corresponding reduction in the activity of the cytokine (as determined by the relative activity of the cytokine-responsive firefly luciferase reporter, FL1/RL (control)>FL2/RL).

The present invention avoids the limitations of the currently available assays as discussed above by developing a cell, and an assay for the quantification of neutralizing antibodies based on using such a cell, which has been engineered to express and secrete the ligand (extracellular ligand) of interest and a reporter gene transcribed from the same inducible promoter. The cell also contains another reporter gene controlled by a chimeric promoter which is ligand-responsive. Expression of the former reporter product gene is strictly proportional to the expression of the ligand and allows ligand expression to be quantified (i.e., by determining the amount of expressed reporter gene product). Expression of the latter ligand-responsive reporter gene allows ligand activity to be quantified as well. The presence of anti-ligand NAbs in the immediate environment of the cell will neutralize a quantity of extracellular ligand (secreted from the cell) proportional to the neutralization capacity of the antibody, and thus prevent the extracellular ligand from interacting with its specific cell surface receptor (or with a pattern recognition receptor). This will result in a corresponding reduction in the activity of the extracellular ligand, and hence the expression of the ligand-responsive reporter-gene, the activity of which can be quantified. FIG. 2 schematically illustrates this system using levels of firefly luciferase (FL) and *Renilla* luciferase (RL) activity.

The degree of reduction in the expression of the ligand-responsive reporter gene in the presence or absence of the NAb sample to be quantified will allow the relative neutralizing titer of the sample to be quantified, relative to a given level of expression of a different reporter gene transcribed from the same promoter as the ligand.

Figure 1:
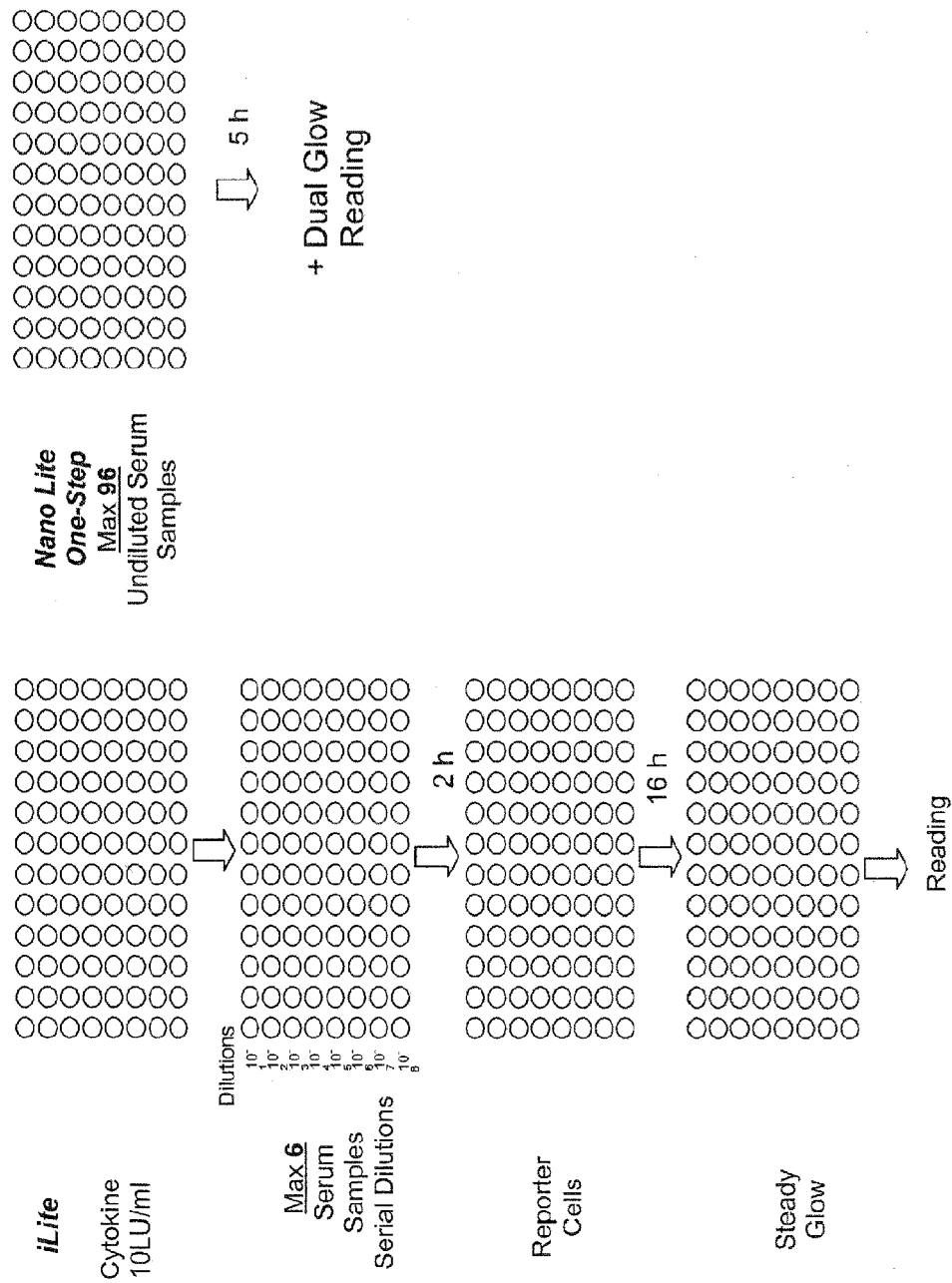
FIG. 1 is a schematic flow diagram of the steps performed in the recent "iLite" cell-based assay and in the "NanoLite" one-step assay according to the present invention.

The cell and the cell-based assay method (termed "NanoLite" as opposed to the "iLite" assay method of WO2004/039990 and US2004/023517) according to the present invention, when used for assaying neutralizing antibodies, has many advantages over the conventional cell-based assay (i.e., CPE) and even over the more recent "iLite" cell-based assay in that it is essentially a one-step assay (where only undiluted sample need to be added to the cells). FIG. 1 presents a flow diagram comparison between the recent iLite cell-based assay and the NanoLite assay of the present invention, which clearly shows that NanoLite involves less steps and less time to perform. It should be noted that the NanoLite assay according to the present invention, using the cell of the present invention, is a one-step assay where, in contrast to the iLite or other conventional cell-based assays, neither addition of ligand (cytokine) nor dilution of the sample is required. Table 1 below further summarizes the many advantages that the NanoLite assay method of the present invention has over the CPE and iLite assays.

TABLE 1

|  | CPE | iLite | Nano Lite |
|---|---|---|---|
| Time (hours) | 96 | 18 | 5 |
| Reagents Required | + | + | − |
| Serial Dilutions | + | + | − |
| Positive Control | + | + | − |
| Negative Control | + | + | − |
| Ligand Standard Curve | + | + | − |
| Results/Cell Number | + | + | − |
| Maximum Samples/plate | 10 | 10 | 96 |
| HTS Automated | − | +/− | + |

As contemplated by the present inventors, the cell of the present invention, for use in assaying antibodies to an extracellular ligand that initiates a ligand-specific signal at the nucleus of the cell, contains at least (a) a first DNA construct, which has a sequence that includes a first set of one or more transcription control elements that is inducible by the ligand, and a portion encoding a first measurable tag (i.e., reporter gene product) driven by the first set of one or more transcription control elements, where the first tag can be detected when the first set of one or more transcription control elements is induced by the ligand, (b) a second DNA construct, which has a sequence that includes (i) a second set of one or more transcription control elements different from the first set, (ii) a DNA segment, driven by the second set of one or more measurable tag (i.e., second reporter gene product different from the first) which can be independently measured in the presence of the first tag, and vice versa, and (iii) on a separate cistron, a DNA segment encoding the ligand, also driven by the second set of one or more transcription control elements.

The cell according to the present invention may be any mammalian or avian cell line, with human cells most preferred. Preferred cell lines include but are not limited to, human promonocytic (i.e., U937), myeloid (i.e., U266R), T-cell lymphoma (i.e., Jurkatt), breast adenocarcinoma (i.e., MCF7) cell lines and mouse lymphoma (i.e., L120) and erythroid leukemia cell lines.

The extracellular ligand (or its antagonist/antibody), for which the titer of neutralizing antibodies thereto are determined in the method according to the present invention discussed below, is intended to encompass any therapeutic agent, such as therapeutic proteins, which activates (or blocks, in the case of an antagonist of/antibody against the extracellular ligand) the signal transduction activity of a cell surface protein, and for which neutralizing antibodies generated thereto in the mammalian subject treated with the therapeutic agent would be undesirable. The extracellular ligand may also encompass components of molecules or preparations such as live or attenuated virus or bacterial vaccines, which components interact with pattern recognition receptors. Preferred non-limiting examples of such an extracellular ligand include cytokines, chemokines and growth factors, such as interferon-α, interferon-β, interferon-γ, erythropoietin (EPO), TNFα, interleukins, growth hormone, granulocyte colony stimulating factor (G-CSF) and granulocyte macrophage colony stimulating factor (GM-CSF); gonadotropins, insulin and other hormones; integrins; immunoglobulins (polyclonal, monoclonal, chimeric, humanized or single chain, etc.); and other proteins that interact with a cell surface molecule or with a pattern recognition receptor to transmit a signal to the nucleus. Non-limiting examples of antagonists (i.e., antibodies) of the extracellular ligand, which antagonist the neutralizing antibodies bind to, include TNFα antagonists such as Enbrel and Infliximab (a chimeric antibody), Adalimumab (a fully human antibody), and Etanercept (an IgG1Fc TNFp75 receptor fusion protein).

Neutralizing antibody (NAb) assays are clinically very important today because those patients being treated continuously for a chronic disease, such as remitting/relapsing MS treated with interferon β, cease obtaining benefit from treatment with the therapeutic agent once an immune response, in particular production of NAbs, has been mounted against the therapeutic agent by the patient. Thus, it is important to be able to detect when and if a patient has developed NAbs in order to stop treatment at that point. Also, it will prevent the possibility of adverse reactions such as anaphylactic shock and perfusion reactions, and allow the patient to be treated with an alternative effective therapy. Furthermore, NAb testing can provide considerable cost savings to the health care provider/insurer and to the patient by avoiding continued use of an ineffective and expensive biopharmaceutical.

The cell surface protein from which its signal transduction activity, in response to an extracellular signal from a therapeutic agent or protein, regulates the expression of a reporter gene product can be any such cell surface protein that is known to those of skill in the art or that may be identified by those of skill in the art. Exemplary cell surface proteins include, but are not limited to, cell surface receptors and ion channels. Non-limiting examples of cell surface receptors include cytokine receptors (e.g., receptors for Type I interferon, Type II interferon, interleukins, growth hormone, erythropoietin (EPO), granulocyte colony stimulating factor (G-CSF), granulocyte macrophage colony stimulating factor (GM-CSF), TNFα, TGFβ, Fas ligand, leukemia inhibitory factor (LIF), ciliary neurotrophic factor (CNTF), etc.), growth factor receptors, hormone receptors, T cell receptors, antigen receptors, complement receptors, and neuroreceptors. The reference text, J. M. Cruse and Robert E. Lewis, *Atlas of Immunology*, CRC Press, Washington, D.C., 1999, which discloses many receptors involved in immune response and immune system interactions is entirely incorporated herein by reference. Cell surface receptors also include, but are not limited to, muscarinic receptors (e.g., human M2 (GenBank accession #M16404); rat M3 (GenBank accession #M16407); human M4 (GenBank accession #M16405); human M5 (Bonner et al., 1988); and the like); neuronal nicotinic acetylcholine receptors (e.g., the α2, α3 and β2 subtypes); the rat α2 subunit (Wada et al., 1988); the rat α3 subunit (Boulter et al., 1986); the rat α4 subunit (Goldman et al., 1987); the rat α5 subunit (Boulter et al., 1990); the rat β2 subunit (Deneris et al., 1988); the rat β3 subunit (Deneris et al., 1989); the rat β4 subunit (Duvoisin et al., 1989); combinations of the rat α subunits, β subunits and α and β subunits; GABA receptors (e.g., the bovine α1 and β1 subunits (Schofield et al., 1987); the bovine α2 and α3 subunits (Levitan et al., 1988); the γ-subunit (Pritchett et al., 1989); the β2 and β3 subunits (Ymer et al., 1989); the δ subunit (Shivers, B. D., 1989); and the like); glutamate receptors (e.g., receptor isolated from rat brain (Hollmann et al., 1989); and the like); adrenergic receptors (e.g., human β1 (Frielle et al., 1987); human α2 (Kobilka et al., 1987); hamster β2 (Dixon et al., 1986); and the like); dopamine receptors (e.g., human D2 (Stormann et al., 1990); rat (Bunzow et al., 1988); and the like); NGF receptors (e.g., human NGF receptors (Johnson et al., 1986); and the like); serotonin receptors (e.g., human 5HT1a (Kobilka et al., 1987); rat 5HT2 (Julius et al., 1990); rat 5HT1c (Julius et al., 1988); and the like).

The pattern recognition receptor from which its signal transduction activity, in response to an extracellular signal from a component(s) of a molecule or preparation such as a live or attenuated virus or bacterial vaccine regulates the expression of a reporter gene product, includes but is not limited to Toll-like receptors (TLR) cell surface or endosomal membrane receptors (Uematsu and Akira, 2007), or the retinoic acid-inducible gene 1 (GIG-I)-like cytosolic receptor proteins RIG-I, MDA5, and LGP2 (Yoneyama and Fujita, 2007) that recognize or interact with components of live or attenuated virus or bacterial vaccines. Evaluation of neutralizing antibodies generated in the mammalian subject treated with the vaccine is important in order to determine the degree of protection afforded by vaccination.

Thirteen members of the TLR family have been identified in mammals (Uematsu and Akira, 2007). Each TLR mediates a distinctive response in association with different combinations of four Toll/IL-1 receptor (TIR) domain-containing adaptor proteins (MyD88, TRIF, TIRAP/MAL, and TRAM). All the TLRs except TLR3 interact with MyD88. TLR3, which recognizes single-stranded or double-stranded viral RNA, is localized in the endosomes of myeloid DCs and requires acidification of vesicles for activation. TLR3 signals via TRIF and activates TBK1/IKKε which phosphorylates the interferon regulatory factor 3 (IRF3) and NFκB, resulting in production of IFN β (Hemmi et al, 2004, Perry et al., 2004). The RIG-1-like receptor proteins are DExD/H box RNA helicases two of which, RIG-I and MDA5, carry caspase activation.

Ion channels include, but are not limited to, calcium ion channels (e.g., human neuronal α2 subunit (see WO89/09834); rabbit skeletal muscle al subunit (Tanabe et al. 1987); rabbit skeletal muscle α2 subunit (Ellis et al., 1988); rabbit skeletal muscle β subunit (Ruth et al., 1989); rabbit skeletal muscle γ subunit (Jay et al., 1990); and the like); potassium ion channels (e.g., rat brain (BK2) (McKinnon, D., 1989); mouse brain (BK1) (Tempel et al., 1988); and the like); sodium ion channels (e.g., rat brain I and II (Noda et al., 1986); rat brain III (Kayano et al., 1988); and others).

It will be appreciated by those of skill in the art that the cell surface protein or pattern recognition receptor discussed above is preferably endogenous to the cell of the present invention. However, it will also be appreciated that the cell surface protein or pattern recognition receptor may be expressed from cloned DNA, such as to supplement the number of pattern recognition receptors or the number of the cell surface protein at the surface of the cell, or the cell surface protein or pattern recognition receptor may be expressed from cloned DNA but is a cell surface protein or pattern recognition receptor that is heterologous to the host cell.

For signal transduction, the intracellular signal that is transduced is initiated by the specific interaction of an extracellular signal with a receptor or ion channel present on the cell surface. This interaction sets in motion a cascade of intracellular events, including a ligand-specific signal at the nucleus of the cell, the ultimate consequence of which is a rapid and detectable change in the expression of a gene product, which in the cell of the present invention is preferably a reporter gene product. The extracellular signal or effector molecule is any compound or substance that acts as a ligand to specifically alter the activity of a cell surface protein or pattern recognition receptor. Examples of such signals include, but are not limited to, molecules such as cytokines (i.e., interferons), growth factors, hormones, endorphins, neurotransmitters, acetylcholine, and mitogenic substances, such as phorbol myristic acetate (PMA), that bind to cell surface receptors and ion channels and modulate the activity of such receptors and channels. Other examples include components of live and attenuated virus and bacterial vaccines.

The DNA constructs carried by the cell according to the present invention are DNA constructs that include a nucleotide sequence encoding a reporter gene product operatively linked to transcriptional control elements/sequences. Transcription of the reporter gene is controlled by these sequences. The activity of at least one or more of these control sequences is directly or indirectly regulated by the cell surface protein or pattern recognition receptor. The transcriptional control sequences include but are not limited to promoters and other regulatory regions, such as enhancer sequences and repressor and activator binding sites, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein or a pattern recognition receptor. For example, modulation of the activity of the promoter may be affected by altering the RNA polymerase binding to the promoter region, or, alternatively, by interfering with initiation of transcription or elongation of the mRNA. Such sequences are herein collectively referred to as transcriptional control elements or sequences. In addition, the constructs may include sequences of nucleotides that alter translation of the resulting mRNA, thereby altering the amount of reporter gene product expressed.

A promoter that is regulated or mediated by the activity of a cell surface protein or pattern recognition receptor is a promoter whose activity changes when a cell is exposed to a particular extracellular signal (ligand) by virtue of the presence of cell surface proteins or pattern recognition receptors whose activities are affected by the extracellular signal. For example, the c-fos promoter is specifically activated upon the specific interaction of certain extracellular signals, such as growth hormones, with a cell surface protein, such as a growth hormone receptor. In particular, the regulation of such promoters by the cell surface protein, though indirect, occurs within minutes of the interaction of the cell surface protein with the extracellular signal. As used herein, operative linkage refers to the linkage of a transcriptional control element, i.e., promoter, to a nucleotide coding sequence such that the transcriptional control element is properly positioned for its activity of binding RNA polymerase and initiating transcription of the nucleotide coding sequence. Thus, a nucleotide coding sequence in operative linkage with a promoter is downstream, with respect to the direction of transcription, from the promoter, is in the correct reading frame with respect to the transcription initiation site and is inserted in a manner such that transcription elongation proceeds through the nucleotide coding sequence.

Suitable transcriptional control elements may be obtained or derived from the transcriptional regulatory regions of genes whose expression is rapidly induced, generally within minutes, of contact between the cell surface protein or pattern recognition receptor and the effector ligand that modulates the activity of the cell surface protein or pattern recognition receptor. Examples of such genes include, but are not limited to, the immediate early genes (Sheng et al., 1990), such as c-fos. Immediate early genes are genes that are rapidly induced upon binding of a ligand to a cell surface protein. The transcriptional control elements that are preferred for use in the DNA (reporter gene) constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Suitable promoters and transcriptional control elements include, but are not limited to, the cytomegalovirus promoter (CMV), the simian virus 40 (SV40) promoter and minimal promoters thereof, the vasoactive intestinal peptide (VIP) gene promoter (cAMP responsive; Fink et al., 1988); the somatostatin gene promoter (cAMP responsive; Montminy et al., 1986); the proenkephalin promoter (responsive to cAMP, nicotinic agonists, and phorbol esters; Comb et al. 1986); the phosphoenolpyruvate carboxy-kinase gene promoter (cAMP responsive; Short et al., 1986); the NGFI-A gene promoter (responsive to NGF, cAMP, and serum; Changelian et al., 1989); the transcriptional control elements obtained or derived from the c-fos gene; and others that may be known to or prepared by those of skill in the art.

The c-fos proto oncogene is the cellular homologue of the transforming gene of FBJ osteosarcoma virus. It encodes a nuclear protein that is most likely involved in normal cellular growth and differentiation. Transcription of c-fos is transiently and rapidly activated by growth factors and by inducers of other cell surface proteins, including hormones, differentiation-specific agents, stress, mitogens and other known inducers of cell surface proteins. Activation is protein synthesis independent. The c-fos regulatory elements include a TATA box that is required for transcription initiation, two upstream elements for basal transcription, and an enhancer, which includes an element with dyad symmetry and which is required for induction by TPA, serum, EGF, and PMA. The 20 bp transcriptional enhancer element located between −317 and −298 bp upstream from the c-fos mRNA cap site, which is essential for serum induction in serum starved NIH 3T3 cells. One of the two upstream elements is located at −63 to −57 and it resembles the consensus sequence for cAMP regulation.

Transcriptional control elements, particularly as they relate to a preferred embodiment of the present invention where Type I and/or Type II interferon is the extracellular signal, are preferably an interferon stimulatory response element (ISRE) and/or a gamma activated sequence (GAS). There are a number of ISREs characterized from different human genes responsive to Type I interferon and a consensus sequence, ggraaagwGAAActg (SEQ ID NO:1; capital letters denote core sequence; underlines denote high conservation), to which the STAT1/STAT2/IRF9 complex binds, was identified for ISRE (Levy et al., 1988). A preferred ISRE is from the human ISG15 gene and is presented as SEQ ID NO:2 where nucleotides 41-55 correspond to the consensus ISRE sequence. ISRE is also highly conserved among species. For example, a sequence present in the promoter region of the interferon inducible chicken Mx gene (Schumacher et al., 1994) is similar to that found in primates and conforms to the ISRE consensus sequence for mammalian interferon responsive genes including rodents and cows (see FIG. 2 of Perry et al., 1999).

Regarding GAS, to which the STAT1 homodimer binds in genes responsive to Type II interferon, a consensus sequence, nnnsantccgGGAAntgnsn (SEQ ID NO:3; capital letters denote core sequence; underlines denote high conservation), from many selected binding sequences was identified (Horvath et al., 1995).

In the instance where Type I interferon or Type II interferon is the extracellular ligand signal, a preferred combination of transcriptional control elements is an interferon responsive chimeric promoter in which an ISRE and/or GAS controls a SV40 minimal promoter operatively linked to a nucleotide sequence encoding a first reporter gene product as a first measurable tag.

When the extracellular ligand is TNFα, a preferred combination of transcriptional control elements is a TNF-α-responsive chimeric promoter in which repeats (i.e., 5× tandem repeats; SEQ ID NO:11) of the NFκB recognition site controls a SV40 minimal promoter operatively linked to a nucleotide sequence encoding a first reporter gene product.

When the extracellular ligand is erythropoietin (EPO), a preferred combination of transcriptional control elements is an EPO-responsive chimeric promoter in which repeats of the signal transducer and activator of transcription #5 (STAT5) sequence (5× tandem repeats is tcgagTTC-GAAGAAaacTTCTTGGAAgaTTCCTGGAgcTTCTAG GAAgaTTCCGGGAA (SEQ ID NO:4), where the sequence in capital letters represent variants of the STAT5 consensus sequence), through which EPO signals from its cell surface receptor to the nucleus, controls a SV40 minimal promoter operatively linked to a nucleotide sequence encoding a first reporter gene product.

The first reporter gene product (also known herein as a first measurable tag), whose level is a measure of the presence and/or the level of an extracellular ligand that activates the signal transduction activity of a cell surface protein or pattern recognition receptor, may be RNA or protein, as long as it is readily detectable, although it is preferably a protein. For instance, luciferases, such as firefly luciferase, *Renilla* luciferase, Gaussia luciferase and Metridia luciferase, enhanced green fluorescent protein (EGFP) and jellyfish aequorin are most preferred embodiments of reporter gene products (measurable tags) in the cell according to the present invention. In the case of the enzyme firefly luciferase (deWet et al., 1987) and other luciferases, and jellyfish aequorin (Rider et al., 2003), the result of its enzymatic activity, light, is detected and measured using a luminometer, whereas in the case of EGFP, a fluorescence activated cell sorter or analyzer (FACS) can be used at an appropriate wavelength to detect and quantify the amount of EGFP expressed in a cell. The distribution curve of the amount of luciferase, aequorin or EGFP expressed in a sample of cells will be determined by the amount of ligand to which the cell is exposed in the immediate external environment surrounding the cell. Non-limiting examples of other suitable reporter gene products include dsRED, chloramphenicol acetyl transferase (CAT) (Alton et al., 1979) other enzyme detection systems, such as β-galactosidase, bacterial luciferase (Engebrecht et al., 1984 and Baldwin et al. 1984), alkaline phosphatase (Toh et al. 1989 and Hall et al. 1983), and bacterial or humanized β-lactamase (Zlokarnik et al., 1998).

The second reporter gene product (also known as the second measurable tag), whose level is a measure of the level of the ligand, expressed together with the second reporter gene product (and on a separate cistron from the same promoter) and secreted into the immediate external environment surrounding the cell, and which ligand is capable of activating the signal transduction activity of a cell surface protein/receptor or a pattern recognition receptor. The second reporter gene product can be any of those disclosed above with regard to the first reporter gene product except that the first and second reporter gene products must be different from each other such that one reporter gene product can be independently measured in the presence of the other reporter gene product, and vice versa. The term "cistron" is intended to have the meaning commonly understood in the art as a segment of DNA coding for a single polypeptide but expressed from the same set of one or more transcription control elements (i.e., promoter) as the second reporter gene product.

When the cell is to be used to assay for neutralizing antibodies to a ligand antagonist/antibody (e.g., TNFα antagonists such as Eubrel, Infliximab, Adalimumab, Etanercept, etc.), the cell would further carry a third construct which includes a segment encoding a third reporter gene product (third measurable tag) driven by a third set of one or more transcription control elements different from the first and second set of transcription control elements in the first and second constructs. This third reporter gene product is expressed together with a ligand antagonist (on a separate cistron driven from the same transcription control elements/ promoter) and whose level is a measure of the level of expressed ligand antagonist. The ligand antagonist is the expressed and secreted into the immediate external environment surrounding the cell along with the ligand expressed from the second construct. The level of measurable ligand activity is a measure of the amount of neutralizing antibodies to the ligand antagonist that block the ligand antagonist from inhibiting the signaling activity of the ligand. The third reporter gene product can be any of those disclosed above with regard to the first and second reporter gene products, including preferably a CBG68Luc reporter gene, except that the third reporter gene product and the first and second reporter gene products must each be different such that each reporter gene product can be independently measured in the presence of the other two.

In the case of extracellular ligands that inhibit cell proliferation, induce apoptosis, or induce receptor down-regulation, the expression of the ligand is controlled by a set of one or more transcription control elements that is inducible (i.e., no expression unless an inducer is present). This would prevent the undesirable inhibitory activity of the extracellular ligand while the cell is growing or before the cell is ready for use in a cell-based assay. Another instance in which inducible transcription control elements are desirable for expressing the ligand is when the cell is used in a cell-based assay where only the level of the extracellular ligand in a sample, without any such ligand being produced from the second set of one or more transcription control elements, is sought to be determined rather than the level of neutralizing antibodies to the extracellular ligand. In the case that a ligand antagonist is to be expressed in a ligand antagonist is to be expressed in a third construct, the expression of the ligand antagonist is preferably controlled by a set of one or more transcription control elements that is inducible.

Inducible promoters and other transcriptional control elements, some of which are disclosed above, are well-known in the art. A preferred well known inducible transcriptional control element for use in controlling the expression of the ligand and a reporter gene product is a tetracycline-responsive element from the Tet-On/Tet-Off gene expression system (such as provided by Clontech Laboratories, Inc., Palo Alto, Calif.). This element, to which a reverse tetracycline repressor (rTetR; a mutated version of the tetracycline repressor) attaches, thereby inhibiting transcription from the Tet-On construction, is placed upstream of preferably a minimal promoter, such as the cytomegalo virus (CMV) immediate early minimal promoter. In the presence of an inducer, e.g., tetracycline or doxycycline, the mutated version of the TetR (rTetR) becomes a reverse tetracycline-controlled transactivator (rtTA) and binds to the TRE allowing transcription to start.

In another embodiment, the inducible promoter is a Tet-Off promoter in which the TetR binds to the TRE, silencing transcription in the presence of tetracycline or doxycycline. Following removal of tetracycline or doxycycline, the tetracycline-controlled transactivator (tTA) binds to the TRE, thereby activating transcription.

Figure 3:
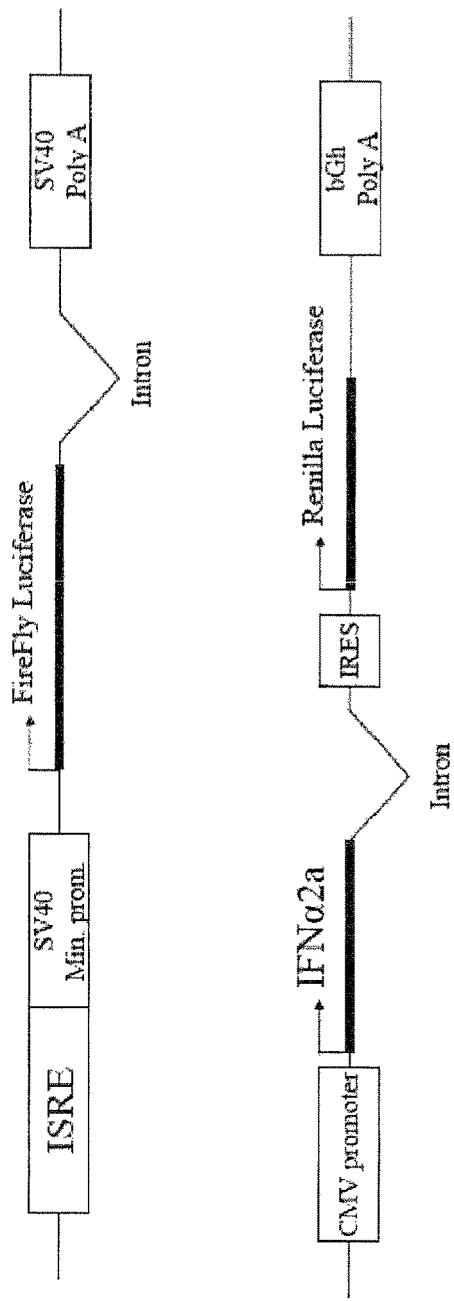
FIG. 3 is a schematic illustration of two separate constructs, an ISRE/SV40 minimal promoter driving the expression of the firefly luciferase reporter gene and a cytomegalovirus (CMV) promoter driving the expression of both interferon α2a (IFNα2a) and the *Renilla* luciferase reporter gene.

One embodiment of the cell according to the present invention is derived from the human pro-monocytic cell line U937 transfected with the firefly luciferase reporter gene controlled by an interferon responsive chimeric promoter containing a SV40 minimal promoter and the ISRE from the ISG 15 gene as described previously in WO 2004/039990 and US 2004/023517, which are incorporated herein by reference and shown in FIG. 3. These cells were then transfected with the 5991 bp pIRES/IFNA2/hRL vector (SEQ ID NO:5) which comprises the coding sequence of human IFN α2a gene (nucleotides 1-586 of SEQ ID NO:5), the IRES (Internal Ribosome Entry Site; SEQ ID NO:6) of cytomegalovirus (CMV), together with the coding sequence of *Renilla* luciferase reporter gene (nucleotides 1532-2484 of SEQ ID NO:5), under the control of a constitutive CMV promoter (nucleotides 5282-5991 of SEQ ID NO:1) as shown in FIG. 3. Thus, this construction allows the primary RNA transcript to be translated into two distinct native proteins (IFNα2a and *Renilla* luciferase) so as to preserve the tertiary structure of the human IFNα2a protein and hence its recognition by anti-IFNα antibodies.

Figure 4:
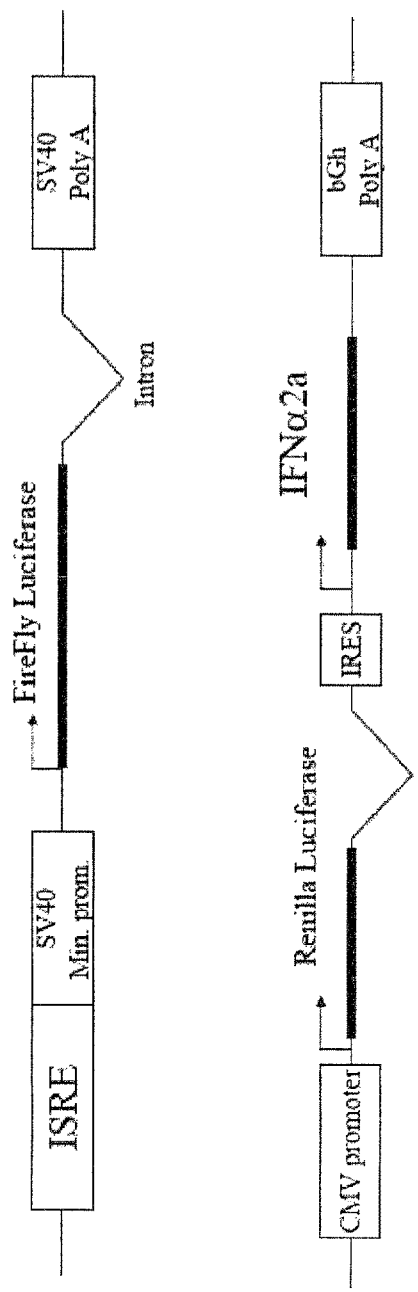
FIG. 4 is a schematic illustration of two separate constructs, an ISRE/SV40 minimal promoter driving the expression of firefly luciferase gene reporter and the minimal immediate early promoter of cytomegalovirus (CMV) driving the expression of both interferon α2a (IFNα2a) and *Renilla* luciferase gene reporter, but with the order of IFNα2a and *Renilla* luciferase expression reversed from that shown in FIG. 3.

In a preferred embodiment of the cell of the present invention, the *Renilla* luciferase reporter-gene was cloned upstream of the IRES and the human IFNα2a gene (FIG. 4) in order to increase the low levels of *Renilla* gene expression observed when the human IFNα2a gene, or other human type I IFN genes (i.e., IFNβ), was cloned upstream of the *Renilla* luciferase reporter gene.

Figure 5:
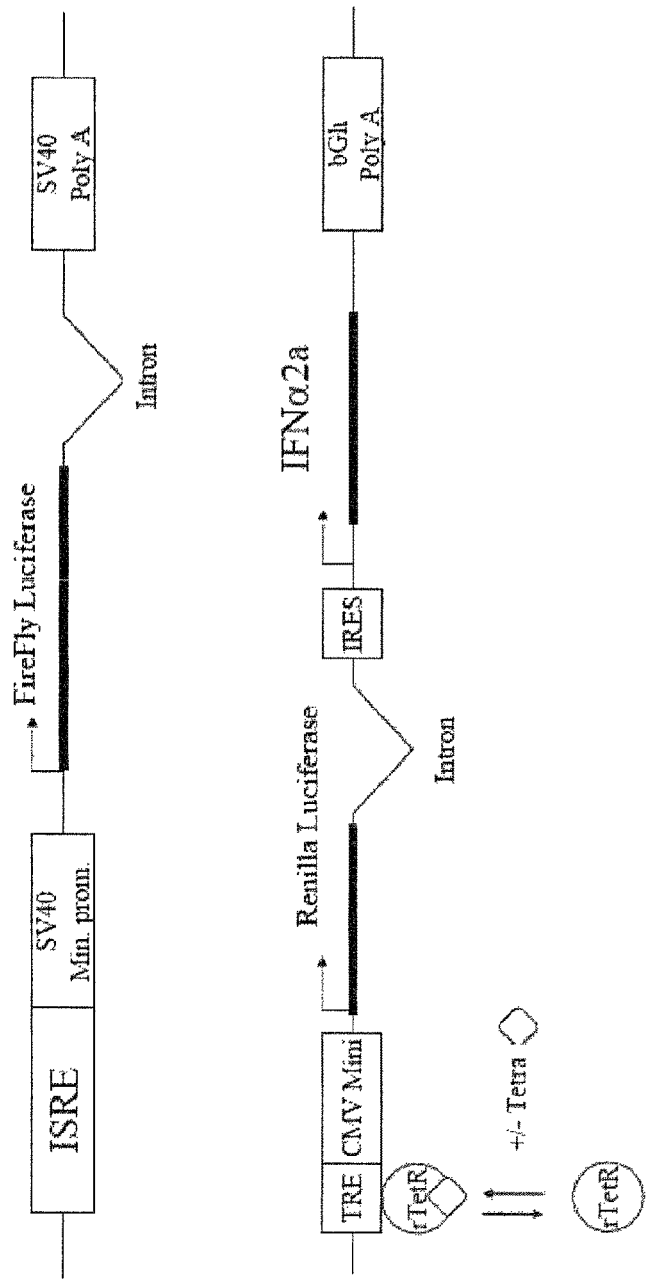
FIG. 5 is a schematic illustrations of two separate constructs, an ISRE/SV40 minimal promoter driving expression of the firefly luciferase reporter gene, and a tetracycline (Tet)-responsive element (TRE)/the CMV immediate early minimal promoter driving the expression of the *Renilla* luciferase reporter gene and IFNα2a (Tet-On). In the absence of tetracycline or doxycycline, the reverse Tet repressor (rTetR) binds to the TRE, silencing transcription. Also depicted is the binding of the reverse tetracycline transactivator (rtTA) to the TRE following addition of tetracycline or doxycycline leading to activation of transcription.

In a second preferred embodiment of the cell of the present invention, the *Renilla* luciferase reporter-gene and the human IFNα2a gene were expressed under the control of an inducible promoter in order to prevent continued expression of human type I IFNs from inhibiting cell proliferation and hence preventing cultivation of the transfected cell line. Thus, the *Renilla* luciferase reporter gene and the human IFNα2a gene, were expressed under the control of a CMV promoter (FIG. 5), the expression of which is induced in the presence of doxycycline or tetracycline (Tet-On).

Figure 6:
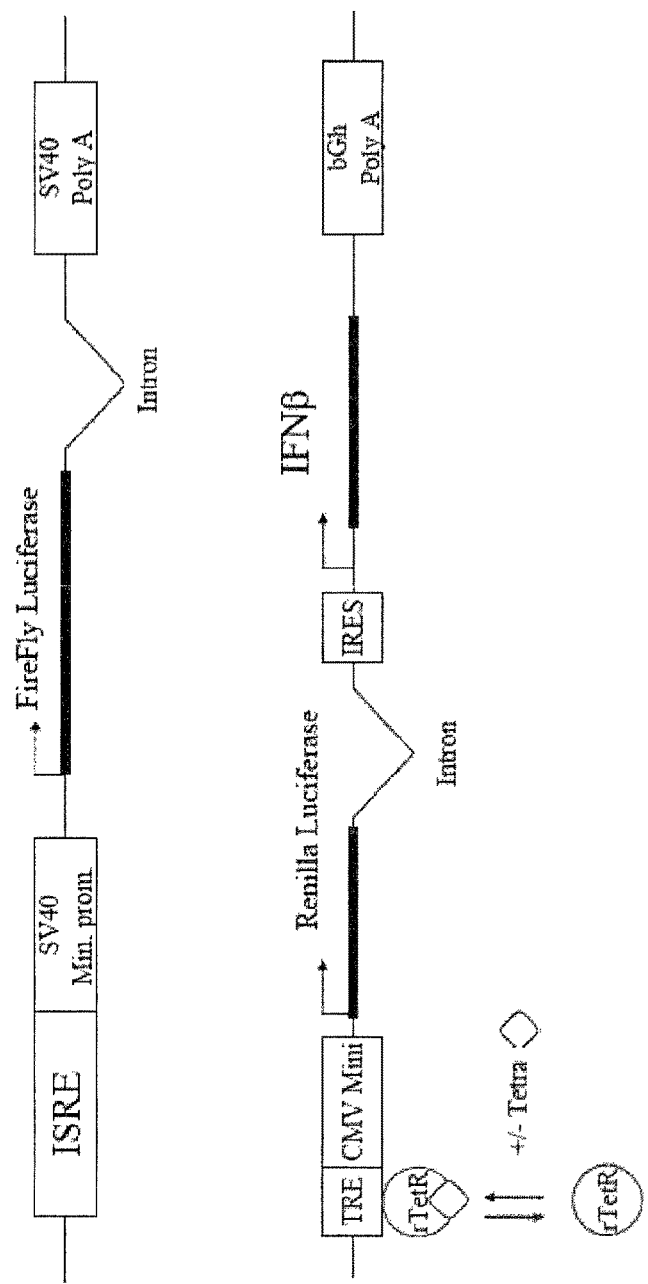
FIG. 6 is a schematic illustrations of two separate constructs; an ISRE/SV40 minimal promoter driving expression of the firefly luciferase reporter gene, and a tetracycline (Tet) responsive element (TRE)/CMV immediate early minimal promoter driving the expression of the *Renilla* luciferase reporter gene and IFNβ (Tet-On).

In a third preferred embodiment cell of the present of the invention, the *Renilla* luciferase reporter-gene and the human IFNβ1a gene, are expressed under the control of a Tet-On CMV promoter (FIG. 6).

Figure 7:
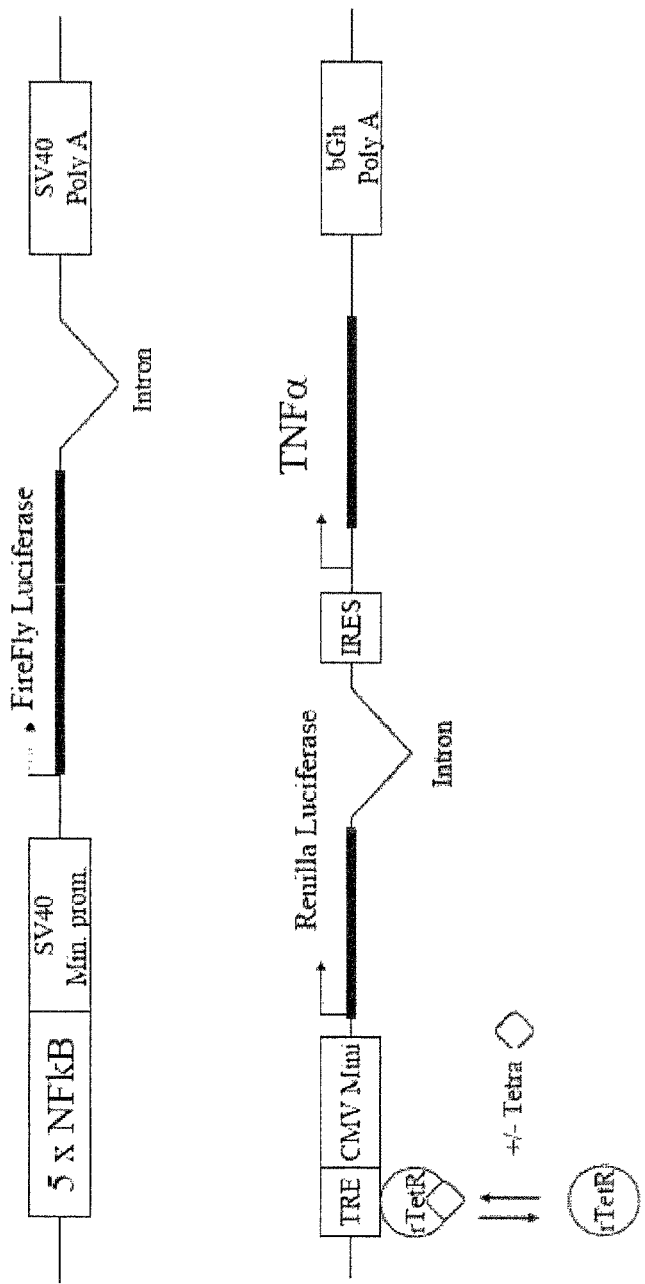
FIG. 7 is a schematic illustration of two separate constructs for a gene reporter assay for anti-TNFα NAb, a 5× tandem repeat of the canonical NFκB recognition site/SV40 minimal promoter driving the expression of firefly luciferase gene reporter, and a Tet-responsive element (TRE)/CMV immediate early minimal promoter driving the expression of both TNFα and the *Renilla* luciferase gene reporter (Tet-On).

In a further embodiment of the cell of the present invention, the *Renilla* luciferase reporter gene and the human TNFα gene, are expressed under the control of a tet-on CMV promoter (FIG. 7). The use of an inducible promoter is essential for the expression of TNFα, the uncontrolled production of which would induce apoptosis in the TNFα-sensitive host cells. The sequence of the 5× tandem repeats of the canonical NFκB recognition site used in the other construct in FIG. 7 to drive the expression of firefly luciferase in combination with a SV40 minimal promoter is SEQ ID NO:11.

Figure 9:
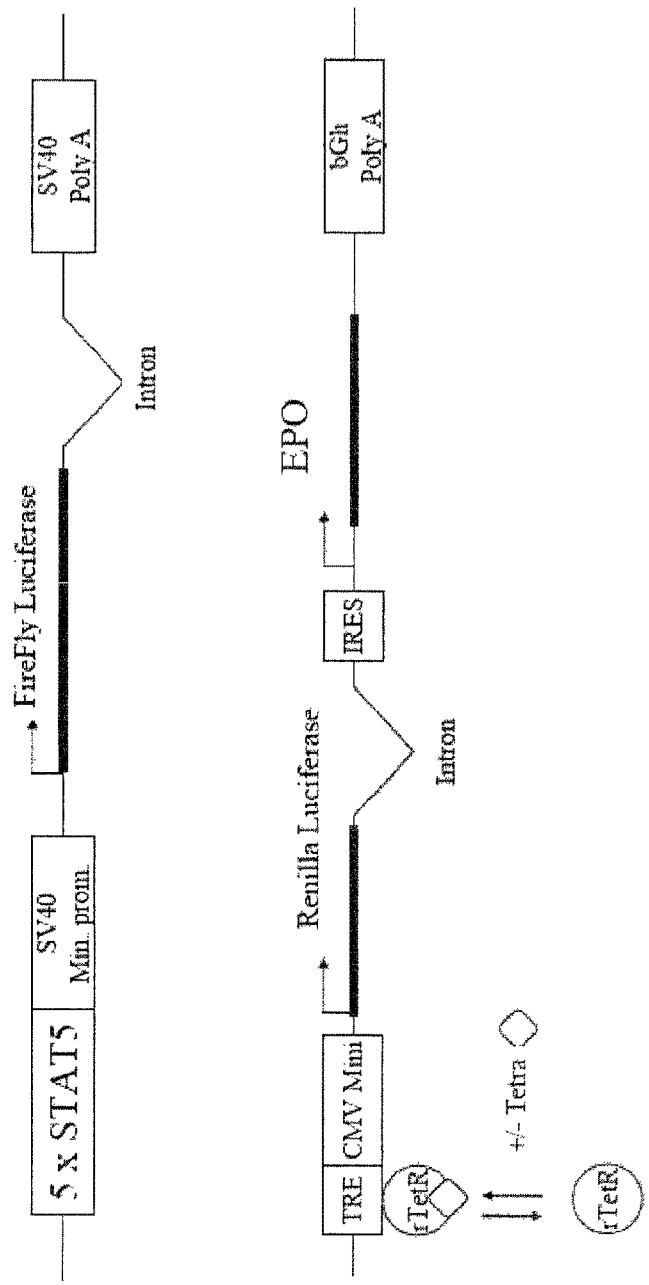
FIG. 9 is a schematic illustration of two separate constructs for a gene reporter assay for anti-erythropoietin (EPO) NAb, a 5× tandem repeat of the signal transducer and activator of transcription #5 (STAT5)/SV40 minimal promoter driving the expression of the firefly luciferase reporter gene, and a Tet-responsive element (TRE)/CMV immediate early minimal promoter driving the expression of both EPO and the Renilla luciferase reporter gene (Tet-On).

In still a further embodiment of the cell of the present invention, the *Renilla* luciferase reporter gene and the human erythropoietin (EPO) gene, are expressed under the control of a Tet-On CMV promoter (FIG. 9). The use of an inducible promoter is essential for the expression of EPO, the continuous production of which would cause downregulation of EPO-specific receptors on the EPO sensitive host cells.

Figure 8:
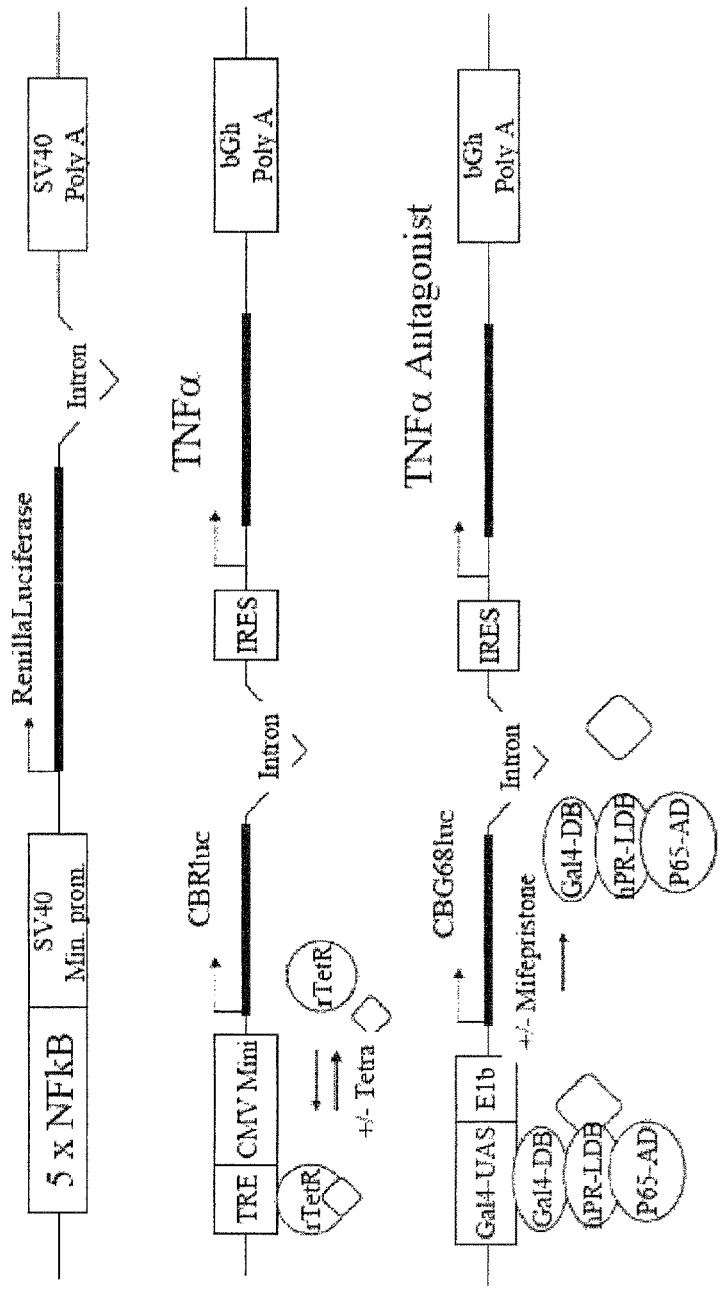
FIG. 8 is a schematic illustration of three separate constructs for a gene reporter assay for anti-TNFα antagonist NAbs: a 5× tandem repeat of the canonical NFκB recognition site/SV40 minimal promoter driving the expression of *Renilla* luciferase reporter gene; a Tet-responsive element (TRE)/CMV immediate early minimal promoter driving the expression of both TNFα and the CBRLuc reporter gene (Tet-On); and a chimeric mifepristone inducible promoter driving transcription of the TNFα antagonist and the CBG68Luc reporter gene. The mifepristone-inducible chimeric promoter consists of the GAL4-UAS and the TATA sequence from the Adenovirus E1b minimal promoter that is transcriptionally silent in the absence of activation. The Gal4 DNA binding domain which binds the regulatory protein to the GAL4-E1b promoter and the truncated human progesterone receptor ligand binding domain (hPR-LBD) which undergoes conformational change when it binds the progesterone antagonist mifepristone are expressed from a minimal TK promoter on the vector. Thus, upon addition of mifepristone, the antagonist binds to the hPR-LBD region of the vector causing a conformational change in the regulatory protein resulting in transcription of the TNFα antagonist and the CBG68Luc reporter gene.

In yet a further embodiment of the cell of the present invention, the *Renilla* luciferase reporter gene is expressed under the control of chimeric promoter consisting of a 5× tandem repeat of the canonical NFκB recognition site/SV40 minimal promoter. In addition, the TNFα and the CBRLuc reporter gene are both expressed under the control of a Tet-responsive element (TRE)/CMV immediate early minimal promoter (Tet-On) as a second construct, and the TNFα antagonist of interest and the CBG68Luc reporter gene are expressed in a third construct under the control of a different inducible promoter such as the chimeric mifepristone inducible promoter. In this system, the GAL4-UAS and the TATA sequence are expressed from the Adenovirus E1b minimal promoter that is transcriptionally silent in the absence of activation. The Gal4 DNA binding domain, which binds the regulatory protein to the GAL4-E1b promoter, and the truncated human progesterone receptor ligand binding domain (hPR-LBD), which undergoes conformational change when it binds the progesterone antagonist mifepristone, are expressed from a minimal TK promoter on the vector. Thus, upon addition of mifepristone, the antagonist binds to the hPR-LBD region of the vector, causing a conformational change in the regulatory protein resulting in transcription of the TNFα antagonist and the CBG68Luc reporter gene (FIG. 8).

In order to make the cell according to the present invention a one time use cell that cannot be propagated for further use, the cell (after having been transformed/transfected with the first, second, and optionally, third DNA construct) is treated with an anti-mitotic or pro-apoptotic agent so as to acquire the property that it will maintain the ligand-specific signal transduction activity for at least about 1 hour but no more than about 30 days at a temperature above freezing before losing the signal transduction activity and undergoing cellular death.

One preferred embodiment of the present invention is where the anti-mitotic or pro-apoptotic agent is γ-radiation and the cell has been treated by irradiating with γ-radiation at an intensity and for a sufficient time such the irradiated cell maintains the signal transduction activity of a cell surface protein/receptor or a pattern recognition receptor for a period of at least about 1 hour, preferably 7 days but no more than 30 days at a temperature above freezing following irradiation, after which period of time the irradiated cell immediately undergoes cellular death (i.e., apoptosis).

It is known that γ-irradiation at a high dose causes a cell to lose its signal transduction activity. Irradiation at a somewhat lower dose causes a cell to cease replication and undergo cellular death. The present inventors previously discovered that it is possible to determine a dose which inhibits replication but still allows a cell to maintains its signal transduction activity for a period of time before undergoing cell death. For example, γ-irradiation at about 9 Grays allows U937 cells to retain signal transduction activity for 14 days, after which the cells undergo cell death. However, during those 14 days, the signal transduction activity in response to, for example, Type I interferon that is being assayed functions as well as in a non-irradiated control. Thus, by irradiating a cell with γ radiation, the treated cell has a 14-day shelf life, but which becomes inactive (undergoes cellular death) after a period of about 14 days so that it cannot be maintained and reproduced by an end user. The dose of γ-irradiation required will vary as a function of the particular cell line employed but this can be determined with only routine experimentation based on the guidance in WO 2004/039990 and US 2004/023517.

The dose (intensity and duration) of γ radiation to which the transformed cell is treated is preferably about 6 to 12 Grays (Gy). As the experiments in WO 2004/039990 and US 2004/023517 demonstrate, the temperature above freezing, at which the cell is kept or stored, affects the shelf-life of the cell. Preferably, this temperature is room temperature, which advantageously maintains maximum interferon sensitivity while providing for ease of storage and shipping of the commercial one time use cell.

A second preferred embodiment of the present invention is where the cell (after having been transformed/transfected with the first, second, and optionally, third DNA construct) is treated with an anti-mitotic or pro-apoptotic chemical agent such as vinblastin, 5-fluorouracil (5-Fu), cisplatin or an anti-tumor intercalating agent (i.e., mitomycin C) in a sufficient amount and for a sufficient time such that the treated cell maintains the signal transduction activity of the cell surface protein or pattern recognition receptor for a period of at least about 1 hour but no more than about 30 days at a temperature above freezing following treatment with the agent, after which period of time the treated cell immediately undergoes cellular death. An anti-mitotic or pro-apoptotic agent will affect a treated cell when it begins to replicate, such as for example by preventing spindle formation, thereby inducing apoptosis and killing the cell. Thus, cells which have been treated with an anti-mitotic or pro-apoptotic agent, such as transformed human promonocytic cells, will have a shelf life of about 24 hours during which the signal transduction assay can be conducted and after which period of time the cells will die. It will be appreciated that a cell having only a 24 hour shelf life is not desirable from a commercial standpoint. In order to extend the shelf life, the treated cells may be immediately frozen, in which state they will have a much longer shelf life, depending upon the manner of freezing and thawing. Once thawed, however, they must be used within 24 hours, after which they will undergo cellular death (i.e., apoptosis).

It should be understood that conventional wisdom is that cryopreservation of cells requires a special freezing and thawing process (and equipment) in which the cells are frozen at a rate of 1° C. per minute until it reaches −80° C. or liquid nitrogen temperatures of about −200° C., where it may be stored indefinitely, and after which it must be thawed very rapidly. Often, dimethyl sulfoxide (DMSO) or another cryopreservative is also used in order to help protect the cells. As most laboratories do not have storage facilities at −200° C. or even −80° C., it would be useful to allow freezing of the cells to occur at −20° C. However, it is known that cell viability is poor when cells are frozen at −20° C. and then thawed. It was previously found by the present inventors that DMSO will protect the cells even when frozen at −20° C. without any special freezing or thawing techniques or equipment. While glycerol, a known cryopreservative compound, will protect cells at −20° C., there is the possibility that it may prevent protein ligands from interacting with surface receptors at the high percentage (50%) of glycerol conventionally used for cryopreservation. However, a low percentage of glycerol (much less than the 50% conventionally used) can be used. DMSO does not have this disadvantage. DMSO can thus protect cells frozen at −20° C. without any special freezing or thawing techniques or equipment being required and without adversely affecting their sensitivity to IFN. After treating with an anti-mitotic or pro-apoptotic agent, a cell may achieve a long shelf life even at standard freezer temperatures of −20° C. if further treated with DMSO and that once thawed such a cell will remain active, i.e., for signal transduction assays used for determining the amount of ligand or neutralizing antibodies to the ligand or to an anti-ligand antibody, for approximately 24 hours until it undergoes apoptosis as a result of being treated with an anti-mitotic and pro-apoptotic agent. Any anti-mitotic or pro-apoptotic agent which kills cells during the process of replication by inducing apoptosis, such as γ-radiation and chemical agents such as vinbastin, 5-FU, cisplatin, doxorubicin, or an anti-tumor intercalating agent (i.e., mitomycin C) can be used for this purpose as it would be expected that the cells will remain biologically active during a quiescent period and until such time the treated cells start to die.

The treated transformed cell (transformed with the first, second, and optionally, third DNA construct) is frozen at a temperature and under conditions such that it will resume signal transduction after thawing. While the cell is preferably frozen at a temperature between $-20°$ C. and $-200°$ C., more preferably at $-80°$ C., cells may be subsequently stored at $-20°$ C., a commonly available freezer temperature in almost all laboratories, it is intended that other suitable temperatures for cryopreservation of cells, such as the liquid nitrogen temperature of about $-200°$ C., be encompassed. It is further preferred that the treated transformed cell be resuspended in a solution containing a cryopreservative before freezing the cell. Dimethyl sulfoxide (DMSO) is the preferred cryopreservative although other suitable cryopreservatives which have a high bonding affinity to water, such as ethylene glycol, polyethylene glycol, propylene glycol, glycerol, butane diol, propanediol, and formamide, may be used so long as they do not interfere with the use of the cell after thawing. When DMSO is used alone as the cryopreservative, the solution containing DMSO preferably contains about 10% DMSO. More preferably, 2.5% DMSO is used in combination with 10% glycerol as the cryopreservative.

The cell according to the present invention is preferably a mammalian or avian cell, more preferably a human cell, and most preferably a human promonocytic cell. A preferred human promonocytic cell carrying the ISRE-luc vector containing the firefly luciferase gene reporter construct is a PIL5 cell. Other preferred cell lines include, but are not limited, to human myeloid (i.e., U266R), human T-cell lymphoma (i.e., Jurkatt), human breast adenocarcinoma (i.e., MCF7) cell lines and mouse lymphoma (i.e., L1210) and mouse erythroid leukemia cell lines. The cell is treated to make a commercial cell line that has the commercially desirable properties of a sufficient shelf life for the purpose of the assay and of being a one time use cell that cannot be propagated for possible further use. Preferably, the cell is treated either 1) by irradiating with 6 to 12 Gy of γ radiation, more preferably about 9 Gy, and storage at room temperature for up to 14 days after irradiation or 2) by exposure to an anti-mitotic or pro-apoptotic agent, such as vinblastin, cisplatin, or 5-fluorouracil, most preferably vinblastin, for 10 minutes at $37°$ C. prior to resuspending in a solution containing 40% fetal bovine serum (FBS) and 2.5% DMSO+ 10% glycerol and freezing at $-80°$ C.

In order to optimize the method of obtaining a cell with an indefinite shelf life during frozen storage, but which will die approximately 24 hours after being thawed (once thawed, however, the product has excellent sensitivity, and precision as well as selectivity), the parameters which can be varied in the course of such optimization include:

1) Concentration of FBS. Besides FBS, most any serum could be used as it acts as a toxic sink to protect the cells from toxins, such as while being thawed or while being treated with an anti-mitotic or pro-apoptotic agent. The concentration of FBS can cause the results to vary.

2) Time is a variable. The amount of time of exposure to an anti-mitotic or pro-apoptotic chemical agent, such as vinblastin, before the cells are centrifuged out and washed to remove the agent (i.e., vinblastin).

3) Using vinblastin as a non-limiting example, the formulation of the vinblastin makes a difference. Presently, soluble vinblastin in a proprietary prebuffered formulation sold by Eli Lilly under the name Velbe in France is preferably used. A different formulation may require slightly different combination of parameters.

4) The concentration of vinblastin.

5) Cell concentration during the vinblastin treatment.

6) The amount of cryopreservative or combination of cryopreservatives.

All of these parameters can be varied empirically and the results after freezing tested for sensitivity and precision, assuming that the cells stay alive for approximately 24 hours after being thawed. This can be readily determined by one of ordinary skill in the art without undue experimentation, particularly in view of the guidance provided in the experiments shown in FIGS. 11-24 for PIL5 cells in WO 2004/039990 and US 2004/023517, in order to arrive at a product having substantially the same sensitivity as the untreated live cells for a period of at least one hour, preferably 8-24 hours, following thawing but having a viability of no more than 30 days, preferably no more than 14 days, more preferably no more than 5 days, most preferably no more than 3 days.

Exemplified below are protocols for preparation of microtiter assay plates and ampoules/vials of PIL5 cells (as model cells) treated with the anti-mitotic and pro-apoptotic agent 1 μg/ml vinblastin for 10 minutes at $37°$ C. prior to frozen storage at $-20°$ C. and thawing at a later time for purposes of conducting the assay.

Preparation of Microtiter Assay Plates

1. PIL5 cells at a concentration of about $2\times10^5$ to $7\times10^5$ cells/ml in RMPI 1640 medium with 10% fetal bovine serum (FBS) are treated with a fresh solution of 1 μg/ml vinblastin (commercially available from Eli Lilly under the pre-buffered formulation VELBE), diluted from 1 mg/ml in $H_2O$, for 10 minutes at $37°$ C. in an atmosphere of 5% $CO_2$ in air. A $CO_2$ incubator can be used for convenience.

2. The PIL5 cells are centrifuged at 800×g for 10 minutes at $4°$ C., and washed once with the same volume of RPMI 1640 medium with 10% FBS to remove the vinblastin.

3. The PIL5 cells are re-suspended at a concentration of $2\times10^7$ cells/ml in RMPI 1640 medium with 40% fetal bovine serum (FBS) and 2.5% dimethylsulfoxide+10% glycerol.

4. The cell suspension is dispensed into the wells of a flat-bottom micro-plate to give 300,000 cells per well (equivalent to 25 μl of cell suspension per well).

5. The micro-plate is frozen at $-80°$ C. in an aluminum bag sealed under vacuum with the cover uppermost.

6. The micro-plates can be subsequently stored for limited periods at $-20°$ C. until use.

Alternatively, PIL5 cells at a concentration of 2×107 cells/ml in RMPI 1640 medium with 40% fetal bovine serum (FBS) and 2.5% dimethylsulfoxide+10% glycerol can be frozen at $-80°$ C. or $-200°$ C. in a single or multiple cryopreservation vials. Immediately prior to use the viale is thawed rapidly and the cells distributed into one or more microtiter plates. Vials may also be prepared containing sufficient cells for half or a quarter of a microtiter plate as required.

Preparation of Cryopreservation Ampoules/Vials

1. PIL5 cells at a concentration of about $2\times10^5$ to $7\times10^5$ cells/ml in RMPI 1640 medium with 10% fetal bovine serum (FBS) are treated with a fresh solution of 1 μg/ml vinblastin (commercially available from Eli Lilly under the prebuffered formulation VELBE), diluted from 1 mg/ml in H₂O for 10 minutes at 37° C. in an atmosphere of 5% $CO_2$ in air. A $CO_2$ incubator can be used for convenience.

2. The PIL5 cells are centrifuged at 80×g for 10 minutes at 4° C., and washed once with the same volume of RPMI 1640 medium with 10% FBS to remove the vinblastin.

3. The PIL5 cells are re-suspended at a concentration of $2 \times 10^7$ cells/ml in RMPI 1640 medium with 40% fetal bovine serum (FBS) and 2.5% dimethylsulfoxide+10% glycerol.

4. The cell suspension (1 ml) is dispensed into a cryopreservation vial and frozen at −80%.

5. The cryopreservation vial can be subsequently stored at −20° C. for limited periods until use.

The present invention also provides a method of using the cell according to the present invention for determining the level in a sample of an extracellular ligand that initiates a ligand-specific signal at the nucleus (i.e., by signal transduction from a cell surface receptor or from a pattern recognition receptor) or the level of neutralizing antibodies either against the extracellular ligand or an antagonist against the extracellular ligand, or the level of a soluble form of the ligand receptor. This method involves incubating the cell of the present invention in a mixture with a sample in which the level of the extracellular ligand or the neutralizing antibody is sought to be determined. The level of the first measurable tag (first reporter gene product, such as firefly luciferase in the embodiments shown in the drawings) in the mixture is determined relative to the level of the first measurable tag in the absence of the sample to calculate the level in the sample of the extracellular ligand or neutralizing antibody.

The present invention also provides a means of detecting the presence of residual drug in the sample to be tested for the presence of anti-drug NAbs. The presence of residual drug can render the results of neutralization assays uninterpretable. In the case of patients treated with a biopharmaceutical drug which is, for instance, a recombinant form of a cytokine such as IFNβ or a growth factor such as EPO, the presence of the drug (IFNβ or a growth factor) in the sample (serum or other biological fluid) to be assayed for the presence of anti-cytokine or anti-growth factor NAbs can be determined using the method of the present invention prior to carrying out the neutralization assay according to the present invention by simply first incubating the sample with the assay cell of the present invention for an appropriate time (3 to 6 hours). Activation of firefly luciferase, in the absence of addition of tetracycline or doxycycline, will indicate the presence of residual drug. The degree of activation of the firefly luciferase will allow the level of residual drug to be quantified. Residual drug can then be removed by the use of an appropriate procedure. For example in the case of IFNβ, the drug can be separated from any anti-IFN antibodies present in the sample by the use of a molecular sieve with a 20 to 30 kDa cut-off or an anti-IFNβ affinity column. Alternatively, anti-IFN NAbs can be removed from the sample using a protein-A or protein G affinity column.

The sample can then be assayed for the presence of anti-IFN NAbs following activation of the ligand-*Renilla* luciferase construct in the presence of tetracycline or doxycycline.

In the case of TNFα antagonists such as Infliximab, a chimeric antibody, Adalimumab, a fully human antibody, or Etanercept, an IgG1FC-TNFp75 receptor fusion protein, the presence of residual drug can again interfere with the detection of NAbs against the TNFα antagonist. The presence of residual drug in the sample can be detected using the one-step assay method according to the present invention simply by incubating the serum sample with the assay cells in the presence of tetracycline or doxycycline prior to activation of the inducible Infliximab construct. In this construct, the nucleic acid encoding Infliximab is under the control of an inducible promoter different from the Tet-On or Tet-Off promoter. For example, a mifepristone-regulated promoter can be employed such as that commercialized by Invitrogen (Carlsbad, Calif.). In this system, a chimeric promoter, consisting of the GAL4-UAS and the TATA sequence from the Adenovirus E1b minimal promoter, is transcriptionally silent in the absence of activation. The Gal4 DNA binding domain, which binds the regulatory protein to the GAL4-E1b promoter, and the truncated human progesterone receptor ligand binding domain (hPR-LBD), which undergoes conformational change when it binds the progesterone antagonist mifepristone, are expressed from a minimal TK promoter on the vector. Thus, upon addition of mifepristone, the antagonist binds to the hPR-LED region of the vector, causing a conformational change in the regulatory protein resulting in transcription from the GAL4-E1b promoter.

Thus, a reduction in the Tet-On regulated TNFα-induced *Renilla* luciferase signal, due to the production of endogenously expressed TNFα, following addition of a sample to the cells of the present invention, will indicate the presence of the TNFα antagonist in the sample to be assayed for the presence of anti-TNFα antagonist NAbs. The degree of reduction of the *Renilla* signal produced by endogenously expressed TNFα, will allow the concentration of the TNFα antagonist in the sample to be quantified. The TNFα antagonist can then be removed from the sample by an appropriate means. For example in the case of Infliximab, which is composed solely of kappa light chains, the drug can be removed from the sample to be assayed for anti-Infliximab NAbs using an anti-kappa affinity column. Alternatively, anti-Infliximab NAbs can be removed from the sample using a protein-A or protein G affinity column and then quantified using the "One-Step" assay method according to the present invention.

The sample which is assayed in the method according to the present invention is a biological fluid of a mammalian subject, preferably a human subject, in which the extracellular ligand or neutralizing antibodies are expected to be present, such as blood. Most preferably the sample is serum, saliva, bronchoaveolar lavage, or cerebrospinal fluid.

A preferred embodiment of the method according to the present invention is where the cell used in the assay is a cell treated with an anti-mitotic or pro-apoptotic agent frozen as described above, and which is then thawed, prior to use, within a period of time that the thawed cell maintains the ligand-specific signal transduction activity.

When the method according to the present invention is used for determining the level in a sample of an extracellular ligand that initiates a ligand-specific signal at the nucleus, the cell according to the present invention would need to have any endogenous production of the ligand by the cell itself to be negligible or absent. Since the ligand is expressed from a second set of one or more transcription control elements in the second DNA construct present in the cell, the expression of the ligand in this situation is controlled from an inducible set of one or more transcription control elements which is turned off so as to not interfere with the determination of the level of extracellular ligand in the sample itself.

When the method according to the present invention is used to determine the level in a sample of neutralizing antibodies either against the extracellular ligand or against an antagonist to the ligand, the ligand can be expressed from a constitutive promoter or from an inducible set of one or more transcription control elements. However, for the case of determining the level of neutralizing antibodies against a ligand antagonist (i.e., against Enbrel, Infliximab, etc., for TNFα as the extracellular ligand), the cell according to the present invention preferably includes an additional construct (i.e., third DNA construct) from which the ligand antagonist and a third different measurable tag are expressed. In this way, the cell according to the present invention would have all the necessary components of ligand, ligand antagonist and ligand-responsive expression of a reporter gene present in a single cell to assay for neutralizing antibodies in a sample. Such a cell would only require addition of an undiluted sample to initiate the assay (and the presence of substrate for the reporter-gene product).

Figure 10:
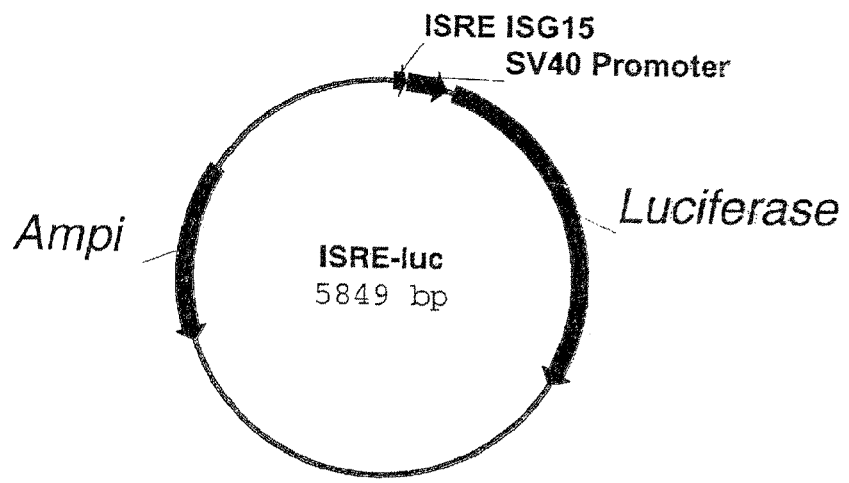
FIG. 10 shows a schematic representation of a luciferase reporter gene construct where luciferase expression is under the control of a chimeric promoter containing an interferon sensitive response element (ISRE) from the ISG15 gene and a minimal SV40 promoter.
Figure 11:
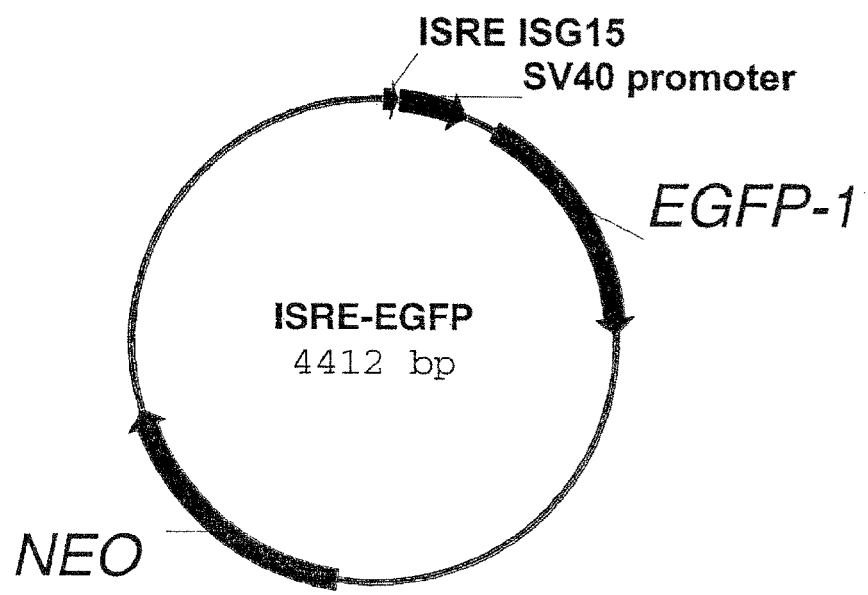
FIG. 11 shows a schematic representation of an enhanced green fluorescent protein (EGFP-1) reporter gene construct where EGFP-1 expression is under the control of a chimeric promoter containing an ISRE from the ISG15 gene and a minimal SV40 promoter.
Figure 12:
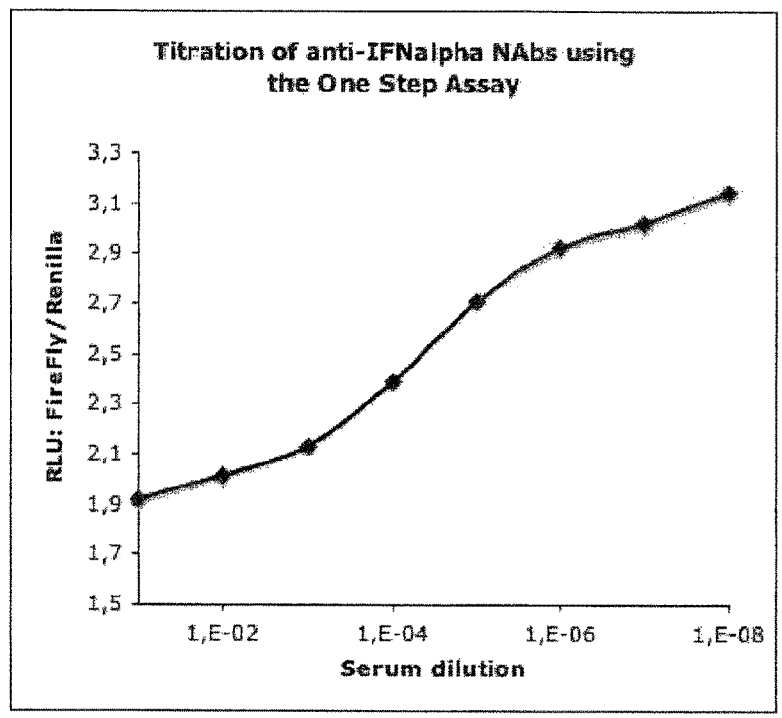
FIG. 12 is a graph showing the titration curve of anti-IFNα neutralizing antibodies using the method of the present invention.
Figure 13:
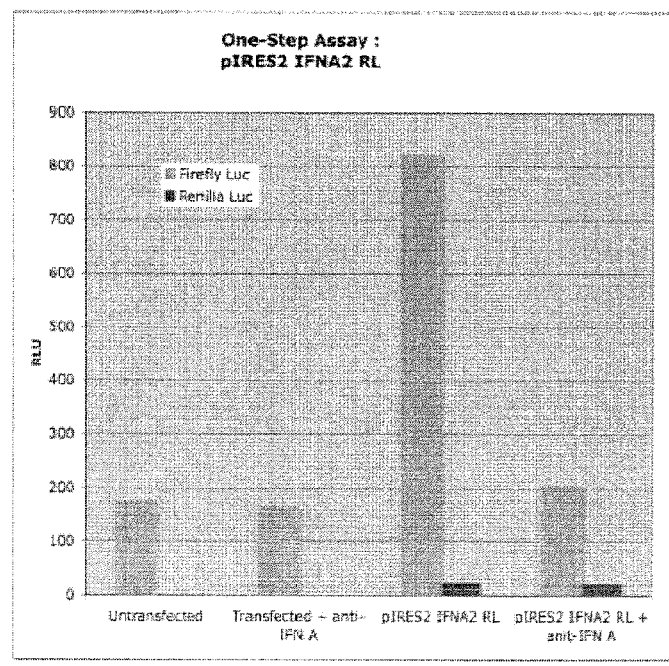
FIG. 13 is a graph of the relative luminescence units (RLU) observed in assaying for neutralizing antibodies to IFNα according to the method of the present invention in cells untransfected or transfected with the pIRES IFNA2 RL as the second DNA molecule.

When the method of the present invention is assaying for the level of a Type I interferon to determine either the titer of the Type I interferon as extracellular ligand or of neutralizing antibodies for Type I interferon, the first reporter gene product is preferably firefly luciferase, jellyfish aequorin, or enhanced green fluorescent protein (EGFP) and is preferably under the control of an interferon-sensitive chimeric promoter containing the ISRE from ISG15 and a minimal SV40 promoter. Examples of such reporter gene constructs are presented in FIGS. 9 and 10. FIG. 9 is a schematic representation of a luciferase gene reporter construct in an ISRE-luc vector (SEQ ID NO:7), where the ISRE from ISG15 (SEQ ID NO:2) is positioned at nucleotides 38-97 of SEQ ID NO:7, the SV40 minimal promoter is positioned at nucleotides 103-288 of SEQ ID NO:7, and the coding sequence of the luciferase reporter gene having the amino acid sequence of SEQ ID NO:8 is positioned at nucleotides 328-1980 of SEQ ID NO:7. Similarly, FIG. 10 is a schematic representation of a EGFP gene reporter construct in an ISRE-EGFP vector (SEQ ID NO:9), where the ISRE from ISG15 is positioned at nucleotides 30-89 of SEQ ID NO:9, the SV40 minimal promoter is positioned at nucleotides 95-290 of SEQ ID NO:9, and the coding sequence of the EGFP reporter gene having the amino acid sequence of SEQ ID NO:10 is positioned at nucleotides 358-1077 of SEQ ID NO:9.

The sample of serum (10 µl) to be tested for the presence of anti-ligand antibodies is added to the well of a 96-well plate containing 50,000 One-Step cells (cells according to the present invention) cells in 50 ml of RPMI 1640 medium containing 2% BFS and a suitable concentration of doxycycline in the range 1.0 ng/ml to 10.0 µg/ml, most preferably 1.0 µg/ml. The sample is incubated with the cells at 37° C. in an atmosphere of 5% $CO_2$ in air for a period ranging from 4 to 18 hours, most preferably 5 to 6 hours. The activities of the firefly luciferase and Renilla luciferase can then be determined sequentially following addition of 50 µl of the DUAL-GLOW luciferase assay reagent (Promega, Madison, Wis.). Thus, expression of the firefly luciferase can first be quantified using the Luciferase Assay Reagent II (Promega, Madison, Wis.). This reaction is then quenched and the Renilla luciferase reaction is initiated by addition of 50 µl of the STOP & GLO reagent (Promega, Madison, Wis.) to the same sample and expression of Renilla luciferase is quantified. Neutralization titer is determined from the level of expression of the firefly luciferase gene expressed in relative luminescence units (RLU) following addition of the anti-ligand antibody (FL2) relative to the level of expression in RLU of the Renilla luciferase (RL2) divided by level of expression of the firefly luciferase gene without addition of the anti-ligand antibody (FL1) relative to that of the Renilla luciferase (RL1). Thus, neutralization titre=FL2/RL2 divided by FL1/RL1. This titer can then be quantified relative to an anti-ligand NAb reference preparation of known titer. A titration curve of anti-INFα neutralizing antibodies using the present method is presented in FIG. 11.

An assay for the quantification of anti-IFN alpha NAbs is described herein that overcomes many of the limitations of conventional cell-based neutralization assays or other reporter-gene assays noted in the "Description of the Related Art" section. The assay is based on a cell that has been engineered to express and secrete IFNα2 and to express the Renilla luciferase reporter-gene transcribed from the same inducible promoter. The cell also contains the firefly luciferase reporter gene controlled by a chimeric IFN-responsive promoter. Expression of the Renilla reporter gene is strictly proportional to expression of IFNα2 and therefore allows IFN expression to be quantified with precision while expression of firefly luciferase allows IFN activity to be quantified. The presence of anti-IFNα NAbs in the immediate environment of the cell will neutralize a quantity of IFNα secreted from the cell proportional to the neutralizing capacity of the antibody, and thus prevent IFN from interacting with its specific cell-surface receptor. This will result in a corresponding reduction in the activity of IFNα and hence expression of the IFN-responsive firefly luciferase reporter gene, the activity of which can be quantified. The degree of reduction in the expression of the IFNα-responsive reporter gene in the presence or absence of the NAb sample will allow the relative neutralizing titer of the sample to be quantified, relative to a given level of expression of the renilla reporter gene transcribed from the same promoter as IFNα.

The one-step assay according to the present invention is applicable to a wide range of biopharmaceuticals and allows residual drug levels to be quantification in a sample from the expression the drug-responsive reporter gene prior to induction of autocrine drug synthesis. Drug synthesis is then induced and NAb activity is quantified in the same sample from the change in expression of the drug-responsive reporter gene in the presence or absence of anti-drug antibodies, without the need for serial dilution of the sample, or addition of exogenous drug. Although the one-step NAb assay is based on the same principal as a conventional constant antibody neutralization assay, results are normalized relative to the expression of an internal standard and are consequently independent of cell number affording a high degree of assay precision. The one-step assay is thus ideally suited to high through-put analysis of anti-drug NAbs.

In another embodiment of the invention, the cell line used as the basis for the method of the present invention, the so called NanoLite One-Step neutralization assay, was derived from the human pro-monocytic cell line U937 transfected with the Renilla luciferase reporter gene under the control of an interferon-responsive chimeric promoter comprising a SV40 minimal promoter, and the ISRE from the ISG 15 gene. The cell line is also transfected with a second construct consisting of a vector expressing the ligand of interest and a firefly luciferase reporter gene product under the control of an inducible promoter such as the Tet-On CMV promoter.

The ligand reporter activity of the Renilla luciferase reporter gene is determined at various time points following addition of a luciferase reagent such as EnduRen, or ViviRen (Promega, Madison, Wis.) that allows Renilla luciferase activity to be determined continuously within live-cells. Alternatively, non-limiting examples of luciferases that can be used instead of Renilla luciferase include luciferases such as Gaussia Luciferase or Metridia luciferase together with the appropriate luciferase substrate. Thus, 10 µl of serum to be tested for the presence of anti-ligand antibodies is added to the well of a 96-well plate containing 50,000 One-Step cells (cells according to the present invention) in 50 μl of RPMI 1640 medium containing 2% BFS and 1.0 μg/ml of doxycycline and the appropriate luciferase substrate. The sample is incubated with the cells at 37° C. in the luminometer for a period ranging from 4 to 18 hours, most preferably 5 to 6 hours and RLU readings are taken at regular intervals. The neutralizing titer of the sample is calculated from the time taken, T2, in the presence of the anti-ligand antibody, to reach a relative level of *Renilla* luciferase expression obtained at a time, T1, in the absence of anti-ligand antibody.

Another aspect of the present invention is directed to a kit for determining the level in a sample of an extracellular ligand that initiates a ligand-specific signal at the nucleus of a cell. This kit includes a reagent containing a plurality of the cell of the present invention and either a testing device having a plurality of wells or a container for storing the reagent prior to use. The testing device is preferably a multi-well microtiter plate (e.g., 96 well microtiter plate), but can also be any type of receptacle such as petri dishes or plates with a plurality of wells in which an assay can be conducted. The reagent containing the cells may be disposed in the wells of the testing device, although it will be appreciated that such cells can instead be dispensed in the wells of the testing device by the end user just prior to conducting the assay. The kit may further include a set of instructions for using the kit in an assay. Preferably, the reagent in the kit is supplied frozen and, most preferably, the frozen cells according to the present invention as contained in the reagent have been treated with an anti-miotic or pro-apoptotic agent, as discussed above, prior to being frozen in a cryopreservative.

Having now generally described the invention, the same will be more readily understood through reference to the following example which is provided by way of illustration and is not intended to be limiting of the present invention.

EXAMPLE

A unique one-step cell-based assay for interferon alpha (IFNα) has been developed that allows both drug concentration and anti-drug neutralizing antibodies (NAbs) to be quantified in a single serum sample without the need for sample dilution, addition of exogenous drug, or other manipulation. IFN activity is quantified with a high degree of precision and within a few hours using cells, transfected with the firefly luciferase reporter-gene controlled by an IFN-responsive chimeric promoter. The assay cells have also been engineered to express and secrete IFNα, the production of which is normalized relative to the expression of the *Renilla* luciferase reporter gene transcribed from a common doxycycline inducible promoter. Thus, following quantification of residual IFN levels in a serum sample from an IFNα treated patient, autocrine IFN synthesis is induced and NAb activity can then be quantified instantaneously from the difference in expression of the IFN-responsive reporter gene, in the presence or absence of the sample. Assay results are normalized relative to the expression of an internal standard that renders results independent of cell number or differences in cell viability thus affording a high degree of assay precision. This unique assay platform is ideally suited for high throughput analysis of samples and is applicable to the quantification of both the activity and NAb levels for a number of biopharmaceuticals allowing comparison of immunogenicity data between assays and compounds.

Materials and Methods

PIL5 Reporter-Gene Assay. The synthetic double-stranded oligonucleotide CTCGGGAAAGGGAAAC-CGAAACTGAAGCC (SEQ ID NO:12), corresponding to the IRSE from the ISG-15 gene, controlling a SV40 minimal promoter was cloned upstream of the luciferase reporter-gene by insertion into the Xho/BglII site of the pGL2-promoter vector (Promega, Madison, Wis.) as described previously (Lallemand et al., 2008). Human promonocytic U937 cells were transfected with the IFN regulated gene reporter construct and stable transfectants were isolated and cloned. A human cell line, PIL5, carrying the luciferase reporter gene under the control of an IFN responsive chimeric promoter was thus established. Assay-ready vinblastin-treated, division-arrested PIL5 cells (iLite Alpha-Beta assay) were obtained from Biomonitor Ltd, Galway, Ireland, and stored frozen at −80° C. until use, according to the manufacturer's instructions. Briefly, frozen cells were thawed rapidly and incubated overnight in a 96-well microtiter plate (50,000 cells/well), in duplicate with serial dilutions of IFN in a total volume of 100 μl/well. Cells were then lysed by the addition of 100 μl/well of the luciferase substrate containing reagent, and luciferase activity was determined in a luminometer (LumiCount™, Packard Instruments Inc, Downers, Grove Ill.). Interferon activity was determined from the dose-response curve of relative luminescence units (RLU) against dilutions of the appropriate international IFN reference preparation using Excel™ software. Results are expressed in IU/ml.

Construction of the pTRE/IFNα2/hRL Vector. The TRE/IFNalpha2/hRL vector was constructed as follows: The coding region of the human IFNalpha2a gene was amplified by PCR from a human genomic extract using the following primers, which contain respectively EcoRI and BamHI restriction sites at their 5' extremities:

```
IFNalpha2 Sense:
                                  (SEQ ID NO: 13)
5' ACGTGAATTCGCAACATCTACAATGGCCTTGACCTTT 3'

FNalpha2 Anti-sense:
                                  (SEQ ID NO: 14)
5' GATCGGATCCAGTTTTCATTCCTTACTTCTTAAAC 3'
```

The humanized version of the *Renilla* luciferase gene (hRenilla) was amplified by PCR from the psiCHEK-2 vector (Promega, Catalog ref C8011) using the following primers which contained respectively SmaI and XbaI restriction sites at their 5' extremities:

```
hRenilla Sense:
                                  (SEQ ID NO: 15)
5' TCGTCCCGGGATGGCTTCCAAGGTGTACGACCCC 3' hRenilla Anti-sense:
                                  (SEQ ID NO: 16)
5' CTAGTCTAGATTACTGCTCGTTCTTCAGCACG 3'
```

The IFNalpha2 and the hRenilla amplification products were cloned in the EcoRI/BamHI and the SmaI/XbaI sites respectively of the pIRES2Neo plasmid (Clontech, Palo Alto, Calif., Catalog ref 6938-1). The EcoRI/XbaI restriction fragment of this construct, containing the coding region of the human IFNalpha2 gene, the IRES and the hRenilla gene, were cloned in the EcoRI/XbaI restrictions site of the pTRE-Tight vector (Clontech, Catalog ref. 631059). The integrity of each construct was verified by sequencing.

Patient Sera. Sera from patients treated with recombinant IFN α, or IFN β and monitored for the presence of neutralizing anti-IFN antibodies were randomly selected for evaluation in the present study.

Recombinant IFNα2a (Roferon-A™) was purchased from Hoffmann-La Roche, Neuilly-sur-Seine, France. The preparation used in this study had a titer of $9.0 \times 10^6$ IU/ml on human HuH7 cells challenged with vesicular stomatitis virus (VSV). The preparation was standardized against the human IFNα international reference preparation (G023-901-527). The specific activity of the interferon preparation was $2 \times 10^8$ IU/mg protein.

Recombinant IFNα2b (Intron-A™) was purchased from Schering-Plough, Levallois-Perret, France. The preparation used in this study had a titer of $1.0 \times 10^7$ IU/ml on human HuH7 cells challenged with VSV. The preparation was standardized against the human IFNα international reference preparation (G023-901-527). The specific activity of the interferon preparation was $2 \times 10^8$ IU/mg protein.

IFN Bioassay. IFN activity was assayed by the inhibition of the cytopathic effect (CPE) of VSV on human HuH7 cells as described previously (Lallemand et al., 2008).

Neutralization Assays. Briefly, serial dilutions of human serum were incubated in duplicate for 1 hour at 37° C. followed by 2 hours at 4° C. with a constant quantity (10 LU/ml) of a particular IFN preparation diluted in RPMI 1640 medium+2% fetal bovine serum (FBS) in a 96-well micro-titer plate (constant IFN method), or a constant dilution of serum was incubated under the same conditions with serial dilutions of IFN (constant antibody method). Residual IFN activity was then assayed using either the IFN viral cytopathic effect (CPE) bioassay or the PIL5 gene-reporter assay. The IFN preparation used in each neutralization test was also assayed simultaneously to determine its precise IFN activity in that day's assay. The lowest dilution of serum tested was also assayed alone for the presence of IFN activity or toxicity.

Neutralizing titer was determined using the Kawade methodology (Grossberg et al., 2001a and 2001b) which determines the reciprocal of the antibody dilution that reduces IFN activity from 10 to 1.0 LU/ml according to the formula; $t=f(n-1)/9$, where f=the reciprocal of the antibody dilution, and n=IFN concentration in LU/ml (Grossberg et al., 2001b; and Lallemand et al., 2008). Thus, when n=10 LU/ml, t=f. Neutralizing titers are expressed as Ten-fold Reduction Units/ml, or TRU/ml (Grossberg et al., 2001a and 2001b). Neutralization titers were corrected for the actual number of LU/ml of IFN used in the neutralization assay from the value obtained in the simultaneous IFN titration.

One-Step Neutralization Assay. PIL5C2.2 were incubated overnight in a 96-well micro-titer plate (37,500 cells/well), in duplicate with a single dilution of the serum sample to be tested in a total volume of 75 μl/well and 25 ng/ml Doxycycline (Clontech Catalog ref. 631311). The activities of both Firefly and Renilla luciferase were determined sequentially in the same well using the Dual-Glo luciferase assay system (Promega, Catalog ref. E2940) according to the manufacturer's instructions. The cells were first lysed by the addition of 75 μl/well of the Firefly luciferase substrate containing reagent, and FireFly luciferase activity was determined in a luminometer (LumiCount™, Packard Instruments Inc, Downers Grove Ill.). Renilla luciferase activity was then determined following addition in the same well of 50 μl the Renilla luciferase substrate. The neutralizing activity of the NAb sample was determined from the ratio of Firefly luciferase activity in the presence of the NAb containing sample (FL2) normalized relative to Renilla luciferase expression (RL2) and Firefly luciferase activity of the control sample (FL1) normalized relative to Renilla luciferase expression of the control sample (RL1): (FL2/RL2)/(FL1/RL1).

Results

Establishment of the IFN Secreting IFN Responsive Reporter-Gene Cell Line

Figure 14:
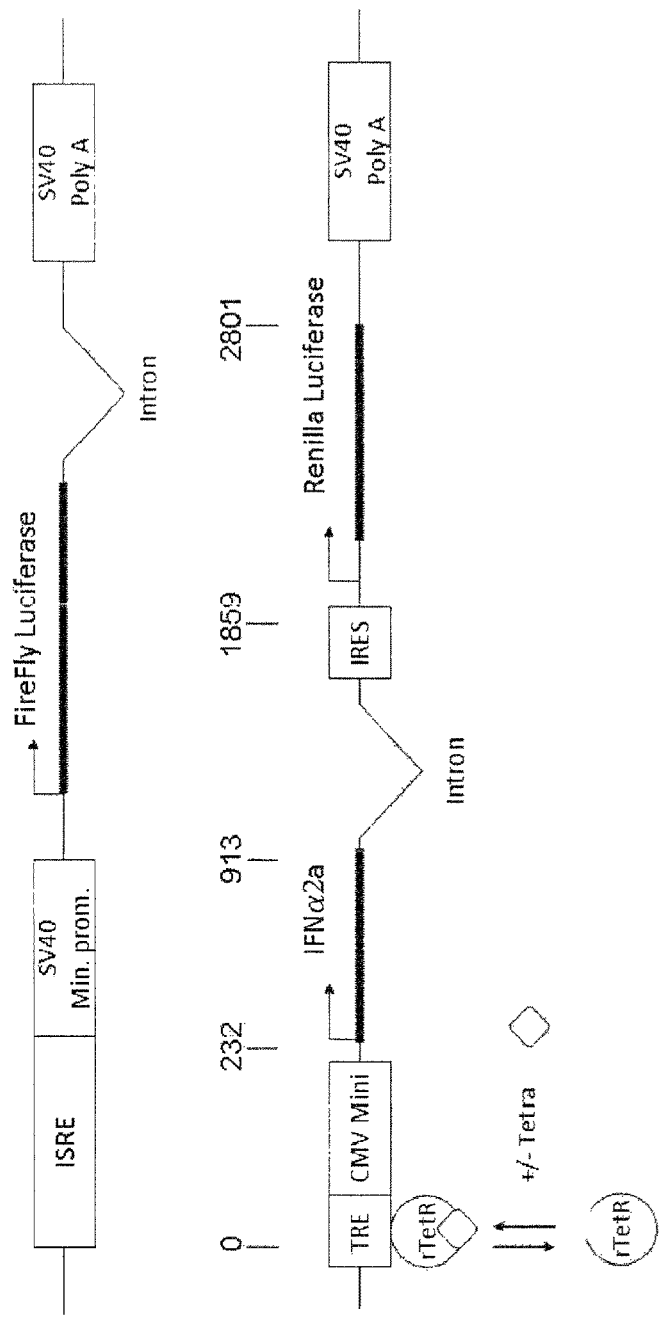
FIG. 14 is a schematic illustration of two separate constructs for the One-step assay in the Example herein below. The abbreviations are as follows: ISRE: Interferon Sensitive Response Element; SV40 Min. Prom: SV40 minimal promoter; Intron: Intron from the human β-globulin gene; SV40 Poly A: SV40 polyadenylation site; Firefly Luciferase: Coding region of the firefly luciferase gene; TRE: tetracycline responsive element; rTetR: Reverse tetracycline repressor; Tetra: Tetracycline; CMV Mini: CMV minimum promoter; IFNa2a: Signal peptide and coding region of the human interferon alpha2a gene; IRES: Internal ribosomal entry site; and Renilla Luciferase: Coding region of the Renilla luciferase gene

The human pro-monocytic cell line U937 was transfected with the firefly luciferase reporter gene controlled by an interferon responsive chimeric promoter containing a SV40 minimal promoter and the interferon sensitive response element (ISRE) from the ISG 15 gene as described previously (Lallemand et al., 2008). These cells were then co-transfected firstly with the 5,000 bp pTRE/IRES/IFNα2/hRL vector (SEQ ID NO:17) comprising the coding sequence of human IFNα2a gene including its natural signal peptide (nucleotides 323-913), the internal ribosome entry site (IRSE) of cytomegalovirus (CMV), nucleotides 914-1,859, together with the coding sequence of Renilla luciferase (nucleotides 1,860-2,801), under the control of a composite Tet-responsive element (TRE)-CMV promoter (nucleotides 1-323). This construction allows the primary RNA transcript to be translated into two distinct native proteins (IFNα2a and Renilla luciferase) so as to preserve the tertiary structure of the human IFNα2a protein and hence its recognition by anti-IFNα antibodies. Secondly, with a vector encoding the reverse Tet-controlled transactivation protein that confers tetracycline/doxycycline (Tet)-induced gene expression, as shown in FIG. 14.

The Renilla luciferase reporter-gene and the human IFNα2a gene were expressed under the control of a doxycycline inducible (Tet-On) CMV promoter in order to prevent continued expression of human type I IFNs from inhibiting cell proliferation and hence preventing cultivation of the transfected cell line.

Stable clones were isolated and tested for both strict inducibility of IFN expression and IFN responsiveness, following induction with doxycycline. Clone C2.2 (PIL5C2.2) was then characterized further.

Figures 15A, 15B:
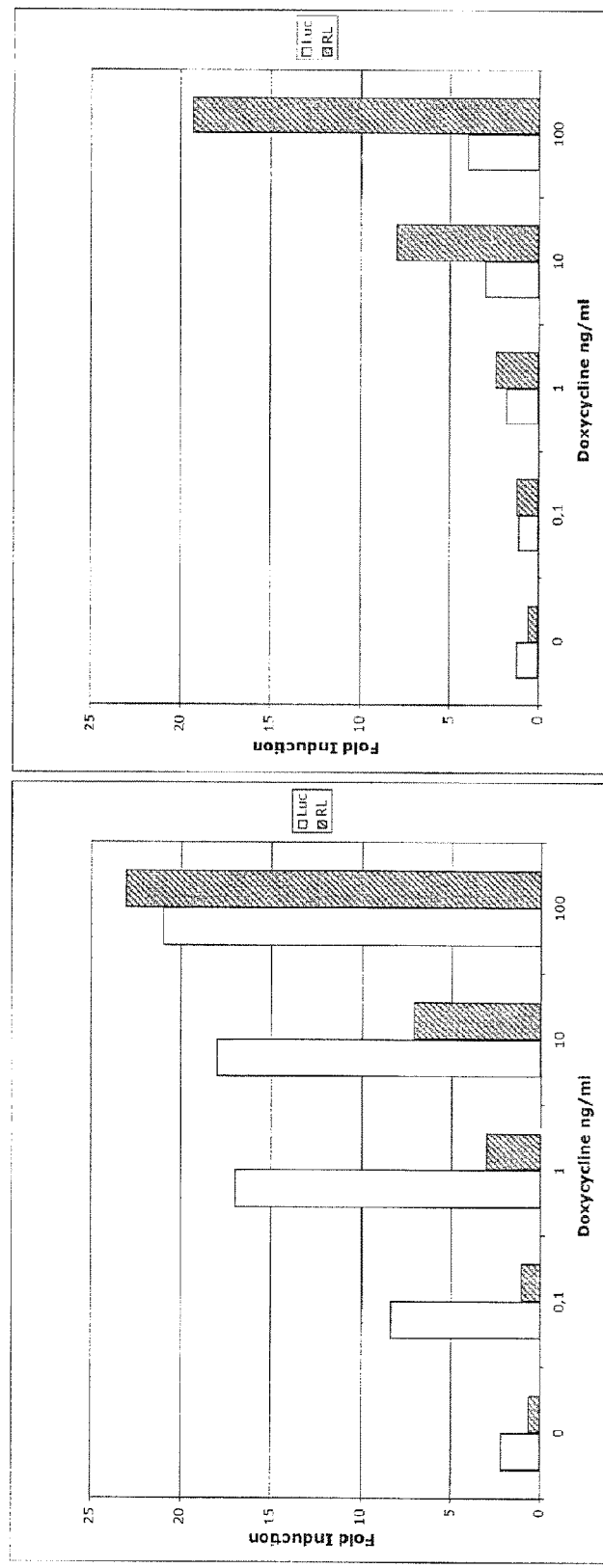
FIGS. 15A and 15B are graphs showing the effect of doxycycline centration on the expression of Firefly and Renilla luciferase activity in the One-step assay. One-step assay cells (PIL5C2.2) were treated with varying concentrations of doxycycline as described in the Materials and Methods and incubated overnight in duplicate with doxycycline alone or together with a 1/1,000 dilution of a polyclonal anti-human IFNα antibody as indicated in the figure. The activities of both Firefly and Renilla luciferase determined sequentially in the same well using the Dual-Glo luciferase assay system as described in the Materials and Methods. The cells were then lysed by the addition of 75 μl/well of the Firefly luciferase substrate containing reagent, and FireFly luciferase activity was determined as described in the Materials and Methods. Renilla luciferase activity was then determined following addition in the same well of 50 μl the Renilla luciferase substrate. The neutralizing activity of the NAb sample was then determined from the ratio of the activity of Firefly luciferase of the NAb containing sample (FL2) normalized relative to Renilla luciferase expression (RL2) and Firefly luciferase activity of the control sample (FL1) normalized relative to Renilla luciferase expression of the control sample (RL1): (FL2/RL2)/(FL1/RL1).

Treatment of PILC2.2 cells with increasing concentrations of doxycycline (0.1 to 100 ng/ml) resulted in a dose-dependent increase in the expression of Renilla luciferase (FIG. 15A). Increased expression of Renilla luciferase (RL-hatched bars) was accompanied by a corresponding increase in IFNα2a expression as demonstrated by increased production of IFNα2a in the culture supernatent (data not shown). Increased expression of IFNα2a was also accompanied by a corresponding increase in the expression of IFN-responsive firefly luciferase (FL) expression (FIG. 15A). Addition of a constant concentration of a polyclonal anti-IFNα neutralizing antibody resulted in a marked decrease in the expression of firefly luciferase (solid white bars-designated Luc in FIGS. 15A-15B), relative to the value observed in the presence of an equivalent dilution of control serum, without affecting the expression of Renilla luciferase expression significantly over a wide range of doxycycline concentrations (FIG. 15B).

Figure 16B:
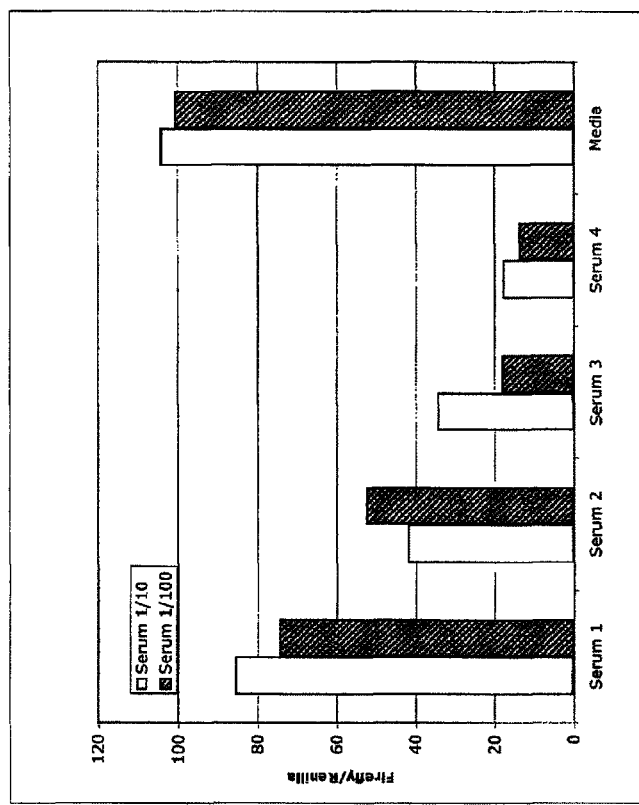
FIGS. 16A and 16B are graphs showing the effect of doxycycline concentration on the expression of Firefly and Renilla luciferase activity in the One-step assay. One-step assay cells (PIL5C2.2) were treated with varying concentrations of doxycycline as indicated in the figure and incubated overnight in duplicate with doxycycline alone or together with a 1/10 or 1/100 dilution of the human serum indicated in the figure. The activities of both Firefly and Renilla luciferase determined sequentially in the same well using the Dual-Glo luciferase assay system as described in the Materials and Methods. The cells were then lysed by the addition of 75 μl/well of the Firefly luciferase substrate containing reagent, and FireFly luciferase activity was determined as described in the Materials and Methods. Renilla luciferase activity was then determined following addition in the same well of 50 μl of the Renilla luciferase substrate. The neutralizing activity of the NAb sample was then determined from the ratio of the activity of Firefly luciferase of the NAb containing sample (FL2) normalized relative to Renilla luciferase expression (RL2) and Firefly luciferase activity of the control sample (FL1) normalized relative to Renilla luciferase expression of the control sample (RL1): (FL2/RL2)/(FL1/RL1).
Figure 16A:
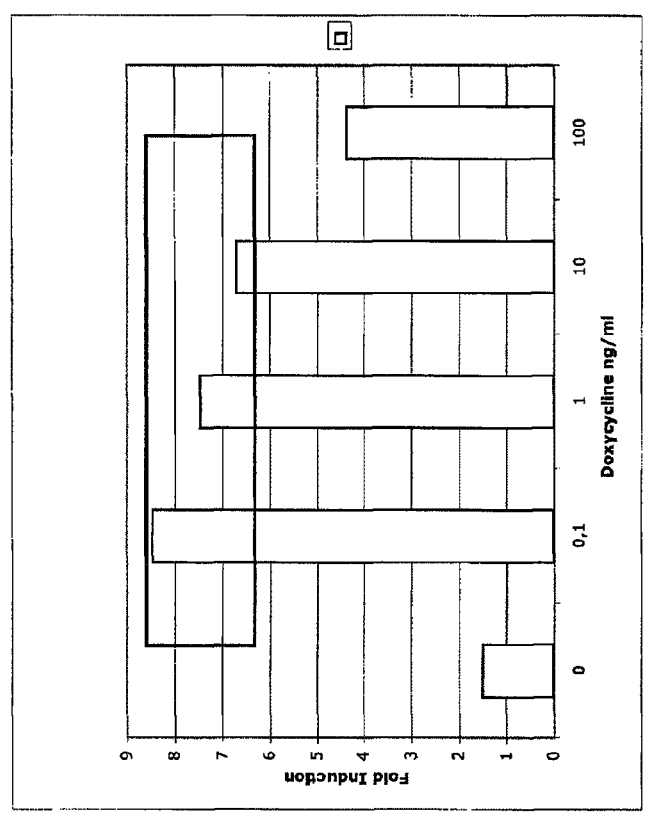

The ratio of firefly luciferase expression (abbreviated "FL") to Renilla luciferase (abbreviated "RL") expression in the absence of antibody relative to that in the presence of anti-IFNα antibody (FL1/RL1)/(FL2/RL2) remained relatively constant at doxycycline concentrations ranging from 0.1 to 10 ng/ml even though IFNα2 expression increased some 8 fold (FIG. 16A). The ratio (FL1/RL1)/(FL2/RL2) also remained relatively constant at either a 1:10 or 1:100 dilutions of individual sera from patients with chronic hepatitis C treated with IFNα2a or IFNα2b and containing neutralizing anti-IFNα antibodies (FIG. 16B).

Figure 17:
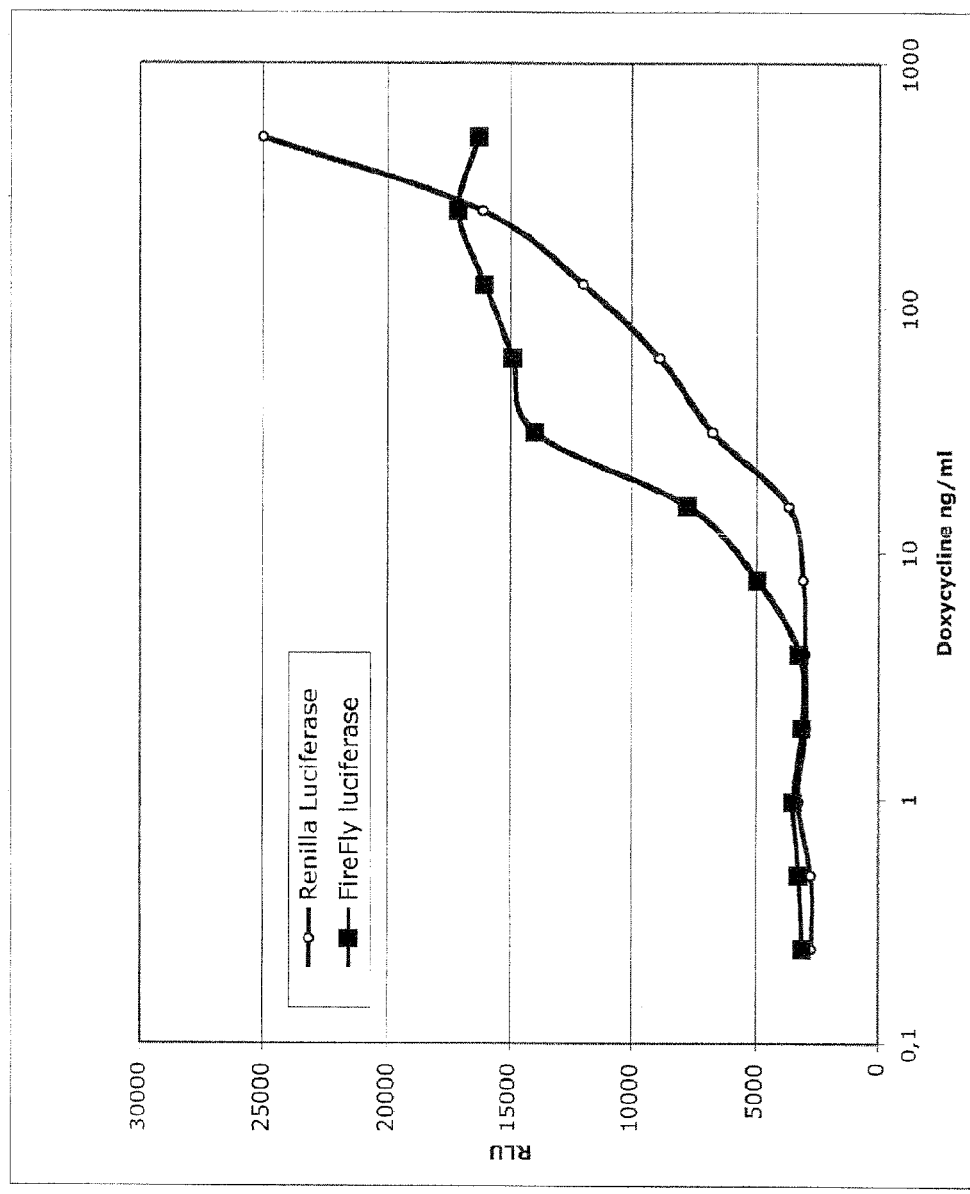
FIG. 17 is a graph showing the effect of doxycycline concentration on the expression of Firefly and Renilla luciferase activity in the One-step assay. One-step assay cells (PIL5C2.2) were treated with varying concentrations of doxycycline as described in the Materials and Methods and incubated overnight in duplicate. The activities of both Firefly and Renilla luciferase determined sequentially in the same well using the Dual-Glo luciferase assay system as described in the Materials and Methods. The cells were then lysed by the addition of 75 μl/well of the Firefly luciferase substrate containing reagent, and FireFly luciferase activity was determined as described in the Materials and Methods. Renilla luciferase activity was then determined following addition in the same well of 54 μl of the Renilla luciferase substrate.

Expression of firefly luciferase was found to follow a typical sigmoidal dose-response curve characteristic of a classic IFN dose-response curve following treatment of cells PILC2.3 cells with increasing concentrations of doxycycline (FIG. 17). In contrast, expression of *Renilla* luciferase did not saturate at the concentrations of doxycycline tested (FIG. 17).

Figure 18:
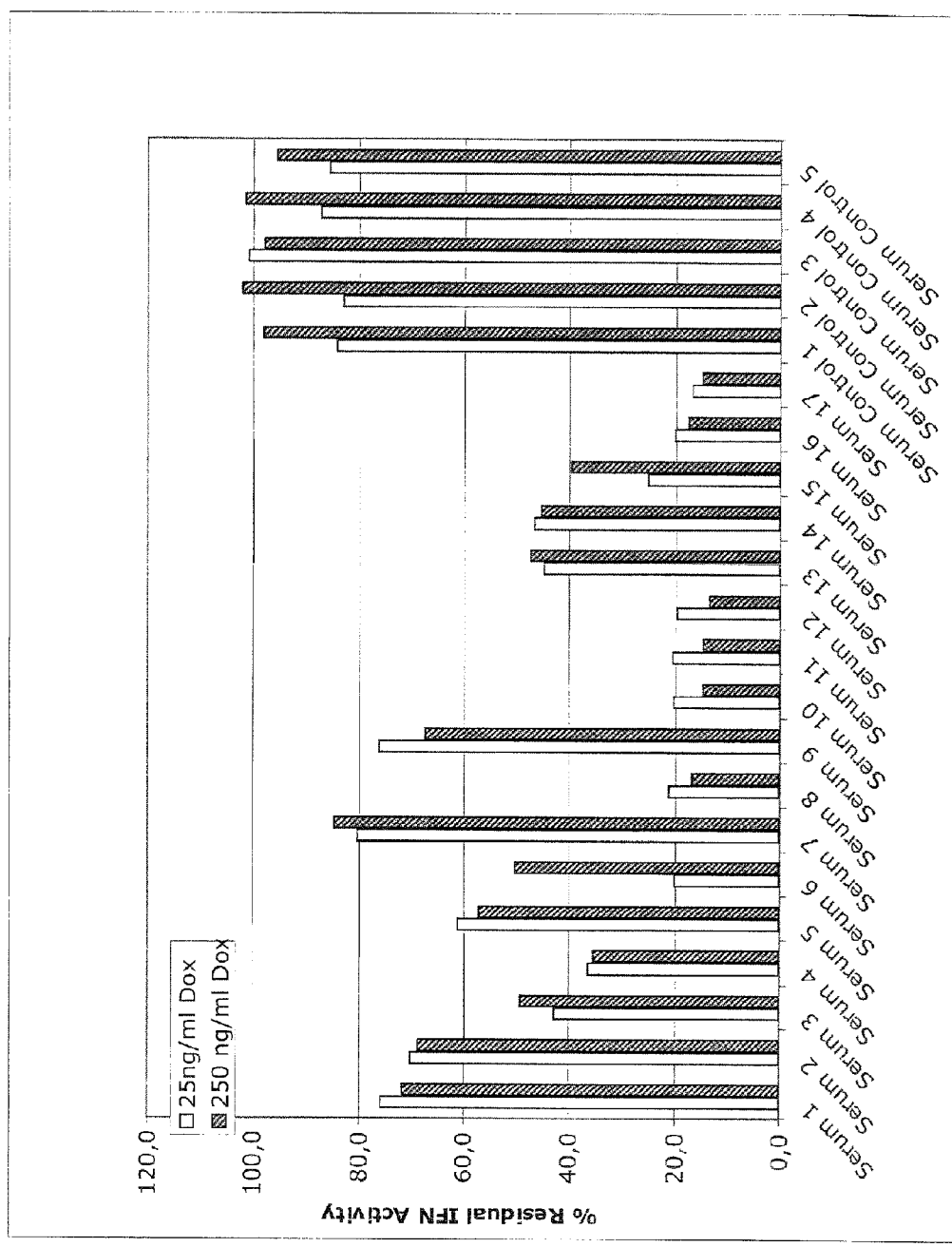
FIG. 18 is a graph showing the effect of varying concentration of doxycycline on the neutralization activities of human sera in the One-step assay. One-step assay cells (PIL5C2.2) were treated with varying concentrations of doxycycline as indicated in the figure and incubated overnight in duplicate with doxycycline alone or together with a 1:20 dilution of the human serum indicated in the figure. The activities of both Firefly and Renilla luciferase determined sequentially in the same well using the Dual-Glo luciferase assay system as described in the Materials and Methods. The cells were then lysed by the addition of 75 μl/well of the Firefly luciferase substrate containing reagent, and FireFly luciferase activity was determined as described in the Materials and Methods. Renilla luciferase activity was then determined following addition in the same well of 50 μl/well of the Renilla luciferase substrate. The neutralizing activity of the NAb sample was then determined from the ratio of the activity of Firefly luciferase of the NAb containing sample (FL2) normalized relative to *Renilla* luciferase expression (RL2) and Firefly luciferase activity of the control sample (FL1) normalized relative to *Renilla* luciferase expression of the control sample (RL1): (FL2/RL2)/(FL1/RL1).
Figure 19A:
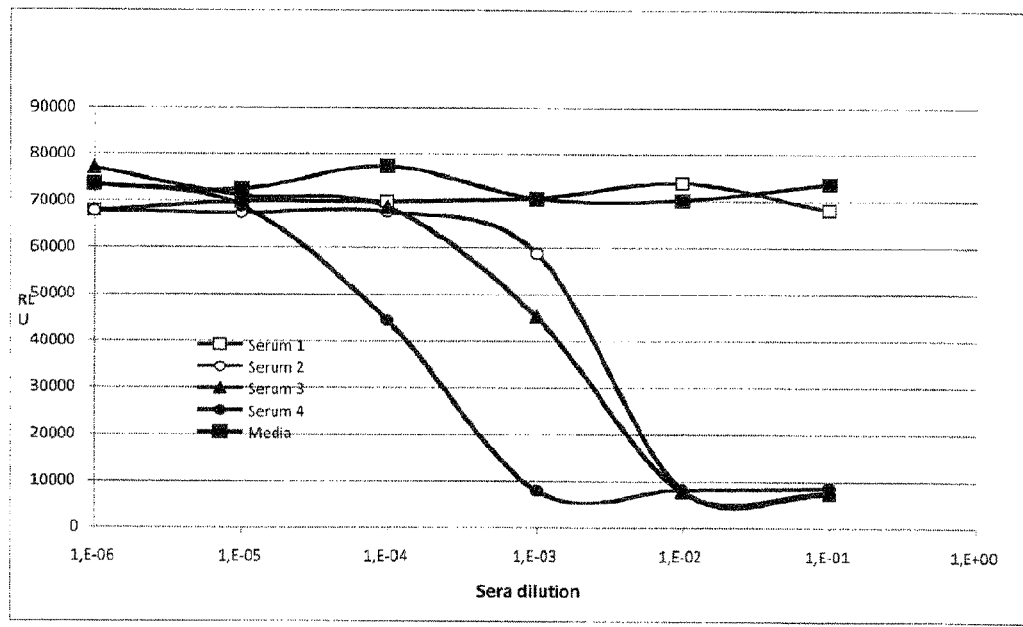
FIGS. 19A and 19B are graphs showing NAb quantification using a constant IFN concentration (100 IU/ml) versus varying serum concentrations (FIG. 19A) or varying IFN centration versus constant serum concentration (1/100) (FIG. 19B). Serial dilutions of human serum were incubated in duplicate for 1 hour at 37° C. followed by 2 hours at 4° C. with a constant quantity (10 LU/ml) of a IFNα2 as described in the Materials and Methods (FIG. 19A), or a constant dilution of serum (1:100) was incubated under the same conditions with serial dilutions of IFN (FIG. 19B). Residual IFN activity was then assayed using the PIL5 gene-reporter assay as described in the Materials and Methods. The IFN preparation used in each neutralization test was also assayed simultaneously to determine its precise IFN activity in that day's assay. The lowest dilution of serum tested was also assayed alone for the presence of IFN activity or toxicity. Neutralizing titer was determined using the Kawade methodology (Grossberg et al., 2001b; and Lallemand et al., 2008) which determines the reciprocal of the antibody dilution that reduces IFN activity from 10 to 1.0 LU/ml and expressed as TRU/ml as described in the Materials and Methods. Neutralization titers were corrected for the actual number of LU/ml of IFN used in the neutralization assay from the value obtained in the simultaneous IFN titration.
Figure 19B:
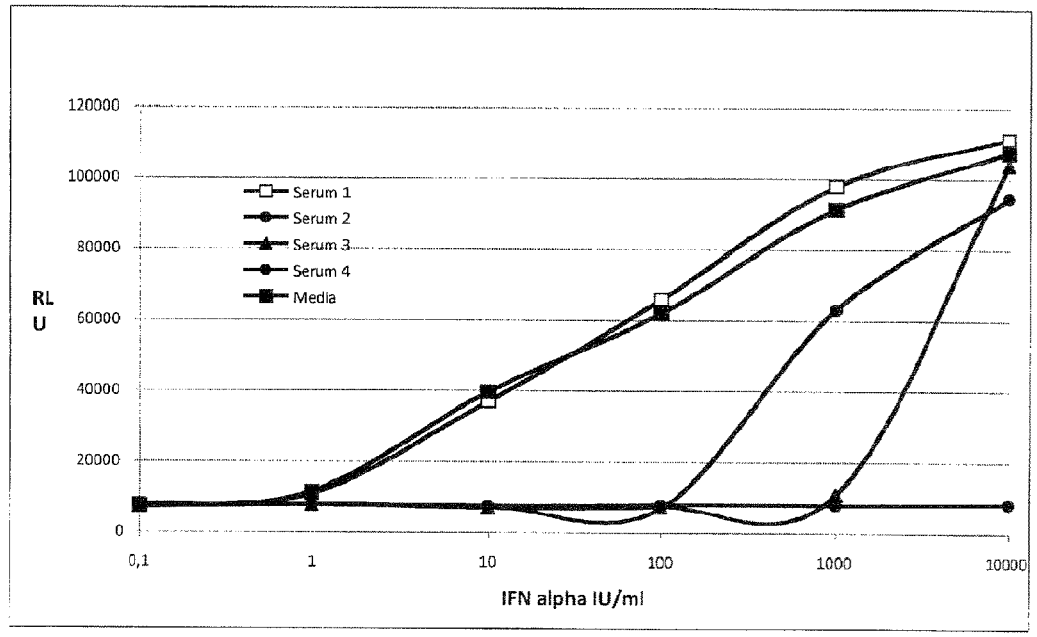

Treatment of PILC2.2 cells with different concentrations of doxycycline (25 or 250 ng/ml) did not change significantly the anti-IFNα neutralizing activity of the human sera tested. Thus a series of sera from patients with chronic hepatitis C containing varying anti-IFNα neutralizing activities were quantified using the one-step assay following treatment with either 25 or 250 ng/ml of doxycycline (FIG. 18).

Figure 20A:
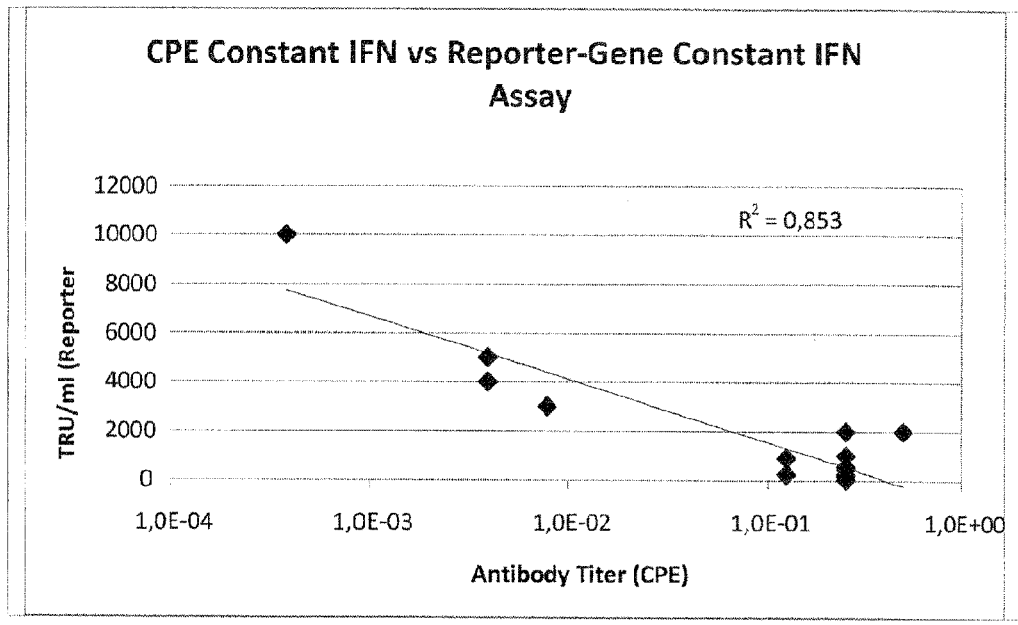
FIGS. 20A-20C are graphs comparing determination of neutralizing titer using different methods/assays. The neutralizing titer of a series of human sera was determined by the constant antibody method using the reporter-gene assay and the results were compared with those obtained for the same sera determined using the one-step assay (FIG. 20A). The neutralizing titer of the same series of human sera was determined by the constant IFN method using the CPE assay as described in the Materials and Methods and the results were compared with those obtained for the same sera determined using the reporter-gene assay and the constant antibody method (FIG. 20B). The neutralizing titer of the same series of human sera was determined by the constant IFN method using the CPE assay as described in the Materials and Methods and the results were compared with those obtained for the same sera determined using the one-step assay (FIG. 20C).
Figure 20B:
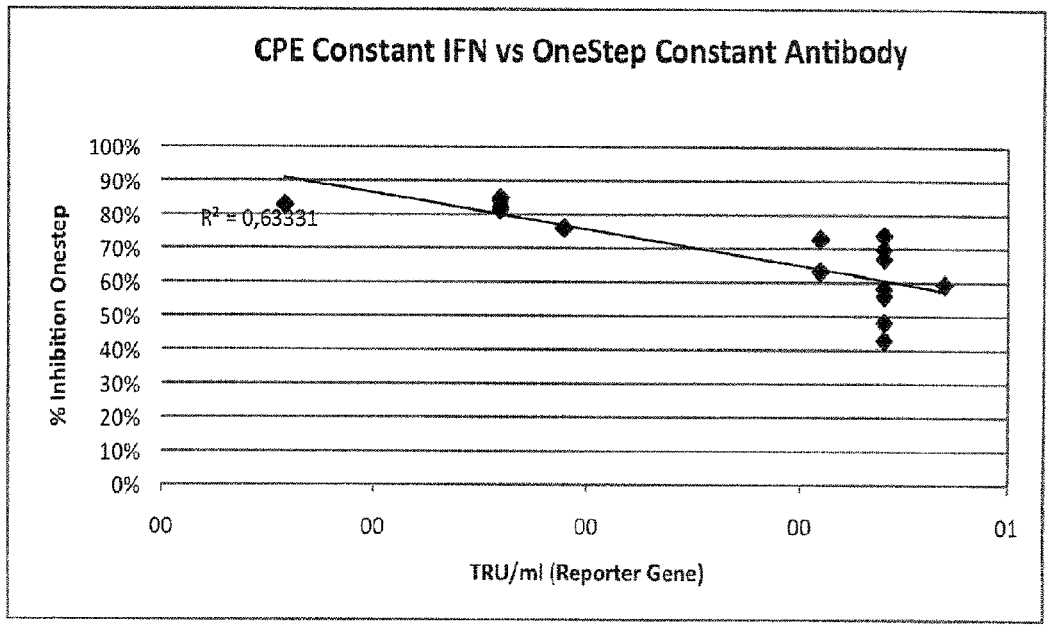
Figure 20C:
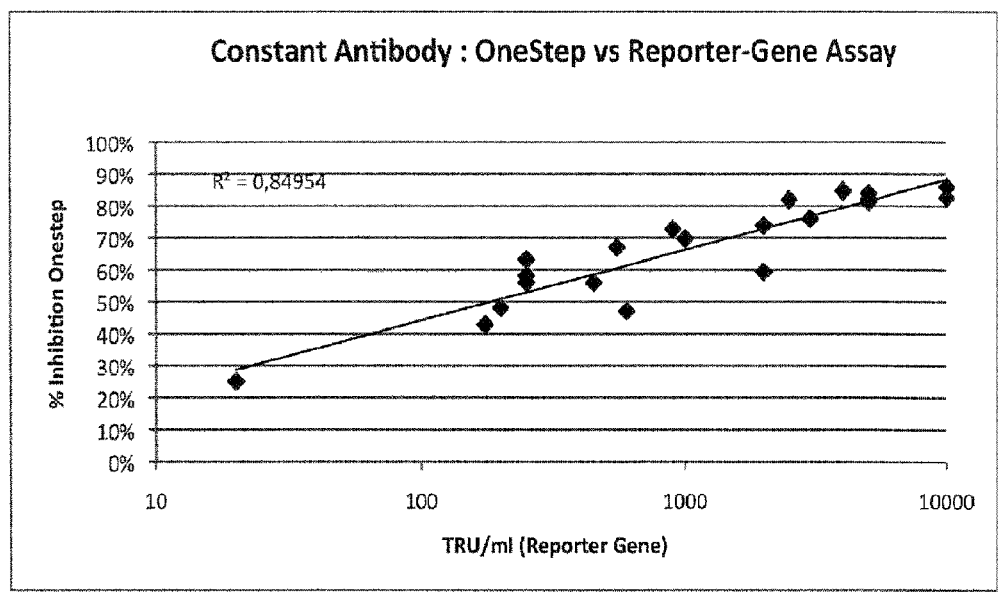

Two principal approaches are used to quantify anti-IFN NAbs: the constant IFN method and the constant antibody method. In the former, a constant quantity of IFN is mixed with increasing dilutions of serum while in the later a fixed dilution of serum in mixed with varying concentrations of IFN. Although both methods give similar results (FIGS. 19A and 19B) the constant antibody method has been reported to be the more sensitive of the two approaches and to be able to detect weakly neutralizing sera not detected by the constant IFN method (Lam et al., 2008). As the one-step NAb assay is based on the same principal as the constant antibody method, sera from patients with chronic hepatitis C treated with IFNα2a or IFNα2b were tested for the presence of neutralizing antibodies to IFNα using the constant antibody method and either a cytopathic inhibition (CPE) assay or luciferase reporter-gene assay to quantify IFNα activity. In keeping with a previous report (Lallemand et al., 2008), similar results were obtained for the neutralizing titers, expressed as TRU/ml, for individual sera using the constant IFN NAb assay, when tested using either the CPE or luciferase reporter-gene assays to measure IFN activity ($R^2=0.85$, FIG. 20A). The results were then compared with those obtained using the one-step method. Not surprisingly a somewhat lower degree of correlation (R2=0.63) was observed between the results obtained using the CPE assay to quantify anti-IFNα NAb levels using the constant IFN method and those obtained using the one-step assay (equivalent to the constant antibody method) to quantify the neutralizing titer in TRU/ml of the same samples (FIG. 20B). In contrast, a high degree of correlation ($R^2=0.85$), was observed for the anti-IFNα neutralizing titers of individual human sera, expressed as TRU/ml, using the constant IFN NAb assay and the luciferase reporter-gene assay to measure IFN activity compared with the results obtained for the same sera using the one-step method (FIG. 20C).

Although the one-step NAb assay is based on the same principal as a conventional constant antibody neutralization assay, the results are normalized relative to the expression of an internal standard and consequently are not influenced by variations in cell number or errors in sample dilution.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abramovich et al. (1994) Differential tyrosine phosphorylation of the IFNAR chain of the type I interferon receptor and of an associated surface protein in response to IFN-alpha and IFNbeta. *Embo J.* 13:5871.

Alton et al. (1979) Nucleotide sequence analysis of the chloramphenicol resistance transposon Tn9. *Nature* 282: 864-869

Ank et al *JICR* 2006, 26:373-379

Antonetti F, Finocchiaro O, Mascia M, Terlizzese M G, Jaber A. *J. Interferon & Cytokine Res.* (2002) 22:1181-1184.

Baldwin et al. (1984) Cloning of the luciferase structural genes from *Vibrio harveyi* and expression of bioluminescence in *Escherichia coli*. *Biochemistry* 23:3663-3667

Barbieri et al. (1994) Activation of the protein tyrosine kinase tyk2 by interferon alpha/beta. *Eur J. Biochem.* 223:427.

Basu et al. (1998) The antiviral action of interferon is potentiated by removal of the conserved IRTAM domain of the IFNAR1 chain of the interferon alpha/beta receptor: effects on JAK-STAT activation and receptor down-regulation. *Virology.* 242:14.

Bazan, (1990). Structural design and molecular evolution of a cytokine receptor superfamily. *Proc Natl Acad Sci USA.* 87:6934.

Bertolotto A, Malucchi S, Sala A, Orefice G, Carrieri P B, Capobianco M, Milano E, Melis F, Giordana M T. *J. Neuro Neurosurg. Psychiatry*, (2002) 73:148-153.

Bouche et al. (1987) Basic fibroblast growth factor enters the nucleolus and stimulates the transcription of ribosomal genes in ABAE cells undergoing G0 - - - G1 transition. *Proc. Natl. Acad. Sci.* U.S.A. 84:6770-6774

Boulter et al. (1986) Isolation of a cDNA clone coding for a possible neural nicotinic acetylcholine receptor alpha-subunit. *Nature* 319:368-374

Boulter et al. (1990) Alpha 3, alpha 5, and beta 4: three members of the rat neuronal nicotinic acetylcholine receptor-related gene family form a gene cluster. *J. Biol. Chem.* 265:4472-4482

Branca et al. (1981) Evidence that types I and II interferons have different receptors. *Nature.* 294:768.

Bunzow et al. (1988) Cloning and expression of a rat D2 dopamine receptor cDNA. *Nature* 336:783-787

Canosi et al. (1996) A highly precise reporter gene bioassay for type I interferon. *Journal of Immunological Methods* 199:69-76

Casadevall N, Nataf J, Viron B, Kolta A, Kiladjian J J, Martin-Dupont P, Michaud P, Papo T, Ugo V, Teyssandier I, Varet B, and Mayeux P. Pure red-cell aplasia and antierythropoietin antibodies in patients treated with recombinant erythropoietin. *N Engl J Med* 346: 469-475, 2002.

Changelian et al. (1989) Structure of the NGFI-A gene and detection of upstream sequences responsible for its transcriptional induction by nerve growth factor. *Proc. Natl. Acad. Sci.* USA 86:377-381

Changelian et al. (1989) Structure of the NGFI-A gene and detection of upstream sequences responsible for its transcriptional induction by nerve growth factor. *Proc. Natl. Acad. Sci.* 86:377-381

Cleary et al. (1994) Knockout and reconstitution of a functional human type I interferon receptor complex. *Journal of Biological Chemistry.* 269:18747.

Clerico M, Contessa G, Durelli L. Interferon-beta 1a for the treatment of multiple sclerosis. *Expert Opin. Biol. Ther.* (2007) 7:535-542.

Cohen et al. (1995) Ligand-induced association of the type I interferon receptor components. *Mol Cell Biol.* 15:4208.

Colamonici et al. (1994) Direct binding to and tyrosine phosphorylation of the alpha subunit of the type I interferon receptor by p135tyk2 tyrosine kinase. *Mol. Cell. Biol.* 14:8133.

Comb et al. (1986) *Nature* 323:353-356

Constantinescu et al. (1994) Role of interferon alpha/beta receptor chain 1 in the structure and transmembrane signaling of the interferon alpha/beta receptor complex. *Proc Natl Acad Sci* USA. 91:9602.

Constantinescu et al. (1995) Expression and signaling specificity of the IFNAR chain of the type I interferon receptor complex. *Proc Natl Acad Sci* USA. 92:10487.

Cook et al. (1996) Differential responsiveness of a splice variant of the human type I interferon receptor to interferons. *J Biol. Chem.* 271:13448.

Cutrone et al. (1997) Contributions of cloned type I interferon receptor subunits to differential ligand binding. *FEBS Lett.* 404:197.

Darnell et al. (1994) Jak-STAT pathways and transcriptional activation in response to IFNs and other extracellular signaling proteins. *Science.* 264:1415.

De Maeyer et al. (1988) Interferons and other regulatory cytokines. John Wiley, New York: 69.

Deisenhammer F, Schellekens H, Bertolotto A., Measurement of neutralizing antibodies to interferon beta in patients with multiple sclerosis, *J. Neurol.* (2004) 251 (Suppl. 2):11:31-11:39.

Deneris et al. (1988) Primary structure and expression of beta 2: a novel subunit of neuronal nicotinic acetylcholine receptors. *Neuron* 1:45-54

Deneris et al. (1989) Beta 3: a new member of nicotinic acetylcholine receptor gene family is expressed in brain. *J. Biol. Chem.* 264: 6268-6272 deWet et al. (1987) Firefly luciferase gene: structure and expression in mammalian cells. *Mol. Cell. Biol.* 7:725-737

Diaz et al. (1993) Nomenclature of the human interferon genes. *J Interferon Res.* 13:443

Diebold S S, Kaisho T, Hemmi H, Akira S, Reis, E., and Sousa C. (2003). Innate antiviral responses by means of TLR7-mediated recognition of single-stranded RNA. *Science.* 303, 1529-1531.

Dixon et al. (1986) Cloning of the gene and cDNA for mammalian beta-adrenergic receptor and homology with rhodopsin. *Nature* 321:75-79

Domanski et al. (1995) Cloning and expression of a long form of the beta subunit of the interferon alpha beta receptor that is required for signaling. *J Biol. Chem.* 270:21606.

Domanski et al. (1996) The type-I interferon receptor. The long and short of it. *Cytokine Growth Factor Rev.* 7:143.

Duvoisin et al. (1989) The functional diversity of the neuronal nicotinic acetylcholine receptors is increased by a novel subunit: beta 4. *Neuron* 3:487-496

Ellis et al. (1988) Sequence and expression of mRNAs encoding the alpha 1 and alpha 2 subunits of a DHP-sensitive calcium channel. *Science* 241:1661-1664

Engebrecht et al. (1984) Identification of genes and gene products necessary for bacterial bioluminescence. *PNAS* 1:4154-4158

Fiette et al. (1995) Theiler's virus infection of 129Sv mice that lack the interferon alpha/beta or interferon gamma receptors. *Journal of Experimental Medicine.* 181:2069.

Fink et al. (1988), The CGTCA sequence motif is essential for biological activity of the vasoactive intestinal peptide gene cAMP-regulated enhancer. *Proc. Natl. Acad. Sci.* 85:6662-6666

Frielle et al. (1987) Cloning of the cDNA for the human beta 1-adrenergic receptor. *Proc. Natl. Acad. Sci.* 84:7920-7924

Fu, (1992) A transcription factor with SH2 and SH3 domains is directly activated by an interferon alpha-induced cytoplasmic protein tyrosine kinase(s). *Cell.* 70:323.

Giovannoni G. Optimizing MS disease-modifying therapies: antibodies in perspective. *J. Neurol.* (2004) 251(Supl. 5) v30-v35.

Goldman et al. (1987) Members of a nicotinic acetylcholine receptor gene family are expressed in different regions of the mammalian central nervous system. *Cell* 48:965-973

Grossberg S E, Kawade Y, Kohase M, and Klein J P. The neutralization of interferons by antibody. II. Neutralizing antibody unitage and its relationship to bioassay sensitivity: the tenfold reduction unit. *J Interferon Cytokine Res* 21: 743-755, 2001a.

Grossberg S E, Kawade Y, Kohase M, Yokoyama H, and Finter N. The neutralization of interferons by antibody. I. Quantitative and theoretical analyses of the neutralization reaction in different bioassay systems. *J Interferon Cytokine Res* 21: 729-742, 2001b.

Hall et al. (1983) *J. Mol. Appl. Gen.* 2:101

Hammerling et al. (1998) The β-gal interferon assay: a new, precise, and sensitive method. *Journal of Interferon and Cytokine Research* 18:451-460

Hartung H P, Polman C, Bertolotto A, Deisenhammer F, Giovannoni G, Havrdova E, Hemmer B, Hillert J, Kappos L, Kieseier B, Killestein J, Malcus C, Comabella M, Pachner A, Schellekens H, Sellebjerg F, Selmaj K, Sorensen P S. Neutralizing antibodies to interferon beta: Expert panel report. *J. Neurol* (2007 Apr. 24) (Epub ahead of print)

Hollmann et al. (1989) Cloning by functional expression of a member of the glutamate receptor family. *Nature* 342:643-648

Hemmi, H., Takeuchi, O., Kawai, T., Kaisho, T., Sato, S., Sanjo, H., Matsumoto, M., Hoshino, K., Wagner, H., Takeda, K., and Akira, S. (2000). A Toll-like receptor recognizes bacterial DNA. *Nature,* 408, 740-745.

Hemmi, H., Takeuchi, O., Sato, S., Yamamoto, M., Kaisho, T., Santon H., Kawai, T., Hoshino, K., Takeda, K, and Akira, S. (2004). The roles of two ikappaB kinases in lipopolysaccharide and double stranded RNA signaling and viral infection. *J. Exp. Med.* 199, 1641-1650.

Horvath et al. (1995) A STAT protein domain that determines DNA sequence recognition suggests a novel DNA-binding domain *Genes Dev.* 9:984-994

Hwang et al. (1995) A null mutation in the gene encoding a type I interferon receptor component eliminates antiproliferative and antiviral responses to interferons alpha and beta and alters macrophage responses. *Proc Natl Acad Sci USA.* 92:11284.

Ihle, (1995) Cytokine receptor signalling. *Nature.* 377:591.

Jay et al. (1990) Primary structure of the gamma subunit of the DHP-sensitive calcium channel from skeletal muscle. *Science* 248:490-492

Johnson et al. (1986) *Cell* 47:545-554

Julius et al. (1988) Molecular characterization of a functional cDNA encoding the serotonin 1c receptor. *Science* 241:558-564

Julius et al. (1990) The 5HT2 receptor defines a family of structurally distinct but functionally conserved serotonin receptors. *PNAS* 87:928-932

Kayano et al, (1988) Primary structure of rat brain sodium channel III deduced from the cDNA sequence. *FEBS Lett.* 228:187-194

Kobilka et al. (1987) An intronless gene encoding a potential member of the family of receptors coupled to guanine nucleotide regulatory proteins. *Nature* 329:75-79

Kobilka et al. (1987) Cloning, sequencing, and expression of the gene coding for the human platelet alpha 2-adrenergic receptor. *Science* 238:650-656

Lallemand C, Lebon P. Rizza P, Blanchard B, Tovey M G. Constitutive expression of specific interferon isotypes in peripheral blood leukocytes from normal individuals and in promonocytiv U937 cells. *J. Leuk. Biol.* (1996) 60:137-146.

Lallemand C, Meritet J F, Erickson R, Grossberg S E, Roullet E, Lyon-Caen O, Lebon P, and Tovey M G. Quantification of neutralizing antibodies to human type I interferons using division-arrested frozen cells carrying an interferon-regulated reporter-gene. *J Interferon Cytokine Res* 28: 393-404, 2008.

Lam R, Farrell R, Aziz T, Gibbs E, Giovannoni G, Grossberg S, and Oger J. Validating parameters of a luciferase reporter gene assay to measure neutralizing antibodies to IFNbeta in multiple sclerosis patients. *J Immunol Methods* 336: 113-118, 2008.

Langer et al. (1996) Interferon receptors. *Biotherapy.* 8:163

Levitan et al. (1988) Structural and functional basis for GABAA receptor heterogeneity. *Nature* 335:76-79

Levy et al. (1988) Interferon-induced nuclear factors that bind a shared promoter element correlate with positive and negative control *Genes Dev.* 2:383-393

Lewis, (1995) A sensitive biological assay for interferons. *Journal of Immunological Methods* 185:9-17

Lim et al. (1993) Cloning and characterization of a bovine alpha interferon receptor. *Biochim Biophys Acta.* 1173:314.

Lleonart et al., (1990) A novel, quantitative bioassay for type I interferon using a recombinant indicator cell line. *Biotechnology* 8:1263-1267

Lutfalla et al. (1992) The structure of the human interferon alpha/beta receptor gene. *J Biol Chem.* 267:2802.

Lutfalla et al. (1995) Mutant U5A cells are complemented by an interferon-alpha beta receptor subunit generated by alternative processing of a new member of a cytokine receptor gene cluster. *Embo J.* 14:5100.

McCormick P L, Scott U. Interferon-beta-1b: a review of its use in relapsing-remitting ans secondary progressive multiple sclerosis. *CNR Drugs,* (2004) 18:521-546.

McKinnon, D. (1989) Isolation of a cDNA clone coding for a putative second potassium channel indicates the existence of a gene family. *J. Biol. Chem.* 264:8230-8236

Meager, A. (2006) Measurement of cytokines by bioassays: Theory and application, *Methods* 28:237-252.

Merlin et al. (1985) 125I-labelled human interferons alpha, beta and gamma: comparative receptor-binding data. *J Gen Virol.* 66:1149.

Montminy et al. (1986), Identification of a cyclic-AMP-responsive element within the rat somatostatin gene. *Proc. Natl. Acad. Sci.* 83:6682-6686

Mouchel-Vielh et al. (1992). Specific antiviral activities of the human alpha interferons are determined at the level of receptor (IFNAR) structure. *FEBS Lett.* 313:255.

Muller et al. (1994) Functional role of type I and type II interferons in antiviral defense. *Science.* 264:1918.

Namaka M, Pollitt-Smith M, Gupta A, Klowak M, Vasconcelos M, Turcotte D, Gong Y, Melanson M. *Curr. Med. Res. Opin.* (2006)

Neumann T A and Foote M. Megakaryocyte growth and development factor (MGDF): an Mpl ligand and cytokine that regulates thrombopoiesis. *Cytokines Cell Mol Ther* 6: 47-56, 2000.

Noda et al. (1986) *Nature* 320:188-192

Noronha A. Neutralizing antibodies to interferon. *Neurology,* (2007) 68(24 Suppl 4):S16-22.

Novick et al. (1994) The human interferon alpha/beta receptor: characterization and molecular cloning. *Cell.* 77:391.

Perry et al., (1999) Cloning of interferon-stimulated gene 17: The promoter and nuclear proteins that regulate transcription. *Molecular Endocrinology,* 13:1197-1206

Perry, A. K., Chow, E. K., Goodnougy, J. B., Yeh, W. C., and Cheng, G. (2004). Differential requirement for TANK-binding kinase-1 in type I interferon responses Pestka et al. (1987) Interferons and their actions. *A. Rev. Biochem.* 56:727.

Platanias et al. (1994) Tyrosine phosphorylation of the alpha and beta subunits of the type I interferon receptor. Interferon-beta selectively induces tyrosine phosphorylation of an alpha subunit-associated protein. *J. Biol. Chem.* 269:17761.

Pritchett et al. (1989) Importance of a novel GABAA receptor subunit for benzodiazepine pharmacology. *Nature* 338:582-585

Rider et al. (2003) A B cell-based sensor for rapid identification of pathogens. *Science* 301:213-215

Rudick R A, Stuart W H, Calabresi P A, Confavreux C, Galetta S L, Radue E W, Lublin F D, Weinstock-Guttman B, Wynn D R, Lynn F, Panzara M A, Sandrock A W. *N. Engl. J. Med.* (2006) 354:911-923.

Russell-Harde et al. (1995) Reconstitution of a high affinity binding site for type I interferons. *J Biol. Chem.* 270: 26033.

Ruth et al. (1989) Primary structure of the beta subunit of the DHP-sensitive calcium channel from skeletal muscle. *Science* 245:1115-1118

Schindler et al. (1992) Interferon-dependent tyrosine phosphorylation of a latent cytoplasmic transcription factor [see comments]. *Science.* 257:809.

Schellekens H. How to predict and prevent the immunogenicity of therapeutic proteins. *Biotechnol Annu Rev* 14: 191-202, 2008.

Schofield et al. (1987) Sequence and functional expression of the GABA A receptor shows a ligand-gated receptor super-family. *Nature* 328:221-227

Schumacher et al. (1994) The chicken Mx promoter contains an ISRE motif and confers interferon inducibility to a reporter gene in chick and monkey cells. *Virology* 15:203 (1):144-8

Sheng et al. (1990) The regulation and function of c-fos and other immediate early genes in the nervous system. *Neuron* 4:477-485

Sheppard et al *Nat. Immunol.* 2003; 4:63-68

Shivers, B. D. (1989) *Neuron* 3:327-337

Short et al. (1986) *J. Biol. Chem.* 261:9721-9726

Steinhoff et al. (1995) Antiviral protection by vesicular stomatitis virus-specific antibodies in alpha/beta interferon receptor-deficient mice. *Journal of Virology.* 69:2153.

Steinman, R. M., and Hemmi, H. (2006). Dendritic cells: translating innate to adaptive immunity. *Curr. Top. Microbiol. Immunol.* 311, 17-58.

Stormann et al. (1990) Molecular cloning and expression of a dopamine D2 receptor from human retina. *Molec. Pharm.* 37:1-6

Tanabe et al. (1987) Primary structure of the receptor for calcium channel blockers from skeletal muscle. *Nature* 328:313-E318

Taniguchi, (1995) Cytokine signaling through nonreceptor protein tyrosine kinases. *Science.* 268:251.

Tempel et al. (1988) Cloning of a probable potassium channel gene from mouse brain. *Nature* 332:837-839

Thoreau et al. (1991) Structural symmetry of the extracellular domain of the cytokine/growth hormone/prolactin receptor family and interferon receptors revealed by hydrophobic cluster analysis. *FEBS Lett.* 282:26.

Toh et al. (1989) Isolation and characterization of a rat liver alkaline phosphatase gene. A single gene with two promoters. *Eur. J. Biochem.* 182:231-238

Uddin et al. (1995) Interaction of the transcriptional activator Stat-2 with the type I interferon receptor. *J Biol. Chem.* 270:24627.

Uematsu, S., and Akira, S. (2007). Toll-like receptors and type I interferons. *J. Biol. Chem.* 282, 15319-15323.

Uze at al. (1990) Genetic transfer of a functional human interferon alpha receptor into mouse cells: cloning and expression of its cDNA. *Cell.* 60:225.

Uze at al. (1992) Behavior of a cloned murine interferon alpha/beta receptor expressed in homospecific or heterospecific background. *Proc Natl Acad Sci USA.* 89:4774.

Uzé et al. (1995) Alpha and beta interferons and their receptor and their friends and relations. *Journal of Interferon & Cytokine Research.* 15:3.

van den Broek et al. (1995) Antiviral defense in mice lacking both alpha/beta and gamma interferon receptors. *Journal of Virology.* 69:4792.

Vandenbroek et al. (1995) Immune defense in mice lacking type I and/or type II interferon receptors. *Immunol Rev.* 148:5.

Velazquez et al. (1995) Distinct domains of the protein tyrosine kinase tyk2 required for binding of interferon-alpha/beta and for signal transduction. *J Biol. Chem.* 270:3327.

Wada et al. (1988) Functional expression of a new pharmacological subtype of brain nicotinic acetylcholine receptor. *Science* 240:330-334

Yan et al. (1996) Molecular characterization of an alpha interferon receptor 1 subunit (IFNaR1) domain required for TYK2 binding and signal transduction. *Mol Cell Biol.* 16:2074.

Yan et al. (1996) Phosphorylated interferon-alpha receptor 1 subunit (IFNaR1) acts as a docking site for the latent form of the 113 kDa STAT2 protein. *EMBO J.* 15:1064.

Yeh et al. (1987) Ultrastructural localization of a platelet-derived growth factor/v-sis-related protein(s) in cytoplasm and nucleus of simian sarcoma virus-transformed cells. *Proc. Natl. Acad. Sci.* U.S.A. 84:2317-2321

Ymer et al. (1989) GABAA receptor beta subunit heterogeneity: functional expression of cloned cDNAs. *EMBO J.* 8:1665-1670

Yoneyama, M., Fujita, T. (2007). Function of RIG-1-like receptors in antiviral innate immunity. *J. Biol. Chem.* 282, 15315-15318.

Zlokarnik et al. (1998) Quantitation of transcription and clonal selection of single living cells with β-lactamase as reporter. *Science* 279:84-88.

---

What is claimed is:

1. A cell having a cell-surface receptor for a ligand selected from the group consisting of a cytokine and a growth factor in the external environment surrounding the cell, wherein binding of the ligand to the cell surface receptor initiates a specific signal at the nucleus of the cell, said cell comprising:
   (a) a first DNA construct having a sequence comprising
      (i) a first set of one or more transcription control elements comprising a chimeric promoter, said first set of one or more transcription control elements being inducible by the signal initiated by the binding of said ligand to the cell surface receptor, and
      (ii) a portion encoding a first measurable tag, driven by said first set of one or more transcription control elements, which tag can be detected when the first set of one or more transcription control elements is induced by the signal initiated by the binding of the ligand to the cell surface receptor; and
   (b) a second DNA construct having a sequence comprising:
      (i) a second set of one or more transcription control elements different from said first set; and
      (ii) a portion encoding the ligand and a signal peptide that causes secretion of the ligand to the external environment surrounding the cell, said portion being driven by said second set of one or more transcription control elements.

2. The cell of claim 1, wherein said second set of one or more transcription control elements comprises an inducible transcription control element which is inducible by a first protein that is not the same as the ligand.

3. The cell of claim 2, wherein said inducible transcription control element is a tetracycline (Tet)-responsive element (TRE) and wherein the cell further comprises an additional DNA construct that constitutively expresses a reverse tetracycline repressor (rTetR) that turns off/represses the action of said inducible TRE in the absence of tetracycline or doxycycline as an inducer in a Tet-On expression system.

4. The cell of claim 2, wherein said inducible transcription control element is a tetracycline (Tet)-responsive element (TRE) and wherein the cell further comprises an additional DNA construct that constitutively expresses a tetracycline-controlled transactivator (tTA) that binds to said inducible TRE in the absence of tetracycline or doxycycline to activate transcription from TRE as a Tet-Off expression system.

5. The cell of claim 2, further comprising:
   (c) a third DNA construct having a sequence comprising
      (i) a third set of one or more transcription control elements different from the first and second set, and being inducible by a second protein that is not the same as the ligand or the first protein; and
      (ii) a portion encoding an antagonist for the ligand, driven by said third set of one or more transcription control elements.

6. The cell of claim 5, wherein the sequence of said third DNA construct further comprises, on a separate cistron from said portion encoding the antagonist for the ligand, a second portion also driven by said third set of one or more transcription control elements and encoding a third measurable tag, which third tag is independently measured in the presence of said first tag.

7. The cell of claim 6, wherein the sequence of said second DNA construct further comprises, on a separate cistron from said portion encoding the ligand, a second portion also driven by said second set of one or more transcription control elements and encoding a second measurable tag, which second tag is independently measured in the presence of said first tag and said third tag.

8. The cell of claim 1, wherein the ligand is a cytokine.

9. The cell of claim 1, wherein the ligand is an interferon.

10. The cell of claim 9, wherein said first set of one or more transcription control elements comprises an interferon stimulatory response element (ISRE).

11. The cell of claim 1, wherein the ligand is tumor necrosis factor α (TNFα).

12. The cell of claim 11, wherein said first set of one or more transcription control elements comprises an NFκB binding site.

13. The cell of claim 1, wherein the ligand is erythropoietin (EPO).

14. The cell of claim 13, wherein said first set of one or more transcription control elements comprises a signal transducer and activator of transcription #5 element (STAT5).

15. The cell of claim 1, which is a mammalian or avian cell.

16. The cell of claim 1, which is a human cell.

17. The cell of claim 1, which is a human promonocytic cell.

18. The cell of claim 17, wherein the human promonocytic cell is a U937 cell.

19. The cell of claim 1, wherein the sequence of said second DNA construct further comprises, on a separate cistron from said portion encoding the ligand, a second portion also driven by said second set of one or more transcription control elements and encoding a second measurable tag, which second tag is independently measured in the presence of said first tag, and vice versa.

20. The cell of claim 19, wherein said first or second measurable tag is a luciferase.

21. The cell of claim 20, wherein said luciferase is *Renilla* luciferase.

22. The cell of claim 20, wherein said luciferase is firefly luciferase.

23. The cell of claim 19, wherein said first and second measurable tags are different luciferases.

24. A kit for determining the level in a sample of a ligand selected from the group consisting of a cytokine and a growth factor in the external environment surrounding the cell, wherein binding of the ligand to the cell surface receptor initiates a ligand-specific signal at the nucleus of a cell, comprising:
   a reagent containing a plurality of the cell of claim 1; and
   either a testing device having a plurality of wells or a container.

25. The kit of claim 24, wherein said reagent is disposed in the wells of said testing device or in said container.

26. The kit of claim 24, wherein said reagent is frozen.

27. A method for determining the level in a sample of a ligand selected from the group consisting of a cytokine and a growth factor in the external environment surrounding the cell that initiates a ligand-specific signal at the nucleus of a cell when binding to a cell surface receptor on the cell, or of a neutralizing antibody either against the ligand or against an antagonist of the ligand, comprising:
   incubating the cell of claim 1 in a mixture with a sample in which the level of the ligand or the neutralizing antibody is sought to be determined; and
   determining the level of the first measurable tag in the mixture relative to the level of the first measurable tag in the absence of the sample to thereby determine the level in the sample of the ligand or neutralizing antibody.

* * * * *

SEQUENCE LISTING

```
<160> NUMBER OF SEQ ID NOS: 17

<210> SEQ ID NO 1
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: ISRE

<400> SEQUENCE: 1
ggraaagwga aactg                                                      15
```

```
<210> SEQ ID NO 2
<211> LENGTH: 60
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: ISRE from ISG15

<400> SEQUENCE: 2
ctcgggaaag ggaaaccgaa actgaagccc ctcgggaaag ggaaaccgaa actgaagccc    60

<210> SEQ ID NO 3
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: GAS
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 3
nnnsanttcc gggaantgns n                                              21

<210> SEQ ID NO 4
<211> LENGTH: 58
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: 5xSTAT5

<400> SEQUENCE: 4
tcgagttcga agaaaacttc ttggaagatt cctggagctt ctaggaagat tccgggaa      58

<210> SEQ ID NO 5
<211> LENGTH: 5981
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: pIRES/IFNA/hRL
<220> FEATURE:
<221> NAME/KEY: misc_feature
<222> LOCATION: (309)..(810)
```

```
<223> OTHER INFORMATION: CMV promoter
<220> FEATURE:
<221> NAME/KEY: misc_feature
<222> LOCATION: (970)..(1562)
<223> OTHER INFORMATION: huIFNalpha2
<220> FEATURE:
<221> NAME/KEY: misc_feature
<222> LOCATION: (1818)..(2508)
<223> OTHER INFORMATION: IRES
<220> FEATURE:
<221> NAME/KEY: misc_feature
<222> LOCATION: (2508)..(3450)
<223> OTHER INFORMATION: hRenilla
<220> FEATURE:
<221> NAME/KEY: misc_feature
<222> LOCATION: (3450)..(3728)
<223> OTHER INFORMATION: poly A bGh

<400> SEQUENCE: 5
gggatggctt ccaaggtgta cgaccccgag caacgcaaac gcatgatcac tgggcctcag      60
tggtgggctc gctgcaagca aatgaacgtg ctggactcct tcatcaacta ctatgattcc     120
gagaagcacg ccgagaacgc cgtgattttt ctgcatggta acgctgcctc cagctacctg     180
tggaggcacg tcgtgcctca catcgagccc gtggctagat gcatcatccc tgatctgatc     240
ggaatgggta agtccggcaa gagcgggaat ggctcatatc gcctcctgga tcactacaag     300
tacctcaccg cttggttcga gctgctgaac cttccaaaga aaatcatctt tgtgggccac     360
gactgggggg cttgtctggc cttccactac tcctacgagc accaagacaa gatcaaggcc     420
atcgtccatg ctgagagtgt cgtggacgtg atcgagtcct gggacgagtg gcctgacatc     480
gaggaggata tcgccctgat caagagcgaa gagggcgaga aatggtgct tgagaataac     540 ttcttcgtcg agaccatgct cccaagcaag atcatgcgga aactggagcc tgaggagttc     600
gctgcctacc tggagccatt caaggagaag ggcgaggtta cggcctac cctctcctgg     660 cctcgcgaga tccctctcgt taagggaggc aagcccgacg tcgtccagat tgtccgcaac     720
tacaacgcct accttcgggc cagcgacgat ctgcctaaga tgttcatcga gtccgaccct     780
gggttctttt ccaacgctat tgtcgaggga gctaagaagt tccctaacac cgagttcgtg     840
aaggtgaagg gcctccactt cagccaggag gacgctccag atgaaatggg taagtacatc     900
aagagcttcg tggagcgcgt gctgaagaac gagcagtaat ctagagctcg ctgatcagcc     960
tcgactgtgc cttctagttg ccagccatct gttgtttgcc cctcccccgt gccttccttg    1020
accctggaag gtgccactcc cactgtcctt tcctaataaa atgaggaaat tgcatcgcat    1080
tgtctgagta ggtgtcattc tattctgggg gtggggtgg gcaggacag caaggggag    1140 gattgggaag acaatagcag gcatgctggg gatgcggtgg gctctatggc ttctgaggcg    1200
gaaagaacca gctggggctc gagtgcattc tagttgtggt ttgtccaaac tcatcaatgt    1260
atcttatcat gtctgtatac cgtcgacctc tagctagagc ttggcgtaat catggtcata    1320
gctgtttcct gtgtgaaatt gttatccgct cacaattcca cacaacatac gagccggaag    1380
cataaagtgt aaagcctggg gtgcctaatg agtgagctaa ctcacattaa ttgcgttgcg    1440
ctcactgccc gctttccagt cgggaaacct gtcgtgccag ctgcattaat gaatcggcca    1500
acgcgcgggg agaggcggtt tgcgtattgg gcgctcttcc gcttcctcgc tcactgactc    1560
gctgcgctcg gtcgttcggc tgcggcgagc ggtatcagct cactcaaagg cggtaatacg    1620
gttatccaca gaatcagggg ataacgcagg aaagaacatg tgagcaaaag gccagcaaaa    1680
ggccaggaac cgtaaaaagg ccgcgttgct ggcgttttc cataggctcc gcccccctga    1740
cgagcatcac aaaaatcgac gctcaagtca gaggtggcga aacccgacag gactataaag    1800
```

```
ataccaggcg tttcccctg gaagctccct cgtgcgctct cctgttccga ccctgccgct    1860
taccggatac ctgtccgcct ttctcccttc gggaagcgtg gcgctttctc aatgctcacg    1920
ctgtaggtat ctcagttcgg tgtaggtcgt tcgctccaag ctgggctgtg tgcacgaacc    1980
ccccgttcag cccgaccgct cgcccttatc cggtaactat cgtcttgagt ccaacccggt    2040
aagacacgac ttatcgccac tggcagcagc cactggtaac aggattagca gagcgaggta    2100
tgtaggcggt gctacagagt tcttgaagtg gtggcctaac tacggctaca ctagaaggac    2160
agtatttggt atctgcgctc tgctgaagcc agttaccttc ggaaaaagag ttggtagctc    2220
ttgatccggc aaacaaacca ccgctggtag cggtggtttt tttgtttgca agcagcagat    2280
tacgcgcaga aaaaaggat ctcaagaaga tcctttgatc ttttctacgg gtctgacgc    2340 tcagtggaac gaaaactcac gttaagggat tttggtcatg agattatcaa aaaggatctt    2400
cacctagatc cttttaaatt aaaaatgaag ttttaaatca atctaaagta tatatgagta    2460
aacttggtct gacagttacc aatgcttaat cagtgaggca cctatctcag cgatctgtct    2520
atttcgttca tccatagttg cctgactccc cgtcgtgtag ataactacga tacgggaggg    2580
cttaccatct ggccccagtg ctgcaatgat accgcgagac ccacgctcac cggctccaga    2640
tttatcagca ataaaccagc cagccggaag ggccgagcgc agaagtggtc ctgcaactttt    2700 atccgcctcc atccagtcta ttaattgttg ccgggaagct agagtaagta gttcgccagt    2760
taatagtttg cgcaacgttg ttgccattgc tacaggcatc gtggtgtcac gctcgtcgtt    2820
tggtatggct tcattcagct ccggttccca acgatcaagg cgagttacat gatcccccat    2880
gttgtgcaaa aaagcggtta gctccttcgg tcctccgatc gttgtcagaa gtaagttggc    2940
cgcagtgtta tcactcatgg ttatggcagc actgcataat tctcttactg tcatgccatc    3000
cgtaagatgc ttttctgtga ctggtgagta ctcaaccaag tcattctgag aatagtgtat    3060
gcggcgaccg agttgctctt gcccggcgtc aatacgggat aataccgcgc cacatagcag    3120
aactttaaaa gtgctcatca ttggaaaacg ttcttcgggg cgaaaactct caaggatctt    3180
accgctgttg agatccagtt cgatgtaacc cactcgtgca cccaactgat cttcagcatc    3240
ttttactttc accagcgttt ctgggtgagc aaaaacagga aggcaaaatg ccgcaaaaaa    3300
gggaataagg gcgacacgga aatgttgaat actcatactc ttcctttttc aatattattg    3360
aagcatttat cagggttatt gtctcatgag cggatacata tttgaatgta tttagaaaaa    3420
taaacaaata ggggttccgc gcacatttcc ccgaaaagtg ccacctgacg tcgacggatc    3480
gggagatctc ccgatcccct atggtcgact ctcagtacaa tctgctctga tgccgcatag    3540
ttaagccagt atctgctccc tgcttgtgtg ttggaggtcg ctgagtagtg cgcgagcaaa    3600
atttaagcta caacaaggca aggcttgacc gacaattgca tgaagaatct gcttagggtt    3660
aggcgttttg cgctgcttcg cgatgtacgg gccagatata cgcgttgaca ttgattattg    3720
actagttatt aatagtaatc aattacgggg tcattagttc atagcccata tatggagttc    3780
cgcgttacat aacttacggt aaatggcccg cctggctgac cgcccaacga cccccgccca    3840
ttgacgtcaa taatgacgta tgttcccata gtaacgccaa tagggacttt ccattgacgt    3900
caatgggtgg actatttacg gtaaactgcc cacttggcag tacatcaagt gtatcatatg    3960
ccaagtacgc cccctattga cgtcaatgac ggtaaatggc ccgcctggca ttatgcccag    4020
tacatgacct tatgggactt tcctacttgg cagtacatct acgtattagt catcgctatt    4080
accatggtga tgcggttttg gcagtacatc aatgggcgtg gatagcggtt tgactcacgg    4140
```

```
ggatttccaa gtctccaccc cattgacgtc aatgggagtt tgttttggca ccaaaatcaa      4200
cgggactttc caaaatgtcg taacaactcc gccccattga cgcaaatggg cggtaggcgt      4260
gtacggtggg aggtctatat aagcagagct ctctggctaa ctagagaacc cactgcttac      4320
tggcttatcg aaattaatac gactcactat agggagaccc aagcttggta ccgagctcgg      4380
atcgatatct gcggcctagc tagcgcttaa ggcctgttaa ccggtcgtac gtctccggat      4440
tcgaattcgc aacatctaca atggccttga cctttgcttt actggtggcc ctcctggtgc      4500
tcagctgcaa gtcaagctgc tctgtgggct gtgatctgcc tcaaacccac agcctgggta      4560
gcaggaggac cttgatgctc ctggcacaga tgaggagaat ctctcttttc tcctgcttga      4620
aggacagaca tgactttgga tttccccagg aggagtttgg caaccagttc caaaaggctg      4680
aaaccatccc tgtcctccat gagatgatcc agcagatctt caatctcttc agcacaaagg      4740
actcatctgc tgcttgggat gagaccctcc tagacaaatt ctacactgaa ctctaccagc      4800
agctgaatga cctggaagcc tgtgtgatac aggggtggg ggtgacagag actcccctga      4860
tgaaggagga ctccattctg gctgtgagga aatacttcca aagaatcact ctctatctga      4920
aagagaagaa atacagccct tgtgcctggg aggttgtcag agcagaaatc atgagatctt      4980
tttctttgtc aacaaacttg caagaaagtt taagaagtaa ggaatgaaaa ctggatccgc      5040
ggccgcatag ataactgatc cagtgtgctg gaattaattc gctgtctgcg agggccagct      5100
gttgggtga gtactccctc tcaaaagcgg gcatgacttc tgcgctaaga ttgtcagttt      5160
ccaaaaacga ggaggatttg atattcacct ggcccgcggt gatgcctttg agggtggccg      5220
cgtccatctg gtcagaaaag acaatctttt tgttgtcaag cttgaggtgt ggcaggcttg      5280
agatctggcc atacacttga gtgacaatga catccacttt gcctttctct ccacaggtgt      5340
ccactcccag gtccaactgc aggtcgagca tgcatctagg gcggccaatt ccgcccctct      5400
ccctcccccc ccctaacgt tactggccga agccgcttgg aataaggccg gtgtgcgttt      5460
gtctatatgt gattttccac catattgccg tcttttggca atgtgagggc ccggaaacct      5520
ggccctgtct tcttgacgag cattcctagg ggtctttccc ctctcgccaa aggaatgcaa      5580
ggtctgttga atgtcgtgaa ggaagcagtt cctctggaag cttcttgaag acaaacaacg      5640
tctgtagcga ccctttgcag gcagcggaac cccccacctg gcgacaggtg cctctgcggc      5700
caaaagccac gtgtataaga tacacctgca aaggcggcac aaccccagtg ccacgttgtg      5760
agttggatag ttgtggaaag agtcaaatgg ctctcctcaa gcgtattcaa caaggggctg      5820
aaggatgccc agaaggtacc ccattgtatg ggatctgatc tggggcctcg gtgcacatgc      5880
tttacatgtg tttagtcgag gttaaaaaaa cgtctaggcc ccccgaacca cggggacgtg      5940
gttttccttt gaaaaacacg atgataagct tgccacaacc c                          5981
```

<210> SEQ ID NO 6
<211> LENGTH: 615
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: IRES

<400> SEQUENCE: 6

```
cgcccctctc cctcccccc ccctaacgtt actggccgaa gccgcttgga ataaggccgg       60
tgtgcgtttg tctatatgtg attttccacc atattgccgt cttttggcaa tgtgagggcc     120
```

```
cggaaacctg gccctgtctt cttgacgagc attcctaggg gtctttcccc tctcgccaaa      180
ggaatgcaag gtctgttgaa tgtcgtgaag gaagcagttc ctctggaagc ttcttgaaga      240
caaacaacgt ctgtagcgac cctttgcagg cagcggaacc ccccacctgg cgacaggtgc      300
ctctgcggcc aaaagccacg tgtataagat acacctgcaa aggcggcaca accccagtgc      360
cacgttgtga gttggatagt tgtggaaaga gtcaaatggc tctcctcaag cgtattcaac      420
aaggggctga aggatgccca gaaggtaccc cattgtatgg gatctgatct ggggcctcgg      480
tgcacatgct ttacatgtgt ttagtcgagg ttaaaaaaac gtctaggccc cccgaaccac      540
ggggacgtgg ttttcctttg aaaaacacga tgataagctt gccacaaccc gggataattc      600
ctgcagccaa tatgg                                                      615

<210> SEQ ID NO 7
<211> LENGTH: 5849
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: ISRE/SV40 luc vector
<220> FEATURE:
<221> NAME/KEY: CDS
<222> LOCATION: (328)..(1980)

<400> SEQUENCE: 7
cccgggaggt accgagctct tacgcgtgct agctcgactc gggaaaggga aaccgaaact       60
gaagcccctc gggaaaggga aaccgaaact gaagcccgat ctgcatctca attagtcagc      120
aaccatagtc ccgcccctaa ctccgcccat cccgcccctc actccgccca gttccgccca      180
ttctccgccc catggctgac taattttttt tatttatgca gaggccgagg ccgcctcggc      240
ctctgagcta ttccagaagt agtgaggagg ctttttttgga ggcctaggct tttgcaaaaa     300
gcttggcatt ccggtactgt tggtaaa atg gaa gac gcc aaa aac ata aag aaa     354
                                Met Glu Asp Ala Lys Asn Ile Lys Lys
                                 1               5 ggc ccg gcg cca ttc tat cct cta gag gat gga acc gct gga gag caa      402
Gly Pro Ala Pro Phe Tyr Pro Leu Glu Asp Gly Thr Ala Gly Glu Gln
 10              15                  20                  25 ctg cat aag gct atg aag aga tac gcc ctg gtt cct gga aca att gct      450
Leu His Lys Ala Met Lys Arg Tyr Ala Leu Val Pro Gly Thr Ile Ala
                 30                  35                  40 ttt aca gat gca cat atc gag gtg aac atc acg tac gcg gaa tac ttc      498
Phe Thr Asp Ala His Ile Glu Val Asn Ile Thr Tyr Ala Glu Tyr Phe
             45                  50                  55 gaa atg tcc gtt cgg ttg gca gaa gct atg aaa cga tat ggg ctg aat      546
Glu Met Ser Val Arg Leu Ala Glu Ala Met Lys Arg Tyr Gly Leu Asn
         60                  65                  70 aca aat cac aga atc gtc gta tgc agt gaa aac tct ctt caa ttc ttt      594
Thr Asn His Arg Ile Val Val Cys Ser Glu Asn Ser Leu Gln Phe Phe
     75                  80                  85 atg ccg gtg ttg ggc gcg tta ttt atc gga gtt gca gtt gcg ccc gcg      642
Met Pro Val Leu Gly Ala Leu Phe Ile Gly Val Ala Val Ala Pro Ala
 90                  95                 100                 105 aac gac att tat aat gaa cgt gaa ttg ctc aac agt atg aac att tcg      690
Asn Asp Ile Tyr Asn Glu Arg Glu Leu Leu Asn Ser Met Asn Ile Ser
                110                 115                 120 cag cct acc gta gtg ttt gtt tcc aaa aag ggg ttg caa aaa att ttg      738
Gln Pro Thr Val Val Phe Val Ser Lys Lys Gly Leu Gln Lys Ile Leu
            125                 130                 135
```

| | | |
|---|---|---|
| aac gtg caa aaa aaa tta cca ata atc cag aaa att att atc atg gat<br>Asn Val Gln Lys Lys Leu Pro Ile Ile Gln Lys Ile Ile Ile Met Asp<br>140                          145                        150 | 786 |
| tct aaa acg gat tac cag gga ttt cag tcg atg tac acg ttc gtc aca<br>Ser Lys Thr Asp Tyr Gln Gly Phe Gln Ser Met Tyr Thr Phe Val Thr<br>          155                      160                      165 | 834 |
| tct cat cta cct ccc ggt ttt aat gaa tac gat ttt gta cca gag tcc<br>Ser His Leu Pro Pro Gly Phe Asn Glu Tyr Asp Phe Val Pro Glu Ser<br>170                          175                        180                      185 | 882 |
| ttt gat cgt gac aaa aca att gca ctg ata atg aat tcc tct gga tct<br>Phe Asp Arg Asp Lys Thr Ile Ala Leu Ile Met Asn Ser Ser Gly Ser<br>                     190                      195                      200 | 930 |
| act ggg tta cct aag ggt gtg gcc ctt ccg cat aga act gcc tgc gtc<br>Thr Gly Leu Pro Lys Gly Val Ala Leu Pro His Arg Thr Ala Cys Val<br>                     205                      210                      215 | 978 |
| aga ttc tcg cat gcc aga gat cct att ttt ggc aat caa atc att ccg<br>Arg Phe Ser His Ala Arg Asp Pro Ile Phe Gly Asn Gln Ile Ile Pro<br>                     220                      225                      230 | 1026 |
| gat act gcg att tta agt gtt gtt cca ttc cat cac ggt ttt gga atg<br>Asp Thr Ala Ile Leu Ser Val Val Pro Phe His His Gly Phe Gly Met<br>          235                      240                      245 | 1074 |
| ttt act aca ctc gga tat ttg ata tgt gga ttt cga gtc gtc tta atg<br>Phe Thr Thr Leu Gly Tyr Leu Ile Cys Gly Phe Arg Val Val Leu Met<br>250                          255                        260                      265 | 1122 |
| tat aga ttt gaa gaa gag ctg ttt tta cga tcc ctt cag gat tac aaa<br>Tyr Arg Phe Glu Glu Glu Leu Phe Leu Arg Ser Leu Gln Asp Tyr Lys<br>                     270                      275                      280 | 1170 |
| att caa agt gcg ttg cta gta cca acc cta ttt tca ttc ttc gcc aaa<br>Ile Gln Ser Ala Leu Leu Val Pro Thr Leu Phe Ser Phe Phe Ala Lys<br>                     285                      290                      295 | 1218 |
| agc act ctg att gac aaa tac gat tta tct aat tta cac gaa att gct<br>Ser Thr Leu Ile Asp Lys Tyr Asp Leu Ser Asn Leu His Glu Ile Ala<br>          300                      305                      310 | 1266 |
| tct ggg ggc gca cct ctt tcg aaa gaa gtc ggg gaa gcg gtt gca aaa<br>Ser Gly Gly Ala Pro Leu Ser Lys Glu Val Gly Glu Ala Val Ala Lys<br>          315                      320                      325 | 1314 |
| cgc ttc cat ctt cca ggg ata cga caa gga tat ggg ctc act gag act<br>Arg Phe His Leu Pro Gly Ile Arg Gln Gly Tyr Gly Leu Thr Glu Thr<br>330                          335                        340                      345 | 1362 |
| aca tca gct att ctg att aca ccc gag ggg gat gat aaa ccg ggc gcg<br>Thr Ser Ala Ile Leu Ile Thr Pro Glu Gly Asp Asp Lys Pro Gly Ala<br>                     350                      355                      360 | 1410 |
| gtc ggt aaa gtt gtt cca ttt ttt gaa gcg aag gtt gtg gat ctg gat<br>Val Gly Lys Val Val Pro Phe Phe Glu Ala Lys Val Val Asp Leu Asp<br>          365                      370                      375 | 1458 |
| acc ggg aaa acg ctg ggc gtt aat cag aga ggc gaa tta tgt gtc aga<br>Thr Gly Lys Thr Leu Gly Val Asn Gln Arg Gly Glu Leu Cys Val Arg<br>          380                      385                      390 | 1506 |
| gga cct atg att atg tcc ggt tat gta aac aat ccg gaa gcg acc aac<br>Gly Pro Met Ile Met Ser Gly Tyr Val Asn Asn Pro Glu Ala Thr Asn<br>395                          400                        405 | 1554 |
| gcc ttg att gac aag gat gga tgg cta cat tct gga gac ata gct tac<br>Ala Leu Ile Asp Lys Asp Gly Trp Leu His Ser Gly Asp Ile Ala Tyr<br>410                          415                        420                      425 | 1602 |
| tgg gac gaa gac gaa cac ttc ttc ata gtt gac cgc ttg aag tct tta<br>Trp Asp Glu Asp Glu His Phe Phe Ile Val Asp Arg Leu Lys Ser Leu<br>                     430                      435                      440 | 1650 |
| att aaa tac aaa gga tat cag gtg gcc ccc gct gaa ttg gaa tcg ata<br>Ile Lys Tyr Lys Gly Tyr Gln Val Ala Pro Ala Glu Leu Glu Ser Ile | 1698 |

-continued

|  |  |  |  |  |  |  |  |  |  |  |  |  |  |  |  |
|---|---|---|---|---|---|---|---|---|---|---|---|---|---|---|---|
|  |  | 445 |  |  |  | 450 |  |  |  |  | 455 |  |  |  |  |
| ttg | tta | caa | cac | ccc | aac | atc | ttc | gac | gcg | ggc | gtg | gca | ggt | ctt | ccc |
| Leu | Leu | Gln | His | Pro | Asn | Ile | Phe | Asp | Ala | Gly | Val | Ala | Gly | Leu | Pro |
|  |  | 460 |  |  |  | 465 |  |  |  |  | 470 |  |  |  |  |

1746

| gac | gat | gac | gcc | ggt | gaa | ctt | ccc | gcc | gcc | gtt | gtt | gtt | ttg | gag | cac |
|---|---|---|---|---|---|---|---|---|---|---|---|---|---|---|---|
| Asp | Asp | Asp | Ala | Gly | Glu | Leu | Pro | Ala | Ala | Val | Val | Val | Leu | Glu | His |
| 475 |  |  |  |  | 480 |  |  |  |  | 485 |  |  |  |  |  |

1794

| gga | aag | acg | atg | acg | gaa | aaa | gag | atc | gtg | gat | tac | gtg | gcc | agt | caa |
|---|---|---|---|---|---|---|---|---|---|---|---|---|---|---|---|
| Gly | Lys | Thr | Met | Thr | Glu | Lys | Glu | Ile | Val | Asp | Tyr | Val | Ala | Ser | Gln |
| 490 |  |  |  |  | 495 |  |  |  |  | 500 |  |  |  |  | 505 |

1842

| gta | aca | acc | gcg | aaa | aag | ttg | cgc | gga | gga | gtt | gtg | ttt | gtg | gac | gaa |
|---|---|---|---|---|---|---|---|---|---|---|---|---|---|---|---|
| Val | Thr | Thr | Ala | Lys | Lys | Leu | Arg | Gly | Gly | Val | Val | Phe | Val | Asp | Glu |
|  |  |  |  | 510 |  |  |  |  | 515 |  |  |  |  | 520 |  |

1890

| gta | ccg | aaa | ggt | ctt | acc | gga | aaa | ctc | gac | gca | aga | aaa | atc | aga | gag |
|---|---|---|---|---|---|---|---|---|---|---|---|---|---|---|---|
| Val | Pro | Lys | Gly | Leu | Thr | Gly | Lys | Leu | Asp | Ala | Arg | Lys | Ile | Arg | Glu |
|  |  |  | 525 |  |  |  |  | 530 |  |  |  |  | 535 |  |  |

1938

| atc | ctc | ata | aag | gcc | aag | aag | ggc | gga | aag | tcc | aaa | ttg | taa |
|---|---|---|---|---|---|---|---|---|---|---|---|---|---|
| Ile | Leu | Ile | Lys | Ala | Lys | Lys | Gly | Gly | Lys | Ser | Lys | Leu |  |
|  |  |  | 540 |  |  |  |  | 545 |  |  |  | 550 |  |

1980

```
aatgtaactg tattcagcga tgacgaaatt cttagctatt gtaatactgc gatgagtggc    2040
agggcggggc gtaattttt taaggcagtt attggtgccc ttaaacgcct ggtgctacgc     2100
ctgaataagt gataataagc ggatgaatgg cagaaattcg ccggatcttt gtgaaggaac    2160
cttacttctg tggtgtgaca taattggaca aactacctac agagatttaa agctctaagg    2220
taaatataaa attttaagt gtataatgtg ttaaactact gattctaatt gtttgtgtat     2280
tttagattcc aacctatgga actgatgaat gggagcagtg gtggaatgcc tttaatgagg    2340
aaaacctgtt ttgctcagaa gaaatgccat ctagtgatga tgaggctact gctgactctc    2400
aacattctac tcctccaaaa aagaagagaa aggtagaaga ccccaaggac tttccttcag    2460
aattgctaag ttttttgagt catgctgtgt ttagtaatag aactcttgct tgctttgcta    2520
tttacaccac aaaggaaaaa gctgcactgc tatacaagaa aattatggaa aaatattctg    2580
taacctttat aagtaggcat aacagttata atcataacat actgtttttt cttactccac    2640
acaggcatag agtgtctgct attaataact atgctcaaaa attgtgtacc tttagctttt    2700
taatttgtaa agggtaaat aaggaatatt tgatgtatag tgccttgact agagatcata    2760
atcagccata ccacatttgt agaggtttta cttgctttaa aaaacctccc acacctcccc    2820
ctgaacctga acataaaat gaatgcaatt gttgttgtta acttgtttat tgcagcttat     2880
aatggttaca aataaagcaa tagcatcaca aatttcacaa ataaagcatt tttttcactg    2940
cattctagtt gtggtttgtc caaactcatc aatgtatctt atcatgtctg gatccgtcga    3000
ccgatgccct tgagagcctt caacccagtc agctccttcc ggtgggcgcg ggcatgact     3060
atcgtcgccg cacttatgac tgtcttcttt atcatgcaac tcgtaggaca ggtgccggca    3120
gcgctcttcc gcttcctcgc tcactgactc gctgcgctcg gtcgttcggc tgcggcgagc    3180
ggtatcagct cactcaaagg cggtaatacg gttatccaca gaatcagggg ataacgcagg    3240
aaagaacatg tgagcaaaag gccagcaaaa ggccaggaac cgtaaaaagg ccgcgttgct    3300
ggcgttttc cataggctcc gcccccctga cgagcatcac aaaaatcgac gctcaagtca    3360
gaggtggcga aacccgacag gactataaag ataccaggcg tttccccctg gaagctccct    3420
cgtgcgctct cctgttccga ccctgccgct taccggatac ctgtccgcct ttctcccttc    3480
gggaagcgtg cgcttttctc aatgctcacg ctgtaggtat ctcagttcgg tgtaggtcgt    3540
tcgctccaag ctgggctgtg tgcacgaacc ccccgttcag cccgaccgct gcgccttatc    3600
```

```
cggtaactat cgtcttgagt ccaacccggt aagacacgac ttatcgccac tggcagcagc    3660
cactggtaac aggattagca gagcgaggta tgtaggcggt gctacagagt tcttgaagtg    3720
gtggcctaac tacggctaca ctagaaggac agtatttggt atctgcgctc tgctgaagcc    3780
agttaccttc ggaaaaagag ttggtagctc ttgatccggc aaacaaacca ccgctggtag    3840
cggtggtttt tttgtttgca agcagcagat tacgcgcaga aaaaaaggat ctcaagaaga    3900
tcctttgatc ttttctacgg ggtctgacgc tcagtggaac gaaaactcac gttaagggat    3960
tttggtcatg agattatcaa aaaggatctt cacctagatc cttttaaatt aaaaatgaag    4020
ttttaaatca atctaaagta tatatgagta aacttggtct gacagttacc aatgcttaat    4080
cagtgaggca cctatctcag cgatctgtct atttcgttca tccatagttg cctgactccc    4140
cgtcgtgtag ataactacga tacgggaggg cttaccatct ggccccagtg ctgcaatgat    4200
accgcgagac ccacgctcac cggctccaga tttatcagca ataaaccagc cagccggaag    4260
ggccgagcgc agaagtggtc ctgcaacttt atccgcctcc atccagtcta ttaattgttg    4320
ccgggaagct agagtaagta gttcgccagt taatagtttg cgcaacgttg ttgccattgc    4380
tacaggcatc gtggtgtcac gctcgtcgtt tggtatggct tcattcagct ccggttccca    4440
acgatcaagg cgagttacat gatcccccat gttgtgcaaa aaagcggtta gctccttcgg    4500
tcctccgatc gttgtcagaa gtaagttggc cgcagtgtta tcactcatgg ttatggcagc    4560
actgcataat tctcttactg tcatgccatc cgtaagatgc ttttctgtga ctggtgagta    4620
ctcaaccaag tcattctgag aatagtgtat gcggcgaccg agttgctctt gcccggcgtc    4680
aatacgggat aataccgcgc cacatagcag aactttaaaa gtgctcatca ttggaaaacg    4740
ttcttcgggg cgaaaactct caaggatctt accgctgttg agatccagtt cgatgtaacc    4800
cactcgtgca cccaactgat cttcagcatc ttttactttc accagcgttt ctgggtgagc    4860
aaaaacagga aggcaaaatg ccgcaaaaaa gggaataagg gcgacacgga aatgttgaat    4920
actcatactc ttcctttttc aatattattg aagcatttat cagggttatt gtctcatgag    4980
cggatacata tttgaatgta tttagaaaaa taaacaaata ggggttccgc gcacatttcc    5040
ccgaaaagtg ccacctgacg cgccctgtag cggcgcatta agcgcggcgg gtgtggtggt    5100
tacgcgcagc gtgaccgcta cacttgccag cgccctagcg cccgctcctt tcgctttctt    5160
cccttccttt ctcgccacgt tcgccggctt tccccgtcaa gctctaaatc ggggctccc    5220 tttagggttc cgatttagtg ctttacggca cctcgacccc aaaaaacttg attagggtga    5280
tggttcacgt agtgggccat cgccctgata gacggttttt cgccctttga cgttggagtc    5340
cacgttcttt aatagtggac tcttgttcca aactggaaca acactcaacc ctatctcggt    5400
ctattctttt gatttataag ggattttgcc gatttcggcc tattggttaa aaaatgagct    5460
gatttaacaa aaatttaacg cgaattttaa caaatatta acgtttacaa tttcccattc    5520
gccattcagg ctgcgcaact gttgggaagg gcgatcggtg cgggcctctt cgctattacg    5580
ccagcccaag ctaccatgat aagtaagtaa tattaaggta cgtggaggtt ttacttgctt    5640
taaaaaacct cccacacctc cccctgaacc tgaaacataa aatgaatgca attgttgttg    5700
ttaacttgtt tattgcagct tataatggtt acaataaaag caatagcatc acaaatttca    5760
caaataaagc atttttttca ctgcattcta gttgtggttt gtccaaactc atcaatgtat    5820
cttatggtac tgtaactgag ctaacataa                                      5849
```

<210> SEQ ID NO 8

<211> LENGTH: 550
<212> TYPE: PRT
<213> ORGANISM: Artificial Sequence
<220> FEATURE:
<223> OTHER INFORMATION: Synthetic Construct

<400> SEQUENCE: 8

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
```

```
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp His Phe
        420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 9
<211> LENGTH: 4412
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: ISRE/SV40 EGFP-1
<220> FEATURE:
<221> NAME/KEY: CDS
<222> LOCATION: (358)..(1077)

<400> SEQUENCE: 9
tagttattac tagcgctacc ggactcagac tcgggaaagg gaaaccgaaa ctgaagcccc      60
tcgggaaagg gaaaccgaaa ctgaagcccg atctgcatct caattagtca gcaaccatag     120
tcccgcccct aactccgccc atcccgcccc taactccgcc cagttccgcc cattctccgc     180
cccatggctg actaattttt tttatttatg cagaggccga ggccgcctcg gcctctgagc     240
tattccagaa gtagtgagga ggcttttttg gaggcctagg cttttgcaaa tctcgagctc     300
aagcttcgaa ttctgcagtc gacggtaccg cgggcccggg atccaccggt cgccacc       357 atg gtg agc aag ggc gag gag ctg ttc acc ggg gtg gtg ccc atc ctg      405
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      453
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      501
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc      549
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag      597
```

| | | |
|---|---|---|
| Leu Thr Tyr Gly Val Gln Cys Phe Ser Arg Tyr Pro Asp His Met Lys<br>65                           70                    75                  80 | | |

```
cag cac gac ttc ttc aag tcc gcc atg ccc gaa ggc tac gtc cag gag         645
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag         693
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc         741
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac         789
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac         837
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc         885
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc         933
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg         981
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc        1029
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa        1077
Val Thr Ala Ala Gly Ile Thr Leu Gly Met Asp Glu Leu Tyr Lys
225                 230                 235 agcggccgcg actctagatc ataatcagcc ataccacatt tgtagaggtt ttacttgctt      1137
taaaaaacct cccacacctc cccctgaacc tgaaacataa aatgaatgca attgttgttg      1197
ttaacttgtt tattgcagct tataatggtt acaaataaag caatagcatc acaaatttca      1257
caaataaagc atttttttca ctgcattcta gttgtggttt gtccaaactc atcaatgtat      1317
cttaaggcgt aaattgtaag cgttaatatt tgttaaaat tcgcgttaaa ttttttgttaa      1377 atcagctcat tttttaacca ataggccgaa atcggcaaaa tcccttataa atcaaaagaa      1437
tagaccgaga tagggttgag tgttgttcca gtttggaaca agagtccact attaagaac       1497 gtggactcca acgtcaaagg gcgaaaaacc gtctatcagg gcgatggccc actacgtgaa      1557
ccatcaccct aatcaagttt ttggggtcg aggtgccgta aagcactaaa tcggaaccct       1617
aaagggagcc cccgatttag agcttgacgg ggaaagccgg cgaacgtggc gagaaaggaa      1677
gggaagaaag cgaaaggagc gggcgctagg gcgctggcaa gtgtagcggt cacgctgcgc      1737
gtaaccacca cacccgccgc gcttaatgcg ccgctacagg gcgcgtcagg tggcactttt      1797
cggggaaatg tgcgcggaac ccctatttgt ttatttttct aaatacattc aaatatgtat     1857
ccgctcatga caataaacc ctgataaatg cttcaataat attgaaaaag gaagagtcct       1917
gaggcggaaa gaaccagctg tggaatgtgt gtcagttagg gtgtggaaag tccccaggct      1977
ccccagcagg cagaagtatg caaagcatgc atctcaatta gtcagcaacc aggtgtggaa      2037 agtcccagg ctccccagca ggcagaagta tgcaaagcat gcatctcaat tagtcagcaa       2097
ccatagtccc gcccctaact ccgcccatcc cgcccctaac tccgcccagt tccgcccatt     2157
```

```
ctccgcccca tggctgacta attttttttta tttatgcaga ggccgaggcc gcctcggcct    2217
ctgagctatt ccagaagtag tgaggaggct tttttggagg cctaggcttt tgcaaagatc    2277
gatcaagaga caggatgagg atcgtttcgc atgattgaac aagatggatt gcacgcaggt    2337
tctccggccg cttgggtgga gaggctattc ggctatgact gggcacaaca gacaatcggc    2397
tgctctgatg ccgccgtgtt ccggctgtca gcgcaggggc gcccggttct ttttgtcaag    2457
accgacctgt ccggtgccct gaatgaactg caagacgagg cagcgcggct atcgtggctg    2517
gccacgacgg gcgttccttg cgcagctgtg ctcgacgttg tcactgaagc gggaagggac    2577
tggctgctat tgggcgaagt gccggggcag gatctcctgt catctcacct tgctcctgcc    2637
gagaaagtat ccatcatggc tgatgcaatg cggcggctgc atacgcttga tccggctacc    2697
tgcccattcg accaccaagc gaaacatcgc atcgagcgag cacgtactcg gatggaagcc    2757
ggtcttgtcg atcaggatga tctggacgaa gagcatcagg ggctcgcgcc agccgaactg    2817
ttcgccaggc tcaaggcgag catgcccgac ggcgaggatc tcgtcgtgac ccatggcgat    2877
gcctgcttgc cgaatatcat ggtggaaaat ggccgctttt ctggattcat cgactgtggc    2937
cggctgggtg tggcggaccg ctatcaggac atagcgttgg ctacccgtga tattgctgaa    2997
gagcttggcg gcgaatgggc tgaccgcttc ctcgtgcttt acggtatcgc cgctcccgat    3057
tcgcagcgca tcgccttcta tcgccttctt gacgagttct tctgagcggg actctggggt    3117
tcgaaatgac cgaccaagcg acgcccaacc tgccatcacg agatttcgat tccaccgccg    3177
ccttctatga aggttgggc ttcggaatcg ttttccggga cgccggctgg atgatcctcc    3237
agcgcgggga tctcatgctg gagttcttcg cccacctag ggggaggcta actgaaacac    3297
ggaaggagac aataccggaa ggaacccgcg ctatgacggc aataaaaaga cagaataaaa    3357
cgcacggtgt tgggtcgttt gttcataaac gcggggttcg gtcccagggc tggcactctg    3417
tcgataccc accgagaccc cattggggcc aatacgcccg cgtttcttcc ttttcccac    3477
cccacccccc aagttcgggt gaaggcccag ggctcgcagc caacgtcggg gcggcaggcc    3537
ctgccatagc ctcaggttac tcatatatac tttagattga tttaaaactt cattttaat    3597
ttaaaaggat ctaggtgaag atccttttg ataatctcat gaccaaaatc ccttaacgtg    3657
agttttcgtt ccactgagcg tcagaccccg tagaaaagat caaaggatct cttgagatc    3717
cttttttct gcgcgtaatc tgctgcttgc aaacaaaaaa accaccgcta ccagcggtgg    3777
tttgtttgcc ggatcaagag ctaccaactc ttttccgaa ggtaactggc ttcagcagag    3837
cgcagatacc aaatactgtc cttctagtgt agccgtagtt aggccaccac ttcaagaact    3897
ctgtagcacc gcctacatac ctcgctctgc taatcctgtt accagtggct gctgccagtg    3957
gcgataagtc gtgtcttacc gggttggact caagacgata gttaccggat aaggcgcagc    4017
ggtcgggctg aacggggggt tcgtgcacac agcccagctt ggagcgaacg acctacaccg    4077
aactgagata cctacagcgt gagctatgag aaagcgccac gcttcccgaa gggagaaagg    4137
cggacaggta tccggtaagc ggcagggtcg gaacaggaga gcgcacgagg gagcttccag    4197
ggggaaacgc ctggtatctt tatagtcctg tcgggtttcg ccacctctga cttgagcgtc    4257
gatttttgtg atgctcgtca gggggggcgga gcctatggaa aaacgccagc aacgcggcct    4317
ttttacggtt cctggccttt tgctggcctt ttgctcacat gttctttcct gcgttatccc    4377
ctgattctgt ggataaccgt attaccgcca tgcat                                4412
```

<210> SEQ ID NO 10
<211> LENGTH: 239

```
<212> TYPE: PRT
<213> ORGANISM: Artificial Sequence
<220> FEATURE:
<223> OTHER INFORMATION: Synthetic Construct

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
<211> LENGTH: 70
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: 5xNFkB

<400> SEQUENCE: 11
tggggacttt ccgctgggga ctttccgctg gggactttcc gctggggact ttccgctggg    60
gactttccgc                                                          70

<210> SEQ ID NO 12
<211> LENGTH: 29
<212> TYPE: DNA
<213> ORGANISM: Artificial Sequence
<220> FEATURE:
<223> OTHER INFORMATION: synthetic

<400> SEQUENCE: 12
```
ctcgggaaag ggaaaccgaa actgaagcc                                        29

<210> SEQ ID NO 13
<211> LENGTH: 37
<212> TYPE: DNA
<213> ORGANISM: Artificial Sequence
<220> FEATURE:
<223> OTHER INFORMATION: synthetic

<400> SEQUENCE: 13
acgtgaattc gcaacatcta caatggcctt gaccttt                               37

<210> SEQ ID NO 14
<211> LENGTH: 35
<212> TYPE: DNA
<213> ORGANISM: Artificial Sequence
<220> FEATURE:
<223> OTHER INFORMATION: synthetic

<400> SEQUENCE: 14
gatcggatcc agttttcatt ccttacttct taaac                                 35

<210> SEQ ID NO 15
<211> LENGTH: 34
<212> TYPE: DNA
<213> ORGANISM: Artificial Sequence
<220> FEATURE:
<223> OTHER INFORMATION: synthetic

<400> SEQUENCE: 15
tcgtcccggg atggcttcca aggtgtacga cccc                                  34

<210> SEQ ID NO 16
<211> LENGTH: 32
<212> TYPE: DNA
<213> ORGANISM: Artificial Sequence
<220> FEATURE:
<223> OTHER INFORMATION: synthetic

<400> SEQUENCE: 16
ctagtctaga ttactgctcg ttcttcagca cg                                    32

<210> SEQ ID NO 17
<211> LENGTH: 5000
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: pTRE/IRES/IFNA2/hRL vector

<400> SEQUENCE: 17
ctcgagttta ctccctatca gtgatagaga acgtatgtcg agtttactcc ctatcagtga      60
tagagaacga tgtcgagttt actccctatc agtgatagag aacgtatgtc gagtttactc    120
cctatcagtg atagagaacg tatgtcgagt ttactcccta tcagtgatag agaacgtatg    180
tcgagtttat ccctatcagt gatagagaac gtatgtcgag tttactccct atcagtgata    240
gagaacgtat gtcgaggtag gcgtgtacgg tgggaggcct atataagcag agctcgttta    300
gtgaaccgtc agatcgcctg gagaattcgc aacatctaca atggccttga cctttgcttt    360
actggtggcc ctcctggtgc tcagctgcaa gtcaagctgc tctgtgggct gtgatctgcc    420
tcaaacccac agcctgggta gcaggaggac cttgatgctc ctggcacaga tgaggagaat    480

-continued

```
ctctcttttc tcctgcttga aggacagaca tgactttgga tttccccagg aggagtttgg      540
caaccagttc caaaaggctg aaaccatccc tgtcctccat gagatgatcc agcagatctt      600
caatctcttc agcacaaagg actcatctgc tgcttgggat gagaccctcc tagacaaatt      660
ctacactgaa ctctaccagc agctgaatga cctggaagcc tgtgtgatac aggggggtggg     720 ggtgacagag actcccctga tgaaggagga ctccattctg gctgtgagga aatacttcca     780
aagaatcact ctctatctga aagagaagaa atacagccct tgtgcctggg aggttgtcag      840
agcagaaatc atgagatctt tttctttgtc aacaaacttg caagaaagtt taagaagtaa      900
ggaatgaaaa ctggatccgc ggccgcatag ataactgatc cagtgtgctg gaattaattc      960
gctgtctgcg agggccagct gttggggtga gtactccctc tcaaaagcgg gcatgacttc     1020
tgcgctaaga ttgtcagttt ccaaaaacga ggaggatttg atattcacct ggcccgcggt     1080
gatgcctttg agggtggccg cgtccatctg gtcagaaaag acaatctttt tgttgtcaag     1140
cttgaggtgt ggcaggcttg agatctggcc atacacttga gtgacaatga catccacttt     1200
gcctttctct ccacaggtgt ccactcccag gtccaactgc aggtcgagca tgcatctagg     1260
gcggccaatt ccgcccctct ccctcccccc ccctaacgt tactggccga agccgcttgg      1320
aataaggccg gtgtgcgttt gtctatatgt gattttccac catattgccg tcttttggca     1380
atgtgagggc ccggaaacct ggccctgtct tcttgacgag cattcctagg gtctttccc      1440 ctctcgccaa aggaatgcaa ggtctgttga atgtcgtgaa ggaagcagtt cctctggaag     1500
cttcttgaag acaaacaacg tctgtagcga cccttttgcag gcagcggaac ccccacctg     1560 gcgacaggtg cctctgcggc caaaagccac gtgtataaga tacacctgca aaggcggcac     1620
aaccccagtg ccacgttgtg agttggatag ttgtggaaag agtcaaatgg ctctcctcaa     1680
gcgtattcaa caaggggctg aaggatgccc agaaggtacc ccattgtatg ggatctgatc     1740
tggggcctcg gtgcacatgc tttacatgtg tttagtcgag gttaaaaaaa cgtctaggcc     1800
ccccgaacca cggggacgtg gttttccttt gaaaaacacg atgataagct tgccacaacc     1860
cgggatggct tccaaggtgt acgaccccga gcaacgcaaa cgcatgatca ctgggcctca     1920
gtggtgggct cgctgcaagc aaatgaacgt gctggactcc ttcatcaact actatgattc     1980
cgagaagcac gccgagaacg ccgtgatttt tctgcatggt aacgctgcct ccagctacct     2040
gtggaggcac gtcgtgcctc acatcgagcc cgtggctaga tgcatcatcc ctgatctgat     2100
cggaatgggt aagtccggca agagcgggaa tggctcatat cgcctcctgg atcactacaa     2160
gtacctcacc gcttggttcg agctgctgaa ccttccaaag aaaatcatct ttgtgggcca     2220 cgactgggg gcttgtctgg ccttttcacta ctcctacgag caccaagaca agatcaaggc     2280
catcgtccat gctgagagtg tcgtggacgt gatcgagtcc tgggacgagt ggcctgacat     2340
cgaggaggat atcgccctga tcaagagcga agagggcgag aaaatggtgc ttgagaataa     2400
cttcttcgtc gagaccatgc tcccaagcaa gatcatgcgg aaactggagc tgaggagtt      2460 cgctgcctac ctggagccat tcaaggagaa gggcgaggtt agacggccta ccctctcctg     2520
gcctcgcgag atccctctcg ttaagggagg caagcccgac gtcgtccaga ttgtccgcaa     2580
ctacaacgcc taccttcggg ccagcgacga tctgcctaag atgttcatcg agtccgaccc     2640
tgggttcttt tccaacgcta ttgtcgaggg agctaagaag ttccctaaca ccgagttcgt     2700
gaaggtgaag ggcctccact tcagccagga ggacgctcca gatgaaatgg gtaagtacat     2760
caagagcttc gtggagcgcg tgctgaagaa cgagcagtaa tctagaggat cataatcagc     2820
cataccacat ttgtagaggt tttacttgct ttaaaaaacc tcccacacct cccctgaac       2880
```

```
ctgaaacata aaatgaatgc aattgttgtt gttaacttgt ttattgcagc ttataatggt   2940
tacaaataaa gcaatagcat cacaaatttc acaaataaag cattttttc actgcctcga    3000 gcttcctcgc tcactgactc gctgcgctcg tcgttcggc tgcggcgagc ggtatcagct    3060
cactcaaagg cggtaatacg gttatccaca gaatcagggg ataacgcagg aagaacatg    3120 tgagcaaaag gccagcaaaa ggccaggaac cgtaaaaagg ccgcgttgct ggcgttttc    3180 cataggctcc gcccccctga cgagcatcac aaaaatcgac gctcaagtca gaggtggcga   3240
aacccgacag gactataaag ataccaggcg tttccccctg gaagctccct cgtgcgctct   3300
cctgttccga ccctgccgct taccggatac ctgtccgcct ttctcccttc gggaagcgtg   3360
gcgctttctc aatgctcacg ctgtaggtat ctcagttcgg tgtaggtcgt tcgctccaag   3420
ctgggctgtg tgcacgaacc ccccgttcag cccgaccgct gcgccttatc cggtaactat   3480
cgtcttgagt ccaacccggt aagacacgac ttatcgccac tggcagcagc cactggtaac   3540
aggattagca gagcgaggta tgtaggcggt gctacagagt tcttgaagtg gtggcctaac   3600
tacggctaca ctagaaggac agtatttggt atctgcgctc tgctgaagcc agttaccttc   3660
ggaaaaagag ttggtagctc ttgatccggc aaacaaacca ccgctggtag cggtggtttt   3720
tttgtttgca agcagcagat tacgcgcaga aaaaaaggat ctcaagaaga tcctttgatc   3780
ttttctacgg ggtctgacgc tcagtggaac gaaaactcac gttaagggat tttggtcatg   3840
agattatcaa aaaggatctt cacctagatc cttttaaatt aaaaatgaag ttttaaatca   3900
atctaaagta tatatgagta aacttggtct gacagttacc aatgcttaat cagtgaggca   3960
cctatctcag cgatctgtct atttcgttca tccatagttg cctgactccc cgtcgtgtag   4020
ataactacga tacgggaggg cttaccatct ggccccagtg ctgcaatgat accgcgagac   4080
ccacgctcac cggctccaga tttatcagca ataaaccagc cagccggaag ggccgagcgc   4140
agaagtggtc ctgcaacttt atccgcctcc atccagtcta ttaattgttg ccgggaagct   4200
agagtaagta gttcgccagt taatagtttg cgcaacgttg ttgccattgc tacaggcatc   4260
gtggtgtcac gctcgtcgtt tggtatggct tcattcagct ccggttccca acgatcaagg   4320
cgagttacat gatcccccat gttgtgcaaa aaagcggtta gctccttcgg tcctccgatc   4380
gttgtcagaa gtaagttggc cgcagtgtta tcactcatgg ttatggcagc actgcataat   4440
tctcttactg tcatgccatc cgtaagatgc ttttctgtga ctggtgagta ctcaaccaag   4500
tcattctgag aatagtgtat gcggcgaccg agttgctctt gcccggcgtc aatacgggat   4560
aataccgcgc cacatagcag aactttaaaa gtgctcatca ttggaaaacg ttcttcgggg   4620
cgaaaactct caaggatctt accgctgttg agatccagtt cgatgtaacc cactcgtgca   4680
cccaactgat cttcagcatc ttttactttc accagcgttt ctgggtgagc aaaaacagga   4740
aggcaaaatg ccgcaaaaaa gggaataagg gcgacacgga aatgttgaat actcatactc   4800
ttcctttttc aatattattg aagcatttat cagggttatt gtctcatgag cggatacata   4860
tttgaatgta tttagaaaaa taaacaaata ggggttccgc gcacatttcc ccgaaaagtg   4920
ccacctgacg tctaagaaac cattattatc atgacattaa cctataaaaa taggcgtatc   4980
acgaggccct ttcgtcttca                                              5000
```